US007572904B2

(12) United States Patent
Cheng et al.

(10) Patent No.: US 7,572,904 B2
(45) Date of Patent: Aug. 11, 2009

(54) NUCLEIC ACIDS ENCODING RESPIRATORY SYNCYTIAL VIRUS SUBGROUP B STRAIN 9320

(75) Inventors: Xing Cheng, Sunnyvale, CA (US); Hyun Jung Park, Sunnyvale, CA (US); Hong Jin, Cupertino, CA (US)

(73) Assignee: MedImmune, LLC, Gaithersburg, MD (US)

( * ) Notice: Subject to any disclaimer, the term of this patent is extended or adjusted under 35 U.S.C. 154(b) by 0 days.

(21) Appl. No.: 10/811,508

(22) Filed: Mar. 26, 2004

(65) Prior Publication Data

US 2004/0224309 A1 Nov. 11, 2004

Related U.S. Application Data

(60) Provisional application No. 60/458,331, filed on Mar. 28, 2003, provisional application No. 60/508,320, filed on Oct. 3, 2003.

(51) Int. Cl.
*C07H 21/00* (2006.01)
*A61K 39/155* (2006.01)

(52) U.S. Cl. ................................ 536/23.72; 424/211.1

(58) Field of Classification Search ............. 424/211.1; 435/69.1; 536/23.72
See application file for complete search history.

(56) References Cited

U.S. PATENT DOCUMENTS 6,225,091 B1 5/2001 Klein et al.
6,713,066 B1 3/2004 Collins et al.

FOREIGN PATENT DOCUMENTS

EP 0 926 246 6/1999
WO WO 98/13501 4/1998
WO WO 99/49017 9/1999
WO WO 02/44334 6/2002
WO WO 02/057302 7/2002
WO WO 2004/028478 4/2004

OTHER PUBLICATIONS

Karron et al. PNAS USA, 1997, 94:13961-13966.*

Bermingham and Collins (1999) "The M2-2 protein of human respiratory syncytial virus is a regulatory factor involved in the balance between RNA replication and transcription" *Proc. Natl. Acad. Sci. USA* 96:11259-11264.

Cheng et al. (2001) "Chimeric subgroup A respiratory syncytial virus with the glycoproteins substituted by those of subgroup B and RSV without the M2-2 gene are attenuated in African green monkeys" *Virology* 283:59-68.

Collins et al. (1995) "Production of infectious human respiratory syncytial virus from cloned cDNA confirms an essential role for the transcription elongation factor from the 5' proximal open reading frame of the M2 mRNA in gene expression and provides a capability for vaccine development" *Proc. Natl. Acad. Sci.* 92:11563-11567.

Collins et al. (1999) "Support plasmids and support proteins required for recovery of recombinant respiratory syncytial virus" *Virology* 259:251-255.

Hardy & Wertz (2000) "The Cys(3)-His(1) motif of the respiratory syncytial virus M2-1 protein is essential for protein function" *J. Virol.* 74(13):5880-5.

Jin et al. (1998) "Recombinant human respiratory syncytial virus (RSV) from cDNA and construction of subgroup A and B chimeric RSV" *Virology* 251:206-214.

Jin et al. (2000) "Respiratory syncytial virus that lacks open reading frame 2 of the M2 gene (M2-2) has altered growth characteristics and is attenuated in rodents" *J. Virol.* 74:74-82.

Jin et al. (2000) "Recombinant respiratory syncytial viruses with deletions in the NS1, NS2, SH, and M2-2 genes are attenuated in vitro and in vivo" *Virology* 273:210-218.

Jin et al. (2003) "Evaluation of recombinant respiratory syncytial virus gene deletion mutants in African green monkeys for their potential as live attenuated vaccine candidates" *Vaccine* 21:3647-3652.

Karron et al. (1997) "Respiratory syncytial virus (RSV) SH and G proteins are not essential for viral replication in vitro: clinical evaluation and molecular characterization of a cold-passaged, attenuated RSV subgroup B mutant" *Proc Natl Acad Sci USA* 94:13961-13966.

Tang et al. (2001) "Requirement of cysteines and length of the human respiratory syncytial virus M2-1 protein for protein function and virus viability" *J. Virol.* 75:11328-11335.

Techaarpornkul et al. (2001) "Functional analysis of recombinant respiratory syncytial virus deletion mutants lacking the small hydrophobic and/or attachment glycoprotein gene" *J Virol* 75:6825-34.

Teng et al. (2000) "Recombinant respiratory syncytial virus that does not express the NS1 or M2-2 protein is highly attenuated and immunogenic in chimpanzees" *J Virol* 74:9317-9321.

Teng et al. (2001) "Contribution of the respiratory syncytial virus G glycoprotein and its secreted and membrane-bound forms to virus replication in vitro and in vivo" *Virology* 289:283-96).

Whitehead et al. (1999) "Replacement of the F and G proteins of respiratory syncytial virus (RSV) subgroup A with those of subgroup B generates chimeric live attenuated RSV subgroup B vaccine candidates" *J Virol* 73:9773-9780.

GenBank accession No. M73544.
GenBank accession No. S75820.
GenBank accession No. D00334.
GenBank accession No. D00392.
GenBank accession No. D00393.
GenBank accession No. D00394.
GenBank accession No. D00395.
GenBank accession No. D00396.

(Continued)

*Primary Examiner*—Stacy B Chen

(57) ABSTRACT

The complete polynucleotide sequence of the human respiratory syncytial virus subgroup B strain 9320 genome is provided. Proteins encoded by this polynucleotide sequence are also provided. Isolated or recombinant RSV (e.g., attenuated recombinant RSV), nucleic acids, and polypeptides, e.g., comprising mutations in the attachment protein G, are also provided, as are immunogenic compositions comprising such isolated or recombinant RSV, nucleic acids, and polypeptides. Related methods are also described.

17 Claims, 4 Drawing Sheets

OTHER PUBLICATIONS

GenBank accession No. D00397.
GenBank accession No. D00736.
GenBank accession No. D01042.
GenBank accession No. M17213.
GenBank accession No. AF013254.
Sullender (2002) "Respiratory Syncytial Virus Genetic and Antigenic Diversity" *Clinical Microbiology Reviews*, 13(1): 1-15.
Fearns et al., 2000, "Functional Analysis of the Genomic and Antigenomic Promoters of Human Respiratory Syncytial Virus." J. Virol. 74(13):6006-6014.
Garcia et al., 1994, "Evolutionary pattern of human respiratory syncytial virus (subgroup A): cocirculating lineages and correlation of genetic and antigenic changes in the G glycoprotein." J. Virol. 68(9):5448-5459.
Smith et al., 2002, "Modelling the structure of the fusion protein from human respiratory syncytial virus." Prot. Engin. 15(5):365-371.
Zimmer et al., 2002, "Cleavage at the furin consensus sequence RAR/KR(109) and presence of the intervening peptide of the respiratory syncytial virus fusion protein are dispensable for virus replication in cell culture." J. Virol. 76(18):9218-9224.
Database UniProt Mar. 1, 2002, XP002407584 retrieved from EBI Database accession No. Q8V220.
Database UniProt Mar. 1, 2001, XP002407585 retrieved from EBI Database accession No. Q9DH68.
Database UniProt Mar. 1, 1992, XP002407586 retrieved from EBI Database accession No. P24566.
GenBank accession No. M73544, downloaded Dec. 7, 2004.
GenBank accession No. S75820, downloaded Dec. 7, 2004.
GenBank accession No. D00334, downloaded Dec. 7, 2004.
GenBank accession No. D00392, downloaded Dec. 7, 2004.
GenBank accession No. D00393, downloaded Dec. 7, 2004.
GenBank accession No. D00394, downloaded Dec. 7, 2004.
GenBank accession No. D00395, downloaded Dec. 7, 2004.
GenBank accession No. D00396, downloaded Dec. 7, 2004.
GenBank accession No. D00397, downloaded Dec. 7, 2004.
GenBank accession No. D00736, downloaded Dec. 7, 2004.
GenBank accession No. D01042, downloaded Dec. 7, 2004.
GenBank accession No. M17213, downloaded Dec. 7, 2004.
GenBank accession No. AF013254, downloaded Dec. 7, 2004.

* cited by examiner

SEQUENCE LISTING

<160> NUMBER OF SEQ ID NOS: 54

<210> SEQ ID NO 1
<211> LENGTH: 15225
<212> TYPE: DNA
<213> ORGANISM: respiratory syncytial virus B 9320

<400> SEQUENCE: 1
acgcgaaaaa atgcgtacta caaacttgca cattcgaaaa aaatggggca aataagaatt 60
tgataagtgt tatttaagtc taaccttttc aatcagaaat ggggtgcaat tcattgagca 120
tgataaaggt tagattacaa aatttatttg acaatgacga agtagcattg ttaaaaataa 180
catgttatac tgacaaatta attcttctga ccaatgcatt agccaaagca gcaatacata 240
caattaaatt aaacggcata gtttttatac atgttataac aagcagtgaa gtgtgccctg 300
ataacaatat tgtagtgaaa tctaacttta caacaatgcc aatattacaa aacggaggat 360
acatatggga attgattgag ttgacacact gctctcaatt aaatggtcta atggatgata 420
attgtgaaat caaatttttct aaaagactaa gtgactcagt aatgactgat tatatgaatc 480
aaatatctga tttacttggg cttgatctca attcatgaat tgtgtttagt ctaattcaat 540
agacatgtgt ttattaccat tttagttaat ataaaaactc atcaaagaga aatggggcaa 600
ataaactcac ctaatcagtc aaatcatgag cactacaaat aacaacacta ctatgcaaag 660
attgatgatc acagacatga gacccctgtc gatggaatca ataataacat ctctcaccaa 720
agaaatcata acacacaaat tcatatactt gataaacaat gaatgtattg taagaaaact 780
tgatgaaaga caagctacat tcacattcct agtcaattat gagatgaagc tactacacaa 840
agtagggagt accaaatata agaaatacac tgaatataat acaaaatatg gcactttccc 900
tatgcctata tttatcaatc atggcgggtt tctagaatgt attggcatta agcctacaaa 960
acacactcct ataatataca aatatgacct caacccgtaa attccaacaa aaaactaacc 1020
catccaaact aagctattcc ttaaataaca gtgctcaaca gttaagaagg ggctaatcca 1080
ttttagtaat taaaaataaa ggtaaagcca ataacataaa ttggggcaaa tacaaagatg 1140
gctcttagca aagtcaagtt aaatgataca ttaaataagg atcagctgct gtcatctagc 1200
aaatacacta ttcaacgtag tacaggagat aatattgaca ctcccaatta tgatgtgcaa 1260
aaacacttaa acaaactatg tggtatgcta ttaatcactg aagatgcaaa tcataaattc 1320
acaggattaa taggtatgtt atatgctatg tccaggttag gaagggaaga cactataaag 1380
atacttaaag atgctggata tcatgttaaa gctaatggag tagatataac aacatatcgt 1440
caagatataa atggaaagga aatgaaattc gaagtattaa cattatcaag cttgacatca 1500
gaaatacaag tcaatattga gatagaatct agaaagtcct acaaaaaaat gctaaaagag 1560
atgggagaag tggctccaga atataggcat gattctccag actgtgggat gataatactg 1620
tgtatagctg cacttgtaat aaccaaatta gcagcaggag atagatcagg tcttacagca 1680
gtaattagga gggcaaacaa tgtcttaaaa aacgaaataa aacgctacaa gggcctcata 1740
ccaaaggata tagctaacag tttttatgaa gtgtttgaaa aacaccctca tcttatagat 1800
gtttttgtgc actttggcat tgcacaatca tccacaagag gggtagtag agttgaagga 1860 atctttgcag gattatttat gaatgcctat ggttcagggc aagtaatgct aagatgggga 1920
gttttagcca aatctgtaaa aaatatcatg ctaggacatg ctagtgtcca ggcagaaatg 1980
gagcaagttg tggaagtcta tgagtatgca cagaagttgg gaggagaagc tggattctac 2040

-continued

```
catatattga acaatccaaa agcatcattg ctgtcattaa ctcaatttcc taacttctca   2100
agtgtggtcc taggcaatgc agcaggtcta ggcataatgg gagagtatag aggtacacca   2160
agaaaccagg atctttatga tgcagccaaa gcatatgcag agcaactcaa agaaaatgga   2220
gtaataaact acagtgtatt agacttaaca gcagaagaat tggaggccat aaagcatcaa   2280
ctcaacccca aagaagatga tgtagagctc taagttaaca aaaaatacgg ggcaaataag   2340
tcaacatgga gaagtttgca cctgaatttc atggagaaga tgcaaataac aaagctacca   2400
aattcctaga atcaataaag ggcaagttcg catcatccaa agatcctaag aagaaagata   2460
gcataaatatc tgttaactca atagatatag aagtaactaa agagagcccg ataacatctg   2520
gcaccaacat caacaatcca acaagtgaag ctgacagtac cccagaagcc aaaaccaact   2580
acccaagaaa acccctagta agcttcaaag aagatctcac cccaagtgac aaccccttt    2640
ctaagttgta caaagaaaca atagaaacat ttgataacaa tgaagaagaa tctagctact   2700
catatgaaga aataaatgat caaacaaatg acaacattac agcaagacta gatagaattg   2760
atgaaaaatt aagtgaaata ttaggaatgc tccatacatt agtagttgca agtgcaggac   2820
ccacttcagc tcgcgatgga ataagagatg ctatggttgg tctaagagaa gaaatgatag   2880
aaaaaataag agcggaagca ttaatgacca atgataggtt agaggctatg gcaagactta   2940
ggaatgagga aagcgaaaaa atggcaaaag acacctcaga tgaagtgtct ctcaatccaa   3000
cttccaaaaa attgagtgac ttgctggaag acaacgatag tgacaatgat ctatcacttg   3060
atgatttttg atcagtgatc aactcactca gcaatcaaca acatcaataa gacagacatc   3120
aatccattga atcaactgcc agaccgaaca aacaaacgtt catcagcaga accaccaacc   3180
aatcaatcaa ccaattgatc aatcagcaac ctaacaaaat taacaatata gtaacaaaaa   3240
aagaacaaga tggggcaaat atggaaacat acgtgaacaa gcttcacgaa ggctccacat   3300
acacagcagc tgttcagtac aatgttctag aaaaagatga tgatcctgca tcactaacaa   3360
tatgggtgcc tatgttccag tcatctgtgc cagcagactt gctcataaaa gaacttgcaa   3420
gcatcaacat actagtgaag cagatctcta cgcccaaagg accttcacta cgagtcacga   3480
tcaactcaag aagcgctgtg ctggcacaaa tgcccagtaa ttttatcata agtgcaaatg   3540
tatcattaga tgaaagaagc aaattagcat atgatgtaac tacaccttgt gaaatcaaag   3600
catgcagtct aacatgctta aaagtaaaaa gtatgctaac tacagtcaaa gatcttacca   3660
tgaaaacatt caaccccact catgagatta ttgctctatg tgaatttgaa aatattatga   3720
catcaaaaag agtaataata ccaacctatc taagatcaat tagtgtcaaa aacaaggacc   3780
tgaactcact agaaaatata gcaaccaccg aattcaaaaa tgctatcacc aatgcgaaaa   3840
ttattcccta tgcaggatta gtattagtta tcacagttac tgacaataaa ggagcattca   3900
aatatatcaa gccacagagt caatttatag tagatcttgg agcctaccta gaaaaagaga   3960
gcatatatta tgtgactaca aattggaagc atacagctac acgtttttca atcaaaccac   4020
tagaggatta aacttaatta tcaacgctaa atgacaggtc cacatatatc ctcaaactac   4080
acactatatc caaacatcat gaacatctac actacacact tcatcacaca aaccaatccc   4140
acttaaaatc caaaatcact tccagccact atctgctaga cctagagtgc gaataggtaa   4200
ataaaaccaa aatatggggt aaatagacat tagttagagt tcaatcaatc tcaacaacca   4260
tttatactgc taattcaata catatactat aaatttcaaa atgggaaata catccatcac   4320
aatagaattc actagcaaat tttggcctta ttttacacta atacatatga tcttaactct   4380
```

-continued

```
aatctcttta ctaattataa tcactattat gattgcaata ctaaataagc taagtgaaca   4440
taaaacattc tgtaacaaaa ctcttgaact aggacagatg tatcaaatca acacatagtg   4500
ttctaccatc atgctgtgtc aaattataat cctgtatatg taaacaaaca aatccaatct   4560
tctcacagag tcatggtggc gcaaagccac gccaactatc atggtagcat agagtagtta   4620
tttaaaaatt aacataatga tgaattatta gtatgggatc aaaaacaaca ttggggcaaa   4680
tgcaaccatg tccaaacaca agagtcaacg cactgccagg actctagaaa agacctggga   4740
tactcttaat catctaattg taatatcctc ttgtttatac agactaaacc taaaatctat   4800
agcacaaata gcactatcag ttttggcaat gataatctca acctctctca taattgcagc   4860
cataatattc atcatctctg ccaatcacaa agttacacta acaacggtta cagttcaaac   4920
aataaaaaac cacactgaaa aaaacatcac cacctacctt actcaagtct caccagaaag   4980
ggttagctca tccatacaac ctacaaccac atcaccaatc cacacaaatt cagctacaat   5040
atcaccaaat acaaaatcag aaacacacca tacaacaaca caagccaaaa gcagaatcac   5100
cacttcaaca cagaccaaca agccaagcac aaaatcacgt tcaaaaaatc caccaaaaaa   5160
accaaaagat gattaccatt ttgaagtgtt caattttgtt ccctgtagta tatgtggcaa   5220
caatcaactt tgcaaatcca tctgcaaaac aataccaagc aacaaaccaa agaaaaaacc   5280
aaccatcaaa cccacaaaca aaccaaccgt caaaaccaca aacaaaagag acccaaaaac   5340
accagccaaa atgatgaaaa aagaaaccac caccaaccca acaaaaaaac caaccctcaa   5400
gaccacagaa ggagacacca gcacctcaca atccactgtg ctcgacacaa ccacatcaaa   5460
acacacaatc caacagcaat ccctccactc aatcacctcc gaaaacacac ccaactccac   5520
acaaataccc acagcaaccg aggcctccac atcaaattct acttaaaaaa cctagtcaca   5580
tgcttagtta ttcaaaaact acatcttagc agagaaccgt gatctatcaa gcaagaatga   5640
aattaaacct ggggcaaata accatggagt tgctgatcca caggtcaagt gcaatcttcc   5700
taactcttgc tattaatgca ttgtacctca cctcaagtca gaacataact gaggagtttt   5760
accaatcgac atgtagtgca gttagcagag gttattttag tgctttaaga acaggttggt   5820
ataccagtgt tataacaata gaattaagta atataaaaga aaccaaatgc aatggaactg   5880
acactaaagt aaaacttata aaacaagaat tagataagta taagaatgca gtaacagaat   5940
tacagctact tacgcaaaac acgccagctg ccaacaaccg ggccagaaga gaagcaccac   6000
agtacatgaa ctacacaatc aataccacta aaaacctaaa cgtatcaata agcaagaaga   6060
ggaaacgaag atttctggga ttcttgttag gtgtaggatc tgcaatagca agtggtatag   6120
ctgtatccaa agttctacac cttgaaggag aagtgaacaa aatcaaaaat gctttgttgt   6180
ctacaaacaa agctgtagtc agtctatcaa atggggtcag tgttttaacc agcaaagtgt   6240
tagatctcaa gagttacata aataaccaat tattacccat agtaaatcaa cagagctgtc   6300
gcatctccaa cattgaaaca gttatagaat tccagcagaa gaacagcaga ttgttggaaa   6360
tcaccagaga atttagtgtc aatgcaggtg taacaacacc tttaagcact tacatgttaa   6420
caaacagtga gttactatca ttgatcaatg atatgcctat aacaaatgat cagaaaaaat   6480
taatgtcaag caatgtccag atagtaaggc aacaaagtta ttctatcatg tctataataa   6540
aggaagaagt ccttgcatat gttgtacagc tacctatcta tggtgtaata gatacacctt   6600
gctggaaatt acacacatca cctctatgca ccaccaacat caaagaagga tcaaatattt   6660
gtttaacaag gactgataga ggatggtatt gtgataatgc aggatcagta tccttcttcc   6720
cacaggctga cacttgcaaa gtgcagtcca atcgagtatt ttgtgacact atgaacagtt   6780
```

-continued tgacattacc aagtgaagtc agcctttgta acactgacat attcaattcc aagtatgact 6840
gcaaaatcat gacttcaaaa acagacataa gcagctcagt aattacttct cttggagcta 6900
tagtgtcatg ctatggtaaa actaaatgca ctgcatccaa taaaaatcgt gggattataa 6960
agacattttc taatggttgt gactatgtgt caaacaaagg agtagatact gtgtcagtgg 7020
gcaacacttt atactatgta aacaagctgg aaggcaaaaa cctttatgta aaaggggaac 7080
ctataataaa ttactatgat cctctagtgt ttccttctga tgagtttgat gcatcaatat 7140
ctcaagtcaa tgaaaaaatc aatcaaagtt tagcttttat acgtagatct gatgaattac 7200
tacataatgt aaatactggc aaatctacta caaatattat gataaccaca atcattatag 7260
taatcattgt agtattgtta tcattaatag ctattggttt actgttgtat tgcaaagcta 7320
aaaacacacc agttacacta agcaaagacc aactaagtgg aatcaacaat attgcattca 7380
gcaaatagac aaaaaaccac ttgatcatgt ttcaacaaca atctgctgac caccaatccc 7440
aaatcaactt aacaacaaat atttcaacat catagcacag gctgaatcat ttcctcacat 7500
catgctacct acacaactaa gctagatcct taactcatag ttacataaaa acctcaagta 7560
tcacaatcaa acactaaatc gacacatcat tcacaaaatt aacaactggg gcaaatatgt 7620
cgcgaagaaa tccttgtaaa tttgagatta gaggtcattg cttgaatggt agaagatgtc 7680
actacagtca taattatttt gaatggcctc ctcatgcatt actagtgagg caaaacttca 7740
tgttaaacaa gatacttaag tcaatggaca aaagcataga cactttgtcg gaaataagtg 7800
gagctgctga actggataga acagaagaat atgctcttgg tatagttgga gtgctagaga 7860
gttacatagg atctataaac aacataacaa aacaatcagc atgtgttgct atgagtaaac 7920
ttcttattga gatcaacagt gatgacatta aaaaactgag agataatgaa gaacccaatt 7980
cacctaagat aagagtgtac aatactgtta tatcatacat tgagagcaat agaaaaaaca 8040
acaagcaaac catccatctg ctcaaaagac taccagcaga tgtgctgaag aagacaataa 8100
agaacacatt agatatccac aaaagcataa ccataagcaa cccaaaagag tcaaccgtga 8160
atgatcaaaa tgaccaaacc aaaaataatg atattaccgg ataaatatcc ttgtagtata 8220
tcatccatac tgatttcaag tgaaagcatg gttgccacat tcaatcacaa aaacatatta 8280
caatttaacc ataaccattt ggataaccac cagtgtttat taaatcatat atttgatgaa 8340
attcattgga cacctaaaaa cttattagat accactcaac aatttctcca acatcttaac 8400
atccctgaag atatatatac agtatatata ttagtgtcat aatgcttgac cataacgatc 8460
ttatatcatc caaccataaa actatcataa taaggttatg ggacaaaatg gatcccatta 8520
ttaatggaaa ctctgctaat gtgtatctaa ctgatagtta tctaaaaggt gttatctctt 8580
tttcagaatg taatgcttta gggagttacc tttttaacgg cccttatctt aaaaatgatt 8640
acactaactt aattagtaga caaagcccac tactagagca tatgaatcta aaaaaactaa 8700
ctataacaca gtcattaata tctagatatc ataaaggtga actgaaatta gaagaaccaa 8760
cttatttcca gtcattactt atgacatata aaagtatgtc ctcgtctgaa caaattgcta 8820
caactaactt acttaaaaaa ataatacgaa gagctataga aataagtgat gtaaaggtgt 8880
acgccatctt gaataaacta ggactaaagg aaaaggacag agttaagccc aacaataatt 8940
caggtgatga aaactcagtt cttacaacca taattaaaga tgatatactt tcggctgtgg 9000
aaaacaatca atcatataca aattcagaca aaaatcactc agtgaaccaa aatatcacta 9060
tcaaaacaac actcttgaaa aaattgatgt gttcaatgca acatcctcca tcatggttaa 9120

-continued

```
tacactggtt caatttatat acaaaattaa ataacatatt aacacaatat cgatcaaatg   9180
aggtaaaaag tcatgggttt atattaatag ataatcaaac tttaagtggt tttcagttta   9240
ttttaaatca atatggttgt attgtttatc ataaaggact taaaaaaatc acaactacta   9300
cttacaatca atttttgaca tggaaagaca tcagccttag cagattaaat gtttgcttaa   9360
ttacttggat aagtaattgt ttaaatacat taaataaaag cttagggctg agatgtggat   9420
tcaataatgt tgtgttatca caattatttc tttatggaga ttgtatactg aaattatttc   9480
ataatgaagg cttctacata ataaaagaag tagagggatt tattatgtct ttaattctaa   9540
acataacaga agaagatcaa tttaggacac gattttataa cagcatgcta aataacatca   9600
cagatgcagc tattaaggct caaaaaaacc tactatcaag agtatgtcac actttattgg   9660
acaagacagt gtctgataat atcataaatg gtaaatggat aatcctatta agtaaatttc   9720
ttaaattgat taagcttgca ggtgataata atctcaataa cttgagtgag ctatattttc   9780
tcttcagaat ctttggacat ccaatggtcg atgaaagaca agcaatggat gctgtaagaa   9840
ttaactgtaa tgaaactaag ttctacttat taagtagtct aagtacgtta agaggtgctt   9900
tcatttatag aatcataaaa gggtttgtaa atacctacaa cagatggccc actttaagga   9960
atgctattgt tctacctcta agatggttga actattataa acttaatact tatccatctc  10020
tacttgaaat cacagaaaat gatttgatta ttttatcagg attgaggttc tatcgtgagt  10080
ttcatctgcc taaaaaagtg gatcttgaaa tgataataaa tgacaaagcc atttcacctc  10140
caaaagatct aatatggact agttttccca gaaattacat gccatcacat atacaaaatt  10200
atatagaaca tgaaaagttg aagttctctg aaagcgacag atcaagaaga gtactagagt  10260
attacttgag agataataaa ttcaatgaat gcgatctata caattgtgtg gtcaatcaaa  10320
gctatctcaa caactctaac cacgtggtat cactaactgg taaagaaaga gagctcagtg  10380
taggtagaat gtttgctatg caaccaggta tgtttaggca aattcaaatc ttagcagaga  10440
aaatgatagc cgaaaatatt ttacaattct tccctgagag tttgacaaga tatggtgatc  10500
tagagcttca aaagatatta gaattaaaag caggaataag caacaaatca aatcgttata  10560
atgataacta caacaattat atcagtaaat gttctatcat tacagacctt agcaaattca  10620
atcaagcatt tagatatgaa acatcatgta tctgcagtga tgtattagat gaactgcatg  10680
gagtacaatc actgttctct tggttgcatt taacaatacc tcttgtcaca ataaatatgta  10740
catatagaca tgcacctcct ttcataaagg atcatgttgt taatctgaat gaagttgatg  10800
aacaaagtgg attatacaga tatcatatgg gtggtattga gggctggtgt caaaaactgt  10860
ggaccattga agctatatca ttattagatc taatatccct caaagggaaa ttctctatca  10920
cagctctaat aaatggtgat aatcagtcaa ttgatataag taaaccagtt agacttatag  10980
agggtcagac ccatgctcaa gcagattatt tgttagcatt aaatagcctt aaattgctat  11040
ataaagagta tgcaggcata ggccataagc tcaagggaac agaaacctat atatcccgag  11100
atatgcaatt catgagcaaa acaatccagc acaatggagt gtactatcca gccagtatca  11160
aaaaagtcct gagagtaggt ccatggataa atacaatact tgatgatttt aaagttagtt  11220
tagaatctat aggcagctta acacaggagt tagaatacag aggagaaagc ttattatgca  11280
gtttaatatt tagaaacatt tggttataca atcaaattgc tttgcaactc cgaaatcatg  11340
cattatgtca caataagcta tatttagata tattgaaagt attaaaacac ttaaaaactt  11400
tttttaatct tgatagtatc gatatggcat tatcattgta tatgaatttg cctatgctgt  11460
ttggtggtgg tgatcctaat ttgttatatc gaagctttta tagaagaact ccagacttcc  11520
```

-continued

```
ttacagaagc tatagtacat tcagtgtttg tgttgagcta ttatactggt cacgatttac  11580
aagataagct ccaggatctt ccagatgata gactgaacaa attcttgaca tgtatcatca  11640
catttgataa aaatcccaat gccgagtttg taacattaat gagggatcca caggctttag  11700
ggtctgaaag gcaagctaaa attactagtg agattaatag attagcagta acggaagtct  11760
taagtatagc tccaaacaaa atattttcta aaagtgcaca acattatact accactgaga  11820
ttgatctaaa tgatattatg caaaatatag aaccaactta ccctcatgga ttaagagttg  11880
tttatgaaag tttacctttt tataaagcag aaaaaatagt taatcttata tcaggaacaa  11940
aatccataac taatatactt gaaaaaacat cagcaataga tacaactgat attaataggg  12000
ctactgatat gatgaggaaa aatataactt tacttataag gatacttcca ctagattgta  12060
acaaagacaa aagagagtta ttaagtttag aaaatcttag tataactgaa ttaagcaagt  12120
atgtaagaga aagatcttgg tcgttatcca atatagtagg agtaacatcg ccaagtatta  12180
tgttcacaat ggacattaaa tatacaacta gcactatagc cagtggtata attatagaaa  12240
aatataatgt taatagttta actcgtggtg aaagaggacc tactaagcca tgggtaggtt  12300
catctacgca ggagaaaaaa acaatgccag tgtataatag acaagtttta accaaaaagc  12360
aaagagacca aatagattta ttagcaaaat tagactgggt atatgcatcc atagacaaca  12420
aagatgaatt catggaagaa ctgagtactg gaacacttgg attgtcatat gaaaaagcca  12480
aaaaattgtt tccacaatat ctaagtgtca attatttaca ccgcttaaca gtcagtagta  12540
ggccatgtga attccctgca tcaataccag cttatagaac aacaaattat catttcgata  12600
ctagtcctat caatcatgta ttaacagaaa agtatggaga tgaagatatc gacatagtgt  12660
ttcaaaattg cataagtttt ggtcttagcc taatgtcggt tgtggaacaa ttcacaaaca  12720
tatgtcctaa tagaattatt ctcataccga agctgaatga gatacatttg atgaaacctc  12780
ctatatttac aggagatgtt gatatcatca aattgaagca agtgatacaa aaacagcaca  12840
tgttcctacc agataaaata agtttaaccc aatatgtaga attattccta agtaacaaag  12900
cacttaaatc tggatctcac atcaactcta atttaatatt agtacataaa atgtctgatt  12960
attttcataa tgattatatt ttaagtacta atttagctgg acattggatt ctgattattc  13020
aacttatgaa agattcaaaa ggtatttttg aaaaagattg gggagagggg tatataactg  13080
atcatatgtt cattaatttg aatgttttct ttaatgctta taagacttat ttgctatgtt  13140
ttcataaagg ttatggtaaa gcaaaattag aatgtgatat gaacacttca gatcttcttt  13200
gtgttttgga gttaatagac agtagctact ggaaatctat gtctaaagtt ttcctagaac  13260
agaaagtcat aaaatacata gtcaatcaag acacaagttt gcatagaata aaaggttgtc  13320
atagttttaa gttgtggttt ttaaaacgcc ttaataatgc taaatttacc gtatgccctt  13380
gggttgttaa catagattat cacccaacac acatgaaagc tatattatct tacatagatt  13440
tagttagaat ggggttaata aatgtagata aattaaccat taaaaataaa aacaaattca  13500
atgatgaatt ttacacatca aatctctttt atattagtta taacttttca gacaacactc  13560
atttgctaac aaaacaaata agaattgcta attcagaatt agaaaataat tataacaaac  13620
tatatcaccc aaccccagaa actttagaaa atatgtcatt aattcctgtt aaaagtaaca  13680
atagtaacaa acctaaatct tgtataagtg gaaataccga atctatgatg acgtcaacat  13740
tctccaataa aatgcatatt aaatcttcca ctgttaccac aagattaaac tatagcaaac  13800
aagacttgta caatttattt ccaattgttg tgatagacag gattatagat cattcaggca  13860
```

-continued

```
atacagcaaa atccaaccaa ctttacacca ccacttcaca tcagacatct ttagtaagga  13920

atagtgcatc actttattgc atgcttcctt ggcatcatgt caatagattt aactttgtat  13980

ttagttccac aggatgcaag atcagtatag agtatatttt aaaagatctt aagattaagg  14040

accccagttg tatagcattc ataggtgaag gagctggtaa cttattatta cgtacggtag  14100

tagaacttca tccagacata agatacattt acagaagttt aaaagattgc aatgatcata  14160

gtttacctat tgaatttcta aggttataca acgggcatat aaacatagat tatggtgaga  14220

atttaaccat tcctgctaca gatgcaacta ataacattca ttggtcttat ttacatataa  14280

aatttgcaga acctattagc atctttgtct gcgatgctga attacctgtt acagccaatt  14340

ggagtaaaat tataattgaa tggagtaagc atgtaagaaa gtgcaagtac tgttcctctg  14400

taaatagatg cattttaatt gcaaaatatc atgctcaaga tgatattgat ttcaaattag  14460

ataacattac tatattaaaa acttatgtgt gcctaggtag caagttaaaa ggatctgaag  14520

tttacttagt ccttacaata ggcccttcaa atatacttcc tgtttttaat gttgtgcaaa  14580

atgctaaatt gattctttca agaactaaaa atttcattat gcctaaaaaa actgacaaag  14640

aatctatcga tgcaaatatt aaaagcttaa tacctttcct ttgttaccct ataacaaaaa  14700

aaggaattaa gacttcattg tcaaaattga agagtgtagt taatggagat atattatcat  14760

attctatagc tggacgtaat gaagtattca gcaacaagct tataaaccac aagcatatga  14820

atatcctaaa atggctagat catgttttaa actttagatc aactgaactt aattacaatc  14880

atttatatat gatagagtcc acatatcctt acttaagtga attgttaaat agtttaacaa  14940

ccaatgagct caaaaagctg attaaaatta caggtagtgt actatacaac cttcccaatg  15000

aacagtaact taaaatatca ttaacaagtt tggtcaaatt tagatgctaa cacatcatta  15060

tattatagtt attaaaaaat atgcaaactt ttcaataatt tagcatattg attccaaaat  15120

tatctatttt ggtcttaagg ggttaaataa aaatctaaaa ctaacaatta tacatgtgca  15180

tttacaacac aacgagacat tagtttttga cacttttttt ctcgt                  15225
```

<210> SEQ ID NO 2
<211> LENGTH: 139
<212> TYPE: PRT
<213> ORGANISM: respiratory syncytial virus B 9320

<400> SEQUENCE: 2

```
Met Gly Cys Asn Ser Leu Ser Met Ile Lys Val Arg Leu Gln Asn Leu
1               5                   10                  15

Phe Asp Asn Asp Glu Val Ala Leu Leu Lys Ile Thr Cys Tyr Thr Asp
            20                  25                  30

Lys Leu Ile Leu Leu Thr Asn Ala Leu Ala Lys Ala Ala Ile His Thr
        35                  40                  45

Ile Lys Leu Asn Gly Ile Val Phe Ile His Val Ile Thr Ser Ser Glu
    50                  55                  60

Val Cys Pro Asp Asn Asn Ile Val Val Lys Ser Asn Phe Thr Thr Met
65                  70                  75                  80

Pro Ile Leu Gln Asn Gly Gly Tyr Ile Trp Glu Leu Ile Glu Leu Thr
                85                  90                  95

His Cys Ser Gln Leu Asn Gly Leu Met Asp Asp Asn Cys Glu Ile Lys
            100                 105                 110

Phe Ser Lys Arg Leu Ser Asp Ser Val Met Thr Asp Tyr Met Asn Gln
        115                 120                 125

Ile Ser Asp Leu Leu Gly Leu Asp Leu Asn Ser
```

-continued 130 135

<210> SEQ ID NO 3
<211> LENGTH: 124
<212> TYPE: PRT
<213> ORGANISM: respiratory syncytial virus B 9320

<400> SEQUENCE: 3

Met Ser Thr Thr Asn Asn Asn Thr Thr Met Gln Arg Leu Met Ile Thr
1 5 10 15

Asp Met Arg Pro Leu Ser Met Glu Ser Ile Ile Thr Ser Leu Thr Lys
20 25 30

Glu Ile Ile Thr His Lys Phe Ile Tyr Leu Ile Asn Asn Glu Cys Ile
35 40 45

Val Arg Lys Leu Asp Glu Arg Gln Ala Thr Phe Thr Phe Leu Val Asn
50 55 60

Tyr Glu Met Lys Leu Leu His Lys Val Gly Ser Thr Lys Tyr Lys Lys
65 70 75 80

Tyr Thr Glu Tyr Asn Thr Lys Tyr Gly Thr Phe Pro Met Pro Ile Phe
85 90 95

Ile Asn His Gly Gly Phe Leu Glu Cys Ile Gly Ile Lys Pro Thr Lys
100 105 110

His Thr Pro Ile Ile Tyr Lys Tyr Asp Leu Asn Pro
115 120

<210> SEQ ID NO 4
<211> LENGTH: 391
<212> TYPE: PRT
<213> ORGANISM: respiratory syncytial virus B 9320

<400> SEQUENCE: 4

Met Ala Leu Ser Lys Val Lys Leu Asn Asp Thr Leu Asn Lys Asp Gln
1 5 10 15

Leu Leu Ser Ser Ser Lys Tyr Thr Ile Gln Arg Ser Thr Gly Asp Asn
20 25 30

Ile Asp Thr Pro Asn Tyr Asp Val Gln Lys His Leu Asn Lys Leu Cys
35 40 45

Gly Met Leu Leu Ile Thr Glu Asp Ala Asn His Lys Phe Thr Gly Leu
50 55 60

Ile Gly Met Leu Tyr Ala Met Ser Arg Leu Gly Arg Glu Asp Thr Ile
65 70 75 80

Lys Ile Leu Lys Asp Ala Gly Tyr His Val Lys Ala Asn Gly Val Asp
85 90 95

Ile Thr Thr Tyr Arg Gln Asp Ile Asn Gly Lys Glu Met Lys Phe Glu
100 105 110

Val Leu Thr Leu Ser Ser Leu Thr Ser Glu Ile Gln Val Asn Ile Glu
115 120 125

Ile Glu Ser Arg Lys Ser Tyr Lys Lys Met Leu Lys Glu Met Gly Glu
130 135 140

Val Ala Pro Glu Tyr Arg His Asp Ser Pro Asp Cys Gly Met Ile Ile
145 150 155 160

Leu Cys Ile Ala Ala Leu Val Ile Thr Lys Leu Ala Ala Gly Asp Arg
165 170 175

Ser Gly Leu Thr Ala Val Ile Arg Arg Ala Asn Asn Val Leu Lys Asn
180 185 190

Glu Ile Lys Arg Tyr Lys Gly Leu Ile Pro Lys Asp Ile Ala Asn Ser

-continued

```
        195                 200                 205

Phe Tyr Glu Val Phe Glu Lys His Pro His Leu Ile Asp Val Phe Val
    210                 215                 220

His Phe Gly Ile Ala Gln Ser Ser Thr Arg Gly Gly Ser Arg Val Glu
225                 230                 235                 240

Gly Ile Phe Ala Gly Leu Phe Met Asn Ala Tyr Gly Ser Gly Gln Val
                245                 250                 255

Met Leu Arg Trp Gly Val Leu Ala Lys Ser Val Lys Asn Ile Met Leu
            260                 265                 270

Gly His Ala Ser Val Gln Ala Glu Met Glu Gln Val Val Glu Val Tyr
        275                 280                 285

Glu Tyr Ala Gln Lys Leu Gly Gly Glu Ala Gly Phe Tyr His Ile Leu
    290                 295                 300

Asn Asn Pro Lys Ala Ser Leu Leu Ser Leu Thr Gln Phe Pro Asn Phe
305                 310                 315                 320

Ser Ser Val Val Leu Gly Asn Ala Ala Gly Leu Gly Ile Met Gly Glu
                325                 330                 335

Tyr Arg Gly Thr Pro Arg Asn Gln Asp Leu Tyr Asp Ala Ala Lys Ala
            340                 345                 350

Tyr Ala Glu Gln Leu Lys Glu Asn Gly Val Ile Asn Tyr Ser Val Leu
        355                 360                 365

Asp Leu Thr Ala Glu Glu Leu Glu Ala Ile Lys His Gln Leu Asn Pro
    370                 375                 380

Lys Glu Asp Asp Val Glu Leu
385                 390


<210> SEQ ID NO 5
<211> LENGTH: 241
<212> TYPE: PRT
<213> ORGANISM: respiratory syncytial virus B 9320

<400> SEQUENCE: 5

Met Glu Lys Phe Ala Pro Glu Phe His Gly Glu Asp Ala Asn Asn Lys
1               5                   10                  15

Ala Thr Lys Phe Leu Glu Ser Ile Lys Gly Lys Phe Ala Ser Ser Lys
            20                  25                  30

Asp Pro Lys Lys Lys Asp Ser Ile Ile Ser Val Asn Ser Ile Asp Ile
        35                  40                  45

Glu Val Thr Lys Glu Ser Pro Ile Thr Ser Gly Thr Asn Ile Asn Asn
    50                  55                  60

Pro Thr Ser Glu Ala Asp Ser Thr Pro Glu Ala Lys Thr Asn Tyr Pro
65                  70                  75                  80

Arg Lys Pro Leu Val Ser Phe Lys Glu Asp Leu Thr Pro Ser Asp Asn
                85                  90                  95

Pro Phe Ser Lys Leu Tyr Lys Glu Thr Ile Glu Thr Phe Asp Asn Asn
            100                 105                 110

Glu Glu Glu Ser Ser Tyr Ser Tyr Glu Glu Ile Asn Asp Gln Thr Asn
        115                 120                 125

Asp Asn Ile Thr Ala Arg Leu Asp Arg Ile Asp Glu Lys Leu Ser Glu
    130                 135                 140

Ile Leu Gly Met Leu His Thr Leu Val Val Ala Ser Ala Gly Pro Thr
145                 150                 155                 160

Ser Ala Arg Asp Gly Ile Arg Asp Ala Met Val Gly Leu Arg Glu Glu
                165                 170                 175
```

-continued

Met Ile Glu Lys Ile Arg Ala Glu Ala Leu Met Thr Asn Asp Arg Leu
180 185 190

Glu Ala Met Ala Arg Leu Arg Asn Glu Glu Ser Glu Lys Met Ala Lys
195 200 205

Asp Thr Ser Asp Glu Val Ser Leu Asn Pro Thr Ser Lys Lys Leu Ser
210 215 220

Asp Leu Leu Glu Asp Asn Asp Ser Asp Asn Asp Leu Ser Leu Asp Asp
225 230 235 240

Phe

<210> SEQ ID NO 6
<211> LENGTH: 256
<212> TYPE: PRT
<213> ORGANISM: respiratory syncytial virus B 9320

<400> SEQUENCE: 6

Met Glu Thr Tyr Val Asn Lys Leu His Glu Gly Ser Thr Tyr Thr Ala
1 5 10 15

Ala Val Gln Tyr Asn Val Leu Glu Lys Asp Asp Asp Pro Ala Ser Leu
20 25 30

Thr Ile Trp Val Pro Met Phe Gln Ser Ser Val Pro Ala Asp Leu Leu
35 40 45

Ile Lys Glu Leu Ala Ser Ile Asn Ile Leu Val Lys Gln Ile Ser Thr
50 55 60

Pro Lys Gly Pro Ser Leu Arg Val Thr Ile Asn Ser Arg Ser Ala Val
65 70 75 80

Leu Ala Gln Met Pro Ser Asn Phe Ile Ile Ser Ala Asn Val Ser Leu
85 90 95

Asp Glu Arg Ser Lys Leu Ala Tyr Asp Val Thr Thr Pro Cys Glu Ile
100 105 110

Lys Ala Cys Ser Leu Thr Cys Leu Lys Val Lys Ser Met Leu Thr Thr
115 120 125

Val Lys Asp Leu Thr Met Lys Thr Phe Asn Pro Thr His Glu Ile Ile
130 135 140

Ala Leu Cys Glu Phe Glu Asn Ile Met Thr Ser Lys Arg Val Ile Ile
145 150 155 160

Pro Thr Tyr Leu Arg Ser Ile Ser Val Lys Asn Lys Asp Leu Asn Ser
165 170 175

Leu Glu Asn Ile Ala Thr Thr Glu Phe Lys Asn Ala Ile Thr Asn Ala
180 185 190

Lys Ile Ile Pro Tyr Ala Gly Leu Val Leu Val Ile Thr Val Thr Asp
195 200 205

Asn Lys Gly Ala Phe Lys Tyr Ile Lys Pro Gln Ser Gln Phe Ile Val
210 215 220

Asp Leu Gly Ala Tyr Leu Glu Lys Glu Ser Ile Tyr Tyr Val Thr Thr
225 230 235 240

Asn Trp Lys His Thr Ala Thr Arg Phe Ser Ile Lys Pro Leu Glu Asp
245 250 255

<210> SEQ ID NO 7
<211> LENGTH: 65
<212> TYPE: PRT
<213> ORGANISM: respiratory syncytial virus B 9320

<400> SEQUENCE: 7

Met Gly Asn Thr Ser Ile Thr Ile Glu Phe Thr Ser Lys Phe Trp Pro

-continued

```
1               5                   10                  15

Tyr Phe Thr Leu Ile His Met Ile Leu Thr Leu Ile Ser Leu Leu Ile
            20                  25                  30

Ile Ile Thr Ile Met Ile Ala Ile Leu Asn Lys Leu Ser Glu His Lys
        35                  40                  45

Thr Phe Cys Asn Lys Thr Leu Glu Leu Gly Gln Met Tyr Gln Ile Asn
    50                  55                  60

Thr
65


<210> SEQ ID NO 8
<211> LENGTH: 574
<212> TYPE: PRT
<213> ORGANISM: respiratory syncytial virus B 9320

<400> SEQUENCE: 8

Met Glu Leu Leu Ile His Arg Ser Ser Ala Ile Phe Leu Thr Leu Ala
1               5                   10                  15

Ile Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Thr Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Ser Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300
```

-continued

```
Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Ile Met Ile Thr
        515                 520                 525

Thr Ile Ile Ile Val Ile Ile Val Val Leu Leu Ser Leu Ile Ala Ile
    530                 535                 540

Gly Leu Leu Leu Tyr Cys Lys Ala Lys Asn Thr Pro Val Thr Leu Ser
545                 550                 555                 560

Lys Asp Gln Leu Ser Gly Ile Asn Asn Ile Ala Phe Ser Lys
                565                 570


<210> SEQ ID NO 9
<211> LENGTH: 195
<212> TYPE: PRT
<213> ORGANISM: respiratory syncytial virus B 9320

<400> SEQUENCE: 9

Met Ser Arg Arg Asn Pro Cys Lys Phe Glu Ile Arg Gly His Cys Leu
1               5                   10                  15

Asn Gly Arg Arg Cys His Tyr Ser His Asn Tyr Phe Glu Trp Pro Pro
            20                  25                  30

His Ala Leu Leu Val Arg Gln Asn Phe Met Leu Asn Lys Ile Leu Lys
        35                  40                  45

Ser Met Asp Lys Ser Ile Asp Thr Leu Ser Glu Ile Ser Gly Ala Ala
    50                  55                  60

Glu Leu Asp Arg Thr Glu Glu Tyr Ala Leu Gly Ile Val Gly Val Leu
65                  70                  75                  80

Glu Ser Tyr Ile Gly Ser Ile Asn Asn Ile Thr Lys Gln Ser Ala Cys
                85                  90                  95

Val Ala Met Ser Lys Leu Leu Ile Glu Ile Asn Ser Asp Asp Ile Lys
            100                 105                 110
```

-continued

```
Lys Leu Arg Asp Asn Glu Glu Pro Asn Ser Pro Lys Ile Arg Val Tyr
        115                 120                 125

Asn Thr Val Ile Ser Tyr Ile Glu Ser Asn Arg Lys Asn Asn Lys Gln
    130                 135                 140

Thr Ile His Leu Leu Lys Arg Leu Pro Ala Asp Val Leu Lys Lys Thr
145                 150                 155                 160

Ile Lys Asn Thr Leu Asp Ile His Lys Ser Ile Thr Ile Ser Asn Pro
                165                 170                 175

Lys Glu Ser Thr Val Asn Asp Gln Asn Asp Gln Thr Lys Asn Asn Asp
            180                 185                 190

Ile Thr Gly
        195


<210> SEQ ID NO 10
<211> LENGTH: 93
<212> TYPE: PRT
<213> ORGANISM: respiratory syncytial virus B 9320

<400> SEQUENCE: 10

Met Ile Lys Met Thr Lys Pro Lys Ile Met Ile Leu Pro Asp Lys Tyr
1               5                   10                  15

Pro Cys Ser Ile Ser Ser Ile Leu Ile Ser Ser Glu Ser Met Val Ala
            20                  25                  30

Thr Phe Asn His Lys Asn Ile Leu Gln Phe Asn His Asn His Leu Asp
        35                  40                  45

Asn His Gln Cys Leu Leu Asn His Ile Phe Asp Glu Ile His Trp Thr
    50                  55                  60

Pro Lys Asn Leu Leu Asp Thr Thr Gln Gln Phe Leu Gln His Leu Asn
65                  70                  75                  80

Ile Pro Glu Asp Ile Tyr Thr Val Tyr Ile Leu Val Ser
                85                  90


<210> SEQ ID NO 11
<211> LENGTH: 2166
<212> TYPE: PRT
<213> ORGANISM: respiratory syncytial virus B 9320

<400> SEQUENCE: 11

Met Asp Pro Ile Ile Asn Gly Asn Ser Ala Asn Val Tyr Leu Thr Asp
1               5                   10                  15

Ser Tyr Leu Lys Gly Val Ile Ser Phe Ser Glu Cys Asn Ala Leu Gly
            20                  25                  30

Ser Tyr Leu Phe Asn Gly Pro Tyr Leu Lys Asn Asp Tyr Thr Asn Leu
        35                  40                  45

Ile Ser Arg Gln Ser Pro Leu Leu Glu His Met Asn Leu Lys Lys Leu
    50                  55                  60

Thr Ile Thr Gln Ser Leu Ile Ser Arg Tyr His Lys Gly Glu Leu Lys
65                  70                  75                  80

Leu Glu Glu Pro Thr Tyr Phe Gln Ser Leu Leu Met Thr Tyr Lys Ser
                85                  90                  95

Met Ser Ser Ser Glu Gln Ile Ala Thr Thr Asn Leu Leu Lys Lys Ile
            100                 105                 110

Ile Arg Arg Ala Ile Glu Ile Ser Asp Val Lys Val Tyr Ala Ile Leu
        115                 120                 125

Asn Lys Leu Gly Leu Lys Glu Lys Asp Arg Val Lys Pro Asn Asn Asn
    130                 135                 140
```

-continued

```
Ser Gly Asp Glu Asn Ser Val Leu Thr Thr Ile Ile Lys Asp Asp Ile
145                 150                 155                 160

Leu Ser Ala Val Glu Asn Asn Gln Ser Tyr Thr Asn Ser Asp Lys Asn
                165                 170                 175

His Ser Val Asn Gln Asn Ile Thr Ile Lys Thr Thr Leu Leu Lys Lys
            180                 185                 190

Leu Met Cys Ser Met Gln His Pro Pro Ser Trp Leu Ile His Trp Phe
        195                 200                 205

Asn Leu Tyr Thr Lys Leu Asn Asn Ile Leu Thr Gln Tyr Arg Ser Asn
    210                 215                 220

Glu Val Lys Ser His Gly Phe Ile Leu Ile Asp Asn Gln Thr Leu Ser
225                 230                 235                 240

Gly Phe Gln Phe Ile Leu Asn Gln Tyr Gly Cys Ile Val Tyr His Lys
                245                 250                 255

Gly Leu Lys Lys Ile Thr Thr Thr Thr Tyr Asn Gln Phe Leu Thr Trp
            260                 265                 270

Lys Asp Ile Ser Leu Ser Arg Leu Asn Val Cys Leu Ile Thr Trp Ile
        275                 280                 285

Ser Asn Cys Leu Asn Thr Leu Asn Lys Ser Leu Gly Leu Arg Cys Gly
    290                 295                 300

Phe Asn Asn Val Val Leu Ser Gln Leu Phe Leu Tyr Gly Asp Cys Ile
305                 310                 315                 320

Leu Lys Leu Phe His Asn Glu Gly Phe Tyr Ile Ile Lys Glu Val Glu
                325                 330                 335

Gly Phe Ile Met Ser Leu Ile Leu Asn Ile Thr Glu Glu Asp Gln Phe
            340                 345                 350

Arg Thr Arg Phe Tyr Asn Ser Met Leu Asn Asn Ile Thr Asp Ala Ala
        355                 360                 365

Ile Lys Ala Gln Lys Asn Leu Leu Ser Arg Val Cys His Thr Leu Leu
    370                 375                 380

Asp Lys Thr Val Ser Asp Asn Ile Ile Asn Gly Lys Trp Ile Ile Leu
385                 390                 395                 400

Leu Ser Lys Phe Leu Lys Leu Ile Lys Leu Ala Gly Asp Asn Asn Leu
                405                 410                 415

Asn Asn Leu Ser Glu Leu Tyr Phe Leu Phe Arg Ile Phe Gly His Pro
            420                 425                 430

Met Val Asp Glu Arg Gln Ala Met Asp Ala Val Arg Ile Asn Cys Asn
        435                 440                 445

Glu Thr Lys Phe Tyr Leu Leu Ser Ser Leu Ser Thr Leu Arg Gly Ala
    450                 455                 460

Phe Ile Tyr Arg Ile Ile Lys Gly Phe Val Asn Thr Tyr Asn Arg Trp
465                 470                 475                 480

Pro Thr Leu Arg Asn Ala Ile Val Leu Pro Leu Arg Trp Leu Asn Tyr
                485                 490                 495

Tyr Lys Leu Asn Thr Tyr Pro Ser Leu Leu Glu Ile Thr Glu Asn Asp
            500                 505                 510

Leu Ile Ile Leu Ser Gly Leu Arg Phe Tyr Arg Glu Phe His Leu Pro
        515                 520                 525

Lys Lys Val Asp Leu Glu Met Ile Ile Asn Asp Lys Ala Ile Ser Pro
    530                 535                 540

Pro Lys Asp Leu Ile Trp Thr Ser Phe Pro Arg Asn Tyr Met Pro Ser
545                 550                 555                 560
```

-continued

```
His Ile Gln Asn Tyr Ile Glu His Glu Lys Leu Lys Phe Ser Glu Ser
                565                 570                 575

Asp Arg Ser Arg Arg Val Leu Glu Tyr Tyr Leu Arg Asp Asn Lys Phe
            580                 585                 590

Asn Glu Cys Asp Leu Tyr Asn Cys Val Val Asn Gln Ser Tyr Leu Asn
        595                 600                 605

Asn Ser Asn His Val Val Ser Leu Thr Gly Lys Glu Arg Glu Leu Ser
    610                 615                 620

Val Gly Arg Met Phe Ala Met Gln Pro Gly Met Phe Arg Gln Ile Gln
625                 630                 635                 640

Ile Leu Ala Glu Lys Met Ile Ala Glu Asn Ile Leu Gln Phe Phe Pro
                645                 650                 655

Glu Ser Leu Thr Arg Tyr Gly Asp Leu Glu Leu Gln Lys Ile Leu Glu
            660                 665                 670

Leu Lys Ala Gly Ile Ser Asn Lys Ser Asn Arg Tyr Asn Asp Asn Tyr
        675                 680                 685

Asn Asn Tyr Ile Ser Lys Cys Ser Ile Ile Thr Asp Leu Ser Lys Phe
    690                 695                 700

Asn Gln Ala Phe Arg Tyr Glu Thr Ser Cys Ile Cys Ser Asp Val Leu
705                 710                 715                 720

Asp Glu Leu His Gly Val Gln Ser Leu Phe Ser Trp Leu His Leu Thr
                725                 730                 735

Ile Pro Leu Val Thr Ile Ile Cys Thr Tyr Arg His Ala Pro Pro Phe
            740                 745                 750

Ile Lys Asp His Val Val Asn Leu Asn Glu Val Asp Glu Gln Ser Gly
        755                 760                 765

Leu Tyr Arg Tyr His Met Gly Gly Ile Glu Gly Trp Cys Gln Lys Leu
    770                 775                 780

Trp Thr Ile Glu Ala Ile Ser Leu Leu Asp Leu Ile Ser Leu Lys Gly
785                 790                 795                 800

Lys Phe Ser Ile Thr Ala Leu Ile Asn Gly Asp Asn Gln Ser Ile Asp
                805                 810                 815

Ile Ser Lys Pro Val Arg Leu Ile Glu Gly Gln Thr His Ala Gln Ala
            820                 825                 830

Asp Tyr Leu Leu Ala Leu Asn Ser Leu Lys Leu Leu Tyr Lys Glu Tyr
        835                 840                 845

Ala Gly Ile Gly His Lys Leu Lys Gly Thr Glu Thr Tyr Ile Ser Arg
    850                 855                 860

Asp Met Gln Phe Met Ser Lys Thr Ile Gln His Asn Gly Val Tyr Tyr
865                 870                 875                 880

Pro Ala Ser Ile Lys Lys Val Leu Arg Val Gly Pro Trp Ile Asn Thr
                885                 890                 895

Ile Leu Asp Asp Phe Lys Val Ser Leu Glu Ser Ile Gly Ser Leu Thr
            900                 905                 910

Gln Glu Leu Glu Tyr Arg Gly Glu Ser Leu Leu Cys Ser Leu Ile Phe
        915                 920                 925

Arg Asn Ile Trp Leu Tyr Asn Gln Ile Ala Leu Gln Leu Arg Asn His
    930                 935                 940

Ala Leu Cys His Asn Lys Leu Tyr Leu Asp Ile Leu Lys Val Leu Lys
945                 950                 955                 960

His Leu Lys Thr Phe Phe Asn Leu Asp Ser Ile Asp Met Ala Leu Ser
                965                 970                 975

Leu Tyr Met Asn Leu Pro Met Leu Phe Gly Gly Gly Asp Pro Asn Leu
```

-continued

```
        980                 985                 990

Leu Tyr Arg Ser Phe Tyr Arg Arg  Thr Pro Asp Phe Leu  Thr Glu Ala
    995                 1000                1005

Ile Val  His Ser Val Phe Val  Leu Ser Tyr Tyr Thr  Gly His Asp
    1010                 1015                 1020

Leu Gln  Asp Lys Leu Gln Asp  Leu Pro Asp Asp Arg  Leu Asn Lys
    1025                 1030                 1035

Phe Leu  Thr Cys Ile Ile Thr  Phe Asp Lys Asn Pro  Asn Ala Glu
    1040                 1045                 1050

Phe Val  Thr Leu Met Arg Asp  Pro Gln Ala Leu Gly  Ser Glu Arg
    1055                 1060                 1065

Gln Ala  Lys Ile Thr Ser Glu  Ile Asn Arg Leu Ala  Val Thr Glu
    1070                 1075                 1080

Val Leu  Ser Ile Ala Pro Asn  Lys Ile Phe Ser Lys  Ser Ala Gln
    1085                 1090                 1095

His Tyr  Thr Thr Thr Glu Ile  Asp Leu Asn Asp Ile  Met Gln Asn
    1100                 1105                 1110

Ile Glu  Pro Thr Tyr Pro His  Gly Leu Arg Val Val  Tyr Glu Ser
    1115                 1120                 1125

Leu Pro  Phe Tyr Lys Ala Glu  Lys Ile Val Asn Leu  Ile Ser Gly
    1130                 1135                 1140

Thr Lys  Ser Ile Thr Asn Ile  Leu Glu Lys Thr Ser  Ala Ile Asp
    1145                 1150                 1155

Thr Thr  Asp Ile Asn Arg Ala  Thr Asp Met Met Arg  Lys Asn Ile
    1160                 1165                 1170

Thr Leu  Leu Ile Arg Ile Leu  Pro Leu Asp Cys Asn  Lys Asp Lys
    1175                 1180                 1185

Arg Glu  Leu Leu Ser Leu Glu  Asn Leu Ser Ile Thr  Glu Leu Ser
    1190                 1195                 1200

Lys Tyr  Val Arg Glu Arg Ser  Trp Ser Leu Ser Asn  Ile Val Gly
    1205                 1210                 1215

Val Thr  Ser Pro Ser Ile Met  Phe Thr Met Asp Ile  Lys Tyr Thr
    1220                 1225                 1230

Thr Ser  Thr Ile Ala Ser Gly  Ile Ile Ile Glu Lys  Tyr Asn Val
    1235                 1240                 1245

Asn Ser  Leu Thr Arg Gly Glu  Arg Gly Pro Thr Lys  Pro Trp Val
    1250                 1255                 1260

Gly Ser  Ser Thr Gln Glu Lys  Lys Thr Met Pro Val  Tyr Asn Arg
    1265                 1270                 1275

Gln Val  Leu Thr Lys Lys Gln  Arg Asp Gln Ile Asp  Leu Leu Ala
    1280                 1285                 1290

Lys Leu  Asp Trp Val Tyr Ala  Ser Ile Asp Asn Lys  Asp Glu Phe
    1295                 1300                 1305

Met Glu  Glu Leu Ser Thr Gly  Thr Leu Gly Leu Ser  Tyr Glu Lys
    1310                 1315                 1320

Ala Lys  Lys Leu Phe Pro Gln  Tyr Leu Ser Val Asn  Tyr Leu His
    1325                 1330                 1335

Arg Leu  Thr Val Ser Ser Arg  Pro Cys Glu Phe Pro  Ala Ser Ile
    1340                 1345                 1350

Pro Ala  Tyr Arg Thr Thr Asn  Tyr His Phe Asp Thr  Ser Pro Ile
    1355                 1360                 1365

Asn His  Val Leu Thr Glu Lys  Tyr Gly Asp Glu Asp  Ile Asp Ile
    1370                 1375                 1380
```

-continued

Val Phe Gln Asn Cys Ile Ser Phe Gly Leu Ser Leu Met Ser Val
1385 1390 1395

Val Glu Gln Phe Thr Asn Ile Cys Pro Asn Arg Ile Ile Leu Ile
1400 1405 1410

Pro Lys Leu Asn Glu Ile His Leu Met Lys Pro Pro Ile Phe Thr
1415 1420 1425

Gly Asp Val Asp Ile Ile Lys Leu Lys Gln Val Ile Gln Lys Gln
1430 1435 1440

His Met Phe Leu Pro Asp Lys Ile Ser Leu Thr Gln Tyr Val Glu
1445 1450 1455

Leu Phe Leu Ser Asn Lys Ala Leu Lys Ser Gly Ser His Ile Asn
1460 1465 1470

Ser Asn Leu Ile Leu Val His Lys Met Ser Asp Tyr Phe His Asn
1475 1480 1485

Asp Tyr Ile Leu Ser Thr Asn Leu Ala Gly His Trp Ile Leu Ile
1490 1495 1500

Ile Gln Leu Met Lys Asp Ser Lys Gly Ile Phe Glu Lys Asp Trp
1505 1510 1515

Gly Glu Gly Tyr Ile Thr Asp His Met Phe Ile Asn Leu Asn Val
1520 1525 1530

Phe Phe Asn Ala Tyr Lys Thr Tyr Leu Leu Cys Phe His Lys Gly
1535 1540 1545

Tyr Gly Lys Ala Lys Leu Glu Cys Asp Met Asn Thr Ser Asp Leu
1550 1555 1560

Leu Cys Val Leu Glu Leu Ile Asp Ser Ser Tyr Trp Lys Ser Met
1565 1570 1575

Ser Lys Val Phe Leu Glu Gln Lys Val Ile Lys Tyr Ile Val Asn
1580 1585 1590

Gln Asp Thr Ser Leu His Arg Ile Lys Gly Cys His Ser Phe Lys
1595 1600 1605

Leu Trp Phe Leu Lys Arg Leu Asn Asn Ala Lys Phe Thr Val Cys
1610 1615 1620

Pro Trp Val Val Asn Ile Asp Tyr His Pro Thr His Met Lys Ala
1625 1630 1635

Ile Leu Ser Tyr Ile Asp Leu Val Arg Met Gly Leu Ile Asn Val
1640 1645 1650

Asp Lys Leu Thr Ile Lys Asn Lys Asn Lys Phe Asn Asp Glu Phe
1655 1660 1665

Tyr Thr Ser Asn Leu Phe Tyr Ile Ser Tyr Asn Phe Ser Asp Asn
1670 1675 1680

Thr His Leu Leu Thr Lys Gln Ile Arg Ile Ala Asn Ser Glu Leu
1685 1690 1695

Glu Asn Asn Tyr Asn Lys Leu Tyr His Pro Thr Pro Glu Thr Leu
1700 1705 1710

Glu Asn Met Ser Leu Ile Pro Val Lys Ser Asn Asn Ser Asn Lys
1715 1720 1725

Pro Lys Ser Cys Ile Ser Gly Asn Thr Glu Ser Met Met Thr Ser
1730 1735 1740

Thr Phe Ser Asn Lys Met His Ile Lys Ser Ser Thr Val Thr Thr
1745 1750 1755

Arg Leu Asn Tyr Ser Lys Gln Asp Leu Tyr Asn Leu Phe Pro Ile
1760 1765 1770

-continued

```
Val Val  Ile Asp Arg Ile Ile  Asp His Ser Gly Asn  Thr Ala Lys
    1775                 1780                 1785

Ser Asn  Gln Leu Tyr Thr Thr  Thr Ser His Gln Thr  Ser Leu Val
    1790                 1795                 1800

Arg Asn  Ser Ala Ser Leu Tyr  Cys Met Leu Pro Trp  His His Val
    1805                 1810                 1815

Asn Arg  Phe Asn Phe Val Phe  Ser Ser Thr Gly Cys  Lys Ile Ser
    1820                 1825                 1830

Ile Glu  Tyr Ile Leu Lys Asp  Leu Lys Ile Lys Asp  Pro Ser Cys
    1835                 1840                 1845

Ile Ala  Phe Ile Gly Glu Gly  Ala Gly Asn Leu Leu  Leu Arg Thr
    1850                 1855                 1860

Val Val  Glu Leu His Pro Asp  Ile Arg Tyr Ile Tyr  Arg Ser Leu
    1865                 1870                 1875

Lys Asp  Cys Asn Asp His Ser  Leu Pro Ile Glu Phe  Leu Arg Leu
    1880                 1885                 1890

Tyr Asn  Gly His Ile Asn Ile  Asp Tyr Gly Glu Asn  Leu Thr Ile
    1895                 1900                 1905

Pro Ala  Thr Asp Ala Thr Asn  Asn Ile His Trp Ser  Tyr Leu His
    1910                 1915                 1920

Ile Lys  Phe Ala Glu Pro Ile  Ser Ile Phe Val Cys  Asp Ala Glu
    1925                 1930                 1935

Leu Pro  Val Thr Ala Asn Trp  Ser Lys Ile Ile Ile  Glu Trp Ser
    1940                 1945                 1950

Lys His  Val Arg Lys Cys Lys  Tyr Cys Ser Ser Val  Asn Arg Cys
    1955                 1960                 1965

Ile Leu  Ile Ala Lys Tyr His  Ala Gln Asp Asp Ile  Asp Phe Lys
    1970                 1975                 1980

Leu Asp  Asn Ile Thr Ile Leu  Lys Thr Tyr Val Cys  Leu Gly Ser
    1985                 1990                 1995

Lys Leu  Lys Gly Ser Glu Val  Tyr Leu Val Leu Thr  Ile Gly Pro
    2000                 2005                 2010

Ser Asn  Ile Leu Pro Val Phe  Asn Val Val Gln Asn  Ala Lys Leu
    2015                 2020                 2025

Ile Leu  Ser Arg Thr Lys Asn  Phe Ile Met Pro Lys  Lys Thr Asp
    2030                 2035                 2040

Lys Glu  Ser Ile Asp Ala Asn  Ile Lys Ser Leu Ile  Pro Phe Leu
    2045                 2050                 2055

Cys Tyr  Pro Ile Thr Lys Lys  Gly Ile Lys Thr Ser  Leu Ser Lys
    2060                 2065                 2070

Leu Lys  Ser Val Val Asn Gly  Asp Ile Leu Ser Tyr  Ser Ile Ala
    2075                 2080                 2085

Gly Arg  Asn Glu Val Phe Ser  Asn Lys Leu Ile Asn  His Lys His
    2090                 2095                 2100

Met Asn  Ile Leu Lys Trp Leu  Asp His Val Leu Asn  Phe Arg Ser
    2105                 2110                 2115

Thr Glu  Leu Asn Tyr Asn His  Leu Tyr Met Ile Glu  Ser Thr Tyr
    2120                 2125                 2130

Pro Tyr  Leu Ser Glu Leu Leu  Asn Ser Leu Thr Thr  Asn Glu Leu
    2135                 2140                 2145

Lys Lys  Leu Ile Lys Ile Thr  Gly Ser Val Leu Tyr  Asn Leu Pro
    2150                 2155                 2160

Asn Glu  Gln
```

-continued

2165

<210> SEQ ID NO 12
<211> LENGTH: 292
<212> TYPE: PRT
<213> ORGANISM: respiratory syncytial virus B 9320

<400> SEQUENCE: 12

```
Met Ser Lys His Lys Ser Gln Arg Thr Ala Arg Thr Leu Glu Lys Thr
1               5                   10                  15

Trp Asp Thr Leu Asn His Leu Ile Val Ile Ser Ser Cys Leu Tyr Arg
            20                  25                  30

Leu Asn Leu Lys Ser Ile Ala Gln Ile Ala Leu Ser Val Leu Ala Met
        35                  40                  45

Ile Ile Ser Thr Ser Leu Ile Ile Ala Ala Ile Ile Phe Ile Ile Ser
    50                  55                  60

Ala Asn His Lys Val Thr Leu Thr Thr Val Thr Val Gln Thr Ile Lys
65                  70                  75                  80

Asn His Thr Glu Lys Asn Ile Thr Thr Tyr Leu Thr Gln Val Ser Pro
                85                  90                  95

Glu Arg Val Ser Ser Ser Ile Gln Pro Thr Thr Thr Ser Pro Ile His
            100                 105                 110

Thr Asn Ser Ala Thr Ile Ser Pro Asn Thr Lys Ser Glu Thr His His
        115                 120                 125

Thr Thr Thr Gln Ala Lys Ser Arg Ile Thr Thr Ser Thr Gln Thr Asn
    130                 135                 140

Lys Pro Ser Thr Lys Ser Arg Ser Lys Asn Pro Pro Lys Lys Pro Lys
145                 150                 155                 160

Asp Asp Tyr His Phe Glu Val Phe Asn Phe Val Pro Cys Ser Ile Cys
                165                 170                 175

Gly Asn Asn Gln Leu Cys Lys Ser Ile Cys Lys Thr Ile Pro Ser Asn
            180                 185                 190

Lys Pro Lys Lys Lys Pro Thr Ile Lys Pro Thr Asn Lys Pro Thr Val
        195                 200                 205

Lys Thr Thr Asn Lys Arg Asp Pro Lys Thr Pro Ala Lys Met Met Lys
    210                 215                 220

Lys Glu Thr Thr Thr Asn Pro Thr Lys Lys Pro Thr Leu Lys Thr Thr
225                 230                 235                 240

Glu Gly Asp Thr Ser Thr Ser Gln Ser Thr Val Leu Asp Thr Thr Thr
                245                 250                 255

Ser Lys His Thr Ile Gln Gln Gln Ser Leu His Ser Ile Thr Ser Glu
            260                 265                 270

Asn Thr Pro Asn Ser Thr Gln Ile Pro Thr Ala Thr Glu Ala Ser Thr
        275                 280                 285

Ser Asn Ser Thr
    290
```

<210> SEQ ID NO 13
<211> LENGTH: 15225
<212> TYPE: DNA
<213> ORGANISM: respiratory syncytial virus B 1

<400> SEQUENCE: 13

```
acgcgaaaaa atgcgtacta caaacttgca cattcggaaa aaatggggca aataagaatt      60

tgataagtgc tatttaagtc taacctttc aatcagaaat ggggtgcaat tcactgagca     120
```

-continued

```
tgataaaggt tagattacaa aatttatttg acaatgacga agtagcattg ttaaaaataa    180
catgttatac tgacaaatta attcttctga ccaatgcatt agccaaagca gcaatacata    240
caattaaatt aaacggtata gtttttatac atgttataac aagcagtgaa gtgtgccctg    300
ataacaacat tgtagtaaaa tctaacttta caacaatgcc aatattacaa aacggaggat    360
acatatggga attgattgag ttgacacact gctctcaatt aaacggtcta atggatgata    420
attgtgaaat caaattttct aaaagactaa gtgactcagt aatgactaat tatatgaatc    480
aaatatctga tttacttggg cttgatctca attcatgaat tatgtttagt ctaactcaat    540
agacatgtgt ttattaccat tttagttaat ataaaaactc atcaaaggga aatggggcaa    600
ataaactcac ctaatcaatc aaactatgag cactacaaat gacaacacta ctatgcaaag    660
attaatgatc acggacatga gacccctgtc gatggattca ataataacat ctctcaccaa    720
agaaatcatc acacacaaat tcatatactt gataaacaat gaatgtattg taagaaaact    780
tgatgaaaga caagctacat ttacattctt agtcaattat gagatgaagc tactgcacaa    840
agtagggagt accaaataca agaaatacac tgaatataat acaaaatatg gcactttccc    900
catgcctata tttatcaatc atggcgggtt tctagaatgt attggcatta agcctacaaa    960
acacactcct ataatataca aatatgacct caacccgtaa attccaacaa aaaaaaccaa   1020
cccaaccaaa ccaagctatt cctcaaacaa caatgctcaa tagttaagaa ggagctaatc   1080
cgttttagta attaaaaata aaagtaaagc caataacata aattggggca aatacaaaga   1140
tggctcttag caaagtcaag ttaaatgata cattaaataa ggatcagctg ctgtcatcca   1200
gcaaatacac tattcaacgt agtacaggag ataatattga cactcccaat tatgatgtgc   1260
aaaaacacct aaacaaacta tgtggtatgc tattaatcac tgaagatgca aatcataaat   1320
tcacaggatt aataggtatg ttatatgcta tgtccaggtt aggaagggaa gacactataa   1380
agatacttaa agatgctgga tatcatgtta aagctaatgg agtagatata acaacatatc   1440
gtcaagatat aaatggaaag gaaatgaaat tcgaagtatt aacattatca agcttgacat   1500
cagaaataca agtcaatatt gagatagaat ctagaaaatc ctacaaaaaa atgctaaaag   1560
agatgggaga agtggctcca gaatataggc atgattctcc agactgtggg atgataatac   1620
tgtgtatagc agcacttgta ataaccaaat tagcagcagg agacagatca ggtcttacag   1680
cagtaattag gagggcaaac aatgtcttaa aaaatgaaat aaaacgctac aagggtctca   1740
taccaaagga tatagctaac agtttttatg aagtgtttga aaaacaccct catcttatag   1800
atgtttttgt gcactttggc attgcacaat catcaacaag agggggtagt agagttgaag   1860
gaatctttgc aggattgttt atgaatgcct atggttcagg gcaagtaatg ctaagatggg   1920
gagttttagc caaatctgta aaaaatatca tgctaggtca tgctagtgtc caggcagaaa   1980
tggagcaagt tgtggaagtc tatgagtatg cacagaagtt gggaggagaa gctggattct   2040
accatatatt gaacaatcca aaagcatcat tgctgtcatt aactcaattt cctaacttct   2100
caagtgtggt cctaggcaat gcagcaggtc taggcataat gggagagtat agaggtacgc   2160
caagaaacca ggatctttat gatgcagcca aagcatatgc agagcaactc aaagaaaatg   2220
gagtaataaa ctacagtgta ttagacttaa cagcagaaga attggaagcc ataaagaatc   2280
aactcaaccc taaagaagat gatgtagagc tttaagttaa caaaaaatac ggggcaaata   2340
agtcaacatg gagaagtttg cacctgaatt tcatggagaa gatgcaaata acaaagctac   2400
caaattccta gaatcaataa agggcaagtt cgcatcatcc aaagatccta agaagaaaga   2460
tagcataata tctgttaact caatagatat agaagtaacc aaagagagcc cgataacatc   2520
```

-continued

```
tggcaccaac atcatcaatc caacaagtga agccgacagt accccagaaa ccaaagccaa   2580
ctacccaaga aaaccccctag taagcttcaa agaagatctc accccaagtg acaacccttt   2640
ttctaagttg tacaaagaaa caatagaaac atttgataac aatgaagaag aatctagcta   2700
ctcatatgaa gagataaatg atcaaacaaa tgacaacatt acagcaagac tagatagaat   2760
tgatgaaaaa ttaagtgaaa tattaggaat gctccataca ttagtagttg caagtgcagg   2820
acccacttca gctcgcgatg gaataagaga tgctatggtt ggtctgagag aagaaatgat   2880
agaaaaaata agagcggaag cattaatgac caatgatagg ttagaggcta tggcaagact   2940
taggaatgag gaaagcgaaa aaatggcaaa agacacctca gatgaagtgc ctcttaatcc   3000
aacttccaaa aaattgagtg acttgttgga agacaacgat agtgacaatg atctgtcact   3060
tgatgatttt tgatcagtga tcaactcact cagcaatcaa caacatcaat aaaacagaca   3120
tcaatccatt gaatcaactg ccagaccgaa caaacaaatg tccgtcagcg gaaccaccaa   3180
ccaatcaatc aaccaactga tccatcagca acctgacgaa attaacaata tagtaacaaa   3240
aaaagaacaa gatggggcaa atatggaaac atacgtgaac aagcttcacg aaggctccac   3300
atacacagca gctgttcagt acaatgttct agaaaaagat gatgatcctg catcactaac   3360
aatatgggtg cctatgttcc agtcatctgt accagcagac ttgctcataa aagaacttgc   3420
aagcatcaac atactagtga agcagatctc tacgcccaaa ggaccttcac tacgagtcac   3480
gattaactca agaagtgctg tgctggctca aatgcctagt aatttcatca taagcgcaaa   3540
tgtatcatta gatgaaagaa gcaaattagc atatgatgta actacacctt gtgaaatcaa   3600
agcatgcagt ctaacatgct taaaagtgaa aagtatgtta actacagtca aagatcttac   3660
catgaagaca ttcaacccca ctcatgagat cattgctcta tgtgaatttg aaaatattat   3720
gacatcaaaa agagtaataa taccaaccta tctaagacca attagtgtca aaaacaagga   3780
tctgaactca ctagaaaaca tagcaaccac cgaattcaaa aatgctatca ccaatgcgaa   3840
aattattccc tatgctggat tagtattagt tatcacagtt actgacaata aaggagcatt   3900
caaatatatc aagccacaga gtcaatttat agtagatctt ggtgcctacc tagaaaaaga   3960
gagcatatat tatgtgacta ctaattggaa gcatacagct acacgttttt caatcaaacc   4020
actagaggat taaatttaat tatcaacact gaatgacagg tccacatata tcctcaaact   4080
acacactata tccaaacatc atgaacatct acactacaca cttcatcaca caaaccaatc   4140
ccactcaaaa tccaaaatca ctaccagcca ctatctgcta gacctagagt gcgaataggt   4200
aaataaaacc aaaatatggg gtaaatagac attagttaga gttcaatcaa tctcaacaac   4260
catttatacc gccaattcaa tacatatact ataaatctta aaatgggaaa tacatccatc   4320
acaatagaat tcacaagcaa attttggccc tattttacac taatacatat gatcttaact   4380
ctaatctctt tactaattat aatcactatt atgattgcaa tactaaataa gctaagtgaa   4440
cataaaacat tctgtaacaa tactcttgaa ctaggacaga tgcatcaaat caacacatag   4500
tgctctacca tcatgctgtg tcaaattata atcctgtata tataaacaaa caaatccaat   4560
cttctcacag agtcatggtg tcgcaaaacc acgccaacta tcatggtagc atagagtagt   4620
tatttaaaaa ttaacataat gatgaattat tagtatggga tcaaaaacaa cattggggca   4680
aatgcaacca tgtccaaaca caagaatcaa cgcactgcca ggactctaga aaagacctgg   4740
gatactctca atcatctaat tgtaatatcc tcttgtttat acagattaaa tttaaaatct   4800
atagcacaaa tagcactatc agttctggca atgataatct caacctctct cataattgca   4860
```

-continued

```
gccataatat tcatcatctc tgccaatcac aaagttacac taacaacggt cacagttcaa   4920
acaataaaaa accacactga aaaaaacatc accacctacc ttactcaagt cccaccagaa   4980
agggttagct catccaaaca acctacaacc acatcaccaa tccacacaaa ttcagccaca   5040
acatcaccca acacaaagtc agaaacacac cacacaacag cacaaaccaa aggcagaacc   5100
accacctcaa cacagaccaa caagccgagc acaaaaccac gcctaaaaaa tccaccaaaa   5160
aaaccaaaag atgattacca ttttgaagtg ttcaacttcg ttccctgtag tatatgtggc   5220
aacaatcaac tttgcaaatc catctgtaaa acaataccaa gcaacaaacc aaagaagaaa   5280
ccaaccatca aacccacaaa caaaccaacc accaaaacca caaacaaaag agacccaaaa   5340
acaccagcca aaacgacgaa aaaagaaact accaccaacc caacaaaaaa accaaccctc   5400
acgaccacag aaagagacac cagcacctca caatccactg tgctcgacac aaccacatta   5460
gaacacacaa tccaacagca atccctccac tcaaccaccc ccgaaaacac acccaactcc   5520
acacaaacac ccacagcatc cgagccctct acatcaaatt ccacccaaaa tacccaatca   5580
catgcttagt tattcaaaaa ctacatctta gcagaaaacc gtgacctatc aagcaagaac   5640
gaaattaaac ctggggcaaa taaccatgga gctgctgatc cacaggttaa gtgcaatctt   5700
cctaactctt gctattaatg cattgtacct cacctcaagt cagaacataa ctgaggagtt   5760
ttaccaatcg acatgtagtg cagttagcag aggttatttt agtgctttaa gaacaggttg   5820
gtataccagt gtcataacaa tagaattaag taatataaaa gaaaccaaat gcaatggaac   5880
tgacactaaa gtaaaactta taaaacaaga attagataag tataagaatg cagtgacaga   5940
attacagcta cttatgcaaa acacaccagc tgccaacaac cgggccagaa gagaagcacc   6000
acagtatatg aactatacaa tcaataccac taaaaaccta aatgtatcaa taagcaagaa   6060
gaggaaacga agatttctgg gcttcttgtt aggtgtagga tctgcaatag caagtggtat   6120
agctgtatcc aaagttctac accttgaagg agaagtgaac aagatcaaaa atgctttgtt   6180
atctacaaac aaagctgtag tcagtctatc aaatggggtc agtgttttaa ccagcaaagt   6240
gttagatctc aagaattaca taaataacca attattaccc atagtaaatc aacagagctg   6300
tcgcatctcc aacattgaaa cagttataga attccagcag aagaacagca gattgttgga   6360
aatcaacaga gaattcagtg tcaatgcagg tgtaacaaca cctttaagca cttacatgtt   6420
aacaaacagt gagttactat cattgatcaa tgatatgcct ataacaaatg atcagaaaaa   6480
attaatgtca agcaatgttc agatagtaag gcaacaaagt tattctatca tgtctataat   6540
aaaggaagaa gtccttgcat atgttgtaca gctacctatc tatggtgtaa tagatacacc   6600
ttgctggaaa ttacacacat cacctctatg caccaccaac atcaaagaag gatcaaatat   6660
ttgtttaaca aggactgata gaggatggta ttgtgataat gcaggatcag tatccttctt   6720
tccacaggct gacacttgta aagtacagtc caatcgagta ttttgtgaca ctatgaacag   6780
tttgacatta ccaagtgaag tcagcctttg taacactgac atattcaatt ccaagtatga   6840
ctgcaaaatt atgacatcaa aaacagacat aagcagctca gtaattactt ctcttggagc   6900
tatagtgtca tgctatggta aaactaaatg cactgcatcc aacaaaaatc gtgggattat   6960
aaagacattt tctaatggtt gtgactatgt gtcaaacaaa ggagtagata ctgtgtcagt   7020
gggcaacact ttatactatg taaacaagct ggaaggcaag aacctttatg taaaagggga   7080
acctataata aattactatg accctctagt gtttccttct gatgagtttg atgcatcaat   7140
atctcaagtc aatgaaaaaa tcaatcaaag tttagctttt attcgtagat ctgatgaatt   7200
actacataat gtaaatactg gcaaatctac tacaaatatt atgataacta caattattat   7260
```

-continued

```
agtaatcatt gtagtattgt tatcattaat agctattggt ttgctgttgt attgcaaagc   7320
caaaaacaca ccagttacac taagcaaaga ccaactaagt ggaatcaata atattgcatt   7380
cagcaaatag acaaaaaacc acctgatcat gtttcaacaa cagtctgctg atcaccaatc   7440
ccaaatcaac ccataacaaa cacttcaaca tcacagtaca ggctgaatca tttcttcaca   7500
tcatgctacc cacacaacta agctagatcc ttaactcata gttacataaa aacctcaagt   7560
atcacaatca aacactaaat caacacatca ttcacaaaat taacagctgg ggcaaatatg   7620
tcgcgaagaa atccttgtaa atttgagatt agaggtcatt gcttgaatgg tagaagatgt   7680
cactacagtc ataattactt tgaatggcct cctcatgcct tactagtgag gcaaaacttc   7740
atgttaaaca agatactcaa gtcaatggac aaaagcatag acactttgtc tgaaataagt   7800
ggagctgctg aactggacag aacagaagaa tatgctcttg gtatagttgg agtgctagag   7860
agttacatag gatctataaa caacataaca aaacaatcag catgtgttgc tatgagtaaa   7920
cttcttattg agatcaatag tgatgacatt aaaaagctga gagataatga agaacccaat   7980
tcacctaaga taagagtgta caatactgtt atatcataca ttgagagcaa tagaaaaaac   8040
aacaagcaaa caatccatct gctcaaaaga ctaccagcag acgtgctgaa gaagacaata   8100
aaaaacacat tagatatcca caaaagcata atcataagca acccaaaaga gtcaaccgtg   8160
aatgatcaaa atgaccaaac caaaaataat gatattaccg gataaatatc cttgtagtat   8220
atcatccata ttgatttcaa gtgaaagcat gattgctaca ttcaatcata aaaacatatt   8280
acaatttaac cataaccatt tggataacca ccagcgttta ttaaataata tatttgatga   8340
aattcattgg acacctaaaa acttattaga tgccactcaa caatttctcc aacatcttaa   8400
catccctgaa gatatatata caatatatat attagtgtca taatgcttgg ccataacgat   8460
tctatatcat ccaaccataa aactatctta ataaggttat gggacaaaat ggatcccatt   8520
attaatggaa actctgctaa tgtgtatcta actgatagtt atttaaaagg tgttatctct   8580
ttttcagaat gtaatgcttt agggagttac ctttttaacg gcccttatct caaaaatgat   8640
tacaccaact taattagtag acaaagtcca ctactagagc atatgaatct taaaaaacta   8700
actataacac agtcattaat atctagatat cataaaggtg aactgaaatt agaagaacca   8760
acttatttcc agtcattact tatgacatat aaaagcatgt cctcgtctga acaaattgct   8820
acaactaact tacttaaaaa aataatacga agagctatag aaataagtga tgtaaaggtg   8880
tacgccatct tgaataaact aggactaaag gaaaaggaca gagttaagcc caacaataat   8940
tcaggtgatg aaaactcagt acttacaact ataattaaag atgatatact ttcggctgtg   9000
gaaagcaatc aatcatatac aaattcagac aaaaatcact cagtaaatca aaatatcact   9060
atcaaaacaa cactcttgaa aaaattgatg tgttcaatgc aacatcctcc atcatggtta   9120
atacactggt tcaatttata tacaaaatta aataacatat taacacaata tcgatcaaat   9180
gaggtaaaaa gtcatgggtt tatattaata gataatcaaa ctttaagtgg ttttcagttt   9240
attttaaatc aatatggttg tatcgtttat cataaaggac tcaaaaaaat cacaactact   9300
acttacaatc aatttttaac atggaaagac atcagcctta gcagattaaa tgtttgctta   9360
attacttgga taagtaattg tttgaataca ttaaataaaa gcttagggct gagatgtgga   9420
ttcaataatg ttgtgttatc acaattattt ctttatggag attgtatact gaaattattt   9480
cataatgaag gcttctacat aataaaagaa gtagagggat ttattatgtc tttaattcta   9540
aacataacag aagaagatca atttaggaaa cgattttata atagcatgct aaataacatc   9600
```

-continued

```
acagatgcag ctattaaggc tcaaaagaac ctactatcaa gggtatgtca cactttatta   9660
gacaagacag tgtctgataa tatcataaat ggtaaatgga taatcctatt aagtaaattt   9720
cttaaattga ttaagcttgc aggtgataat aatctcaata atttgagtga gctatatttt   9780
ctcttcagaa tctttggaca tccaatggtt gatgaaagac aagcaatgga tgctgtaaga   9840
attaactgta atgaaactaa gttctactta ttaagtagtc taagtacgtt aagaggtgct   9900
ttcatttata gaatcataaa agggtttgta aatacctaca acagatggcc cactttaagg   9960
aatgctattg tcctacctct aagatggtta aactattata aacttaatac ttatccatct  10020
ctacttgaaa tcacagaaaa tgatttgatt attttatcag gattgcggtt ctatcgtgaa  10080
tttcatctgc ctaaaaaagt ggatcttgaa atgataataa atgacaaagc catttcacct  10140
ccaaaagatc taatatggac tagttttcct agaaattaca tgccatcaca tatacaaaat  10200
tatatagaac atgaaaagtt gaagttctct gaaagcgaca gatcaagaag agtactagag  10260
tattacttga gagataataa attcaatgaa tgcgatctat acaattgtgt agtcaatcaa  10320
agctatctca acaactctaa tcacgtggta tcactaactg gtaaagaaag agagctcagt  10380
gtaggtagaa tgtttgctat gcaaccaggt atgtttaggc aaatccaaat cttagcagag  10440
aaaatgatag ccgaaaatat tttacaattc ttccctgaga gtttgacaag atatggtgat  10500
ctagagcttc aaaagatatt agaattaaaa gcaggaataa gcaacaagtc aaatcgttat  10560
aatgataact acaacaatta tatcagtaaa tgttctatca ttacagatct tagcaaattc  10620
aatcaagcat ttagatatga aacatcatgt atctgcagtg atgtattaga tgaactgcat  10680
ggagtacaat ctctgttctc ttggttgcat ttaacaatac ctcttgtcac aataatatgt  10740
acatatagac atgcacctcc tttcataaag gatcatgttg ttaatcttaa tgaagttgat  10800
gaacaaagtg gattatacag atatcatatg ggtggtattg agggctggtg tcaaaaactg  10860
tggaccattg aagctatatc attattagat ctaatatctc tcaaagggaa attctctatc  10920
acagctctga taaatggtga taatcagtca attgatataa gtaaaccagt tagacttata  10980
gagggtcaga cccatgctca agcagattat ttgttagcat taaatagcct taaattgcta  11040
tataaagagt atgcaggtat aggccataag cttaagggaa cagagaccta tatatcccga  11100
gatatgcagt tcatgagcaa aacaatccag cacaatggag tgtactatcc agccagtatc  11160
aaaaaagtcc tgagagtagg tccatggata aatacaatac ttgatgattt taaagttagt  11220
ttagaatcta taggtagctt aacacaggag ttagaataca gaggggaaag cttattatgc  11280
agtttaatat ttaggaacat ttggttatac aatcaaattg ctttgcaact ccgaaatcat  11340
gcattatgta acaataagct atatttagat atattgaaag tattaaaaca cttaaaaact  11400
ttttttaatc ttgatagtat cgatatggcg ttatcattgt atatgaattt gcctatgctg  11460
tttggtggtg gtgatcctaa tttgttatat cgaagctttt ataggagaac tccagacttc  11520
cttacagaag ctatagtaca ttcagtgttt gtgttgagct attatactgg tcacgattta  11580
caagataagc tccaggatct tccagatgat agactgaaca aattcttgac atgtgtcatc  11640
acattcgata aaaatcccaa tgccgagttt gtaacattga tgagggatcc acaggcgtta  11700
gggtctgaaa ggcaagctaa aattactagt gagattaata gattagcagt aacagaagtc  11760
ttaagtatag ctccaaacaa aatattttct aaaagtgcac aacattatac taccactgag  11820
attgatctaa atgacattat gcaaaatata gaaccaactt accctcatgg attaagagtt  11880
gtttatgaaa gtctaccttt ttataaagca gaaaaaatag ttaatcttat atcaggaaca  11940
aaatccataa ctaatatact tgaaaaaaca tcagcaatag atacaactga tattaatagg  12000
```

-continued

```
gctactgata tgatgaggaa aaatataact ttacttataa ggatacttcc actagattgt  12060
aacaaagaca aaagagagtt attaagttta gaaaatctta gtataactga attaagcaag  12120
tatgtaagag aaagatcttg gtcattatcc aatatagtag gagtaacatc gccaagtatt  12180
atgttcacaa tggacattaa atatacaact agcactatag ccagtggtat aattatagaa  12240
aaatataatg ttaatagttt aactcgtggt gaaagaggac ctactaagcc atgggtaggt  12300
tcatctacgc aggagaaaaa aacaatgcca gtgtacaata gacaagtttt aaccaaaaag  12360
caaagagacc aaatagattt attagcaaaa ttagactggg tatatgcatc catagacaac  12420
aaagatgaat tcatggaaga actgagtact ggaacacttg gactgtcata tgaaaaagcc  12480
aaaaagttgt ttccacaata tctaagtgtc aattatttac accgtttaac agtcagtagt  12540
agaccatgtg aattccctgc atcaatacca gcttatagaa caacaaatta tcatttcgat  12600
actagtccta tcaatcatgt attaacagaa aagtatggag atgaagatat cgacattgtg  12660
tttcaaaatt gcataagttt tggtcttagc ctgatgtcgg ttgtggaaca attcacaaac  12720
atatgtccta atagaattat tctcataccg aagctgaatg agatacattt gatgaaacct  12780
cctatattta caggagatgt tgatatcatc aagttgaagc aagtgataca aaaacagcat  12840
atgttcctac cagataaaat aagtttaacc caatatgtag aattattcct aagtaacaaa  12900
gcacttaaat ctggatctaa catcaattct aatttaatat tagtacataa aatgtctgat  12960
tattttcata atgcttatat tttaagtact aatttagctg gacattggat tctaattatt  13020
caacttatga aagattcaaa aggtattttt gaaaaagatt ggggagaggg gtacataact  13080
gatcatatgt tcattaattt gaatgttttc tttaatgctt ataagactta tttgctatgt  13140
tttcataaag gttatggtaa agcaaaatta gaatgtgata tgaacacttc agatcttctt  13200
tgtgttttgg agttaataga cagtagctac tggaaatcta tgtctaaagt tttcctagaa  13260
caaaaagtca taaaatacat agtcaatcaa gacacaagtt tgcatagaat aaaaggctgt  13320
cacagtttta agttgtggtt tttaaaacgc cttaataatg ctaaatttac cgtatgccct  13380
tgggttgtta acatagatta tcacccaaca catatgaaag ctatattatc ttacatagat  13440
ttagttagaa tggggttaat aaatgtagat aaattaacca ttaaaaaataa aaacaaattc  13500
aatgatgaat tttacacatc aaatctcttt tacattagtt ataacttttc agacaacact  13560
catttgctaa caaaacaaat aagaattgct aattcagaat tagaagataa ttataacaaa  13620
ctatatcacc caaccccaga aactttagaa aatatatcat taattcctgt taaaagtaat  13680
aatagtaaca aacctaaatt ttgtataagt ggaaataccg aatctataat gatgtcaaca  13740
ttctctaata aaatgcatat taaatcttcc actgttacca caagattcaa ttatagcaaa  13800
caagacttgt acaatttatt tccaaatgtt gtgatagaca ggattataga tcattcaggt  13860
aatacagcaa aatctaacca actttacatc accacttcac atcagacatc tttagtaagg  13920
aatagtgcat cactttattg catgcttcct tggcatcatg tcaatagatt taactttgta  13980
tttagttcca caggatgcaa gatcagtata gagtatattt taaaagatct taagattaag  14040
gaccccagtt gtatagcatt cataggtgaa ggagctggta acttattatt acgtacggta  14100
gtagaacttc atccagacat aagatacatt tacagaagtt taaaagattg caatgatcat  14160
agtttaccta ttgaatttct aagattatac aacgggcata taaacataga ttatggtgag  14220
aatttaacca ttcctgctac agatgcaact aataacattc attggtctta tttacatata  14280
aaatttgcag aacctattag catctttgtc tgcgatgctg aattacctgt tacagccaat  14340
```

-continued

```
tggagtaaaa ttataattga atggagtaag catgtaagaa agtgcaagta ctgttcttct  14400

gtaaatagat gcattttaat cgcaaaatat catgctcaag atgatattga tttcaaatta  14460

gataacatta ctatattaaa aacttacgtg tgcctaggta gcaagttaaa aggatctgaa  14520

gtttacttag tccttacaat aggccctgca aatatacttc ctgtttttga tgttgtgcaa  14580

aatgctaaat tgatttttc aagaactaaa aatttcatta tgcctaaaaa aactgacaag  14640

gaatctatcg atgcaaatat taaaagctta atacctttcc tttgttaccc tataacaaaa  14700

aaaggaatta agacttcatt gtcaaaattg aagagtgtag ttaatgggga tatattatca  14760

tattctatag ctggacgtaa tgaagtattc agcaacaagc ttataaacca caagcatatg  14820

aatatcctaa aatggctaga tcatgtttta aattttagat cagctgaact taattacaat  14880

catttataca tgatagagtc cacatatcct tacttaagtg aattgttaaa tagtttaaca  14940

accaatgagc tcaagaaact gattaaaata acaggtagtg tactatacaa ccttcccaac  15000

gaacagtaac ttaaaatatc attaacaagt ttggtcaaat ttagatgcta acacatcatt  15060

atattatagt tattaaaaaa tatgcaaact tttcaataat ttagcttact gattccaaaa  15120

ttatcatttt atttttaagg ggttgaataa aagtctaaaa ctaacaatga tacatgtgca  15180

tttacaacac aacgagacat tagtttttga cacttttttt ctcgt                  15225
```

<210> SEQ ID NO 14
<211> LENGTH: 868
<212> TYPE: DNA
<213> ORGANISM: respiratory syncytial virus B 9320

<400> SEQUENCE: 14

```
agtcaacgca ctgccaggac tctagaaaag acctgggata ctcttaatca tctaattgta     60

atatcctctt gtttatacag actaaaccta aaatctatag cacaaatagc actatcagtt    120

ttggcaatga taatctcaac ctctctcata attgcagcca taatattcat catctctgcc    180

aatcacaaag ttacactaac aacggttaca gttcaaacaa taaaaaacca cactgaaaaa    240

aacatcacca cctaccttac tcaagtctca ccagaaaggg ttagctcatc catacaacct    300

acaaccacat caccaatcca cacaaattca gctacaatat caccaaatac aaaatcagaa    360

acacaccata caacaacaca agccaaaagc agaatcacca cttcaacaca gaccaacaag    420

ccaagcacaa aatcacgttc aaaaaatcca ccaaaaaaac caaaagatga ttaccatttt    480

gaagtgttca attttgttcc ctgtagtata tgtggcaaca atcaactttg caaatccatc    540

tgcaaaacaa taccaagcaa caaaccaaag aaaaaaccaa ccatcaaacc cacaaacaaa    600

ccaaccgtca aaaccacaaa caaaagagac ccaaaaacac cagccaaaat gatgaaaaaa    660

gaaaccacca ccaacccaac aaaaaaacca accctcaaga ccacagaagg agacaccagc    720

acctcacaat ccactgtgct cgacacaacc acatcaaaac acacaatcca acagcaatcc    780

ctccactcaa tcacctccga aaacacaccc aactccacac aaatacccac agcaaccgag    840

gcctccacat caaattctac ttaaaaaa                                       868
```

<210> SEQ ID NO 15
<211> LENGTH: 218
<212> TYPE: DNA
<213> ORGANISM: respiratory syncytial virus B 9320

<400> SEQUENCE: 15

```
attggcatta agcctacaaa acacactcct ataatataca aatatgacct caacccgtaa     60

attccaacaa aaaactaacc catccaaact aagctattcc ttaaataaca gtgctcaaca    120
```

-continued gttaagaagg ggctaatcca ttttagtaat taaaaataaa ggtaaagcca ataacataaa 180
ttggggcaaa tacaaagatg gctcttagca aagtcaag 218

<210> SEQ ID NO 16
<211> LENGTH: 35
<212> TYPE: DNA
<213> ORGANISM: Artificial
<220> FEATURE:
<223> OTHER INFORMATION: oligonucleotide primer; BglIIsite, RSV B 9320 G

<400> SEQUENCE: 16
gatatcaaga tctacaataa cattggggca aatgc 35

<210> SEQ ID NO 17
<211> LENGTH: 31
<212> TYPE: DNA
<213> ORGANISM: Artificial
<220> FEATURE:
<223> OTHER INFORMATION: oligonucleotide primer; BglIIsite, RSV B 9320 G

<400> SEQUENCE: 17
gctaagagat ctttttgaat aactaagcat g 31

<210> SEQ ID NO 18
<211> LENGTH: 36
<212> TYPE: DNA
<213> ORGANISM: Artificial
<220> FEATURE:
<223> OTHER INFORMATION: oligonucleotide primer; BamHIsite, RSV B 9320

<400> SEQUENCE: 18
atcaggatcc acaataacat tggggcaaat gcaacc 36

<210> SEQ ID NO 19
<211> LENGTH: 36
<212> TYPE: DNA
<213> ORGANISM: Artificial
<220> FEATURE:
<223> OTHER INFORMATION: oligonucleotide primer; BamHI site, RSV 9320 G

<400> SEQUENCE: 19
ctggcattcg gatccgtttt atgtaactat gagttg 36

<210> SEQ ID NO 20
<211> LENGTH: 27
<212> TYPE: DNA
<213> ORGANISM: Artificial
<220> FEATURE:
<223> OTHER INFORMATION: oligonucleotide primer

<400> SEQUENCE: 20
gatcccatgg ctcttagcaa agtcaag 27

<210> SEQ ID NO 21
<211> LENGTH: 31
<212> TYPE: DNA
<213> ORGANISM: Artificial
<220> FEATURE:
<223> OTHER INFORMATION: oligonucleotide primer

<400> SEQUENCE: 21
gtacggatcc gttgacttat ttgccccgta t 31

<210> SEQ ID NO 22

-continued

<211> LENGTH: 25
<212> TYPE: DNA
<213> ORGANISM: Artificial
<220> FEATURE:
<223> OTHER INFORMATION: oligonucleotide primer

<400> SEQUENCE: 22
gatcccatgg agaagtttgc acctg 25

<210> SEQ ID NO 23
<211> LENGTH: 28
<212> TYPE: DNA
<213> ORGANISM: Artificial
<220> FEATURE:
<223> OTHER INFORMATION: oligonucleotide primer

<400> SEQUENCE: 23
gtacggatcc tgagtgagtt gatcactg 28

<210> SEQ ID NO 24
<211> LENGTH: 28
<212> TYPE: DNA
<213> ORGANISM: Artificial
<220> FEATURE:
<223> OTHER INFORMATION: oligonucleotide primer

<400> SEQUENCE: 24
gcttggccat aacgattcta tatcatcc 28

<210> SEQ ID NO 25
<211> LENGTH: 26
<212> TYPE: DNA
<213> ORGANISM: Artificial
<220> FEATURE:
<223> OTHER INFORMATION: oligonucleotide primer

<400> SEQUENCE: 25
ggtagtataa tgttgtgcac ttttag 26

<210> SEQ ID NO 26
<211> LENGTH: 25
<212> TYPE: DNA
<213> ORGANISM: Artificial
<220> FEATURE:
<223> OTHER INFORMATION: oligonucleotide primer

<400> SEQUENCE: 26
ggtcacgatt tacaagataa gctcc 25

<210> SEQ ID NO 27
<211> LENGTH: 30
<212> TYPE: DNA
<213> ORGANISM: Artificial
<220> FEATURE:
<223> OTHER INFORMATION: oligonucleotide primer

<400> SEQUENCE: 27
cagatccttt taacttgcta cctaggcaca 30

<210> SEQ ID NO 28
<211> LENGTH: 23
<212> TYPE: DNA
<213> ORGANISM: Artificial
<220> FEATURE:
<223> OTHER INFORMATION: oligonucleotide primer

<400> SEQUENCE: 28

-continued cttacgtgtg cctaggtagc aag 23

<210> SEQ ID NO 29
<211> LENGTH: 33
<212> TYPE: DNA
<213> ORGANISM: Artificial
<220> FEATURE:
<223> OTHER INFORMATION: oligonucleotide primer

<400> SEQUENCE: 29
acgagaaaaa aagtgtcaaa aactaatgtc tcg 33

<210> SEQ ID NO 30
<211> LENGTH: 42
<212> TYPE: DNA
<213> ORGANISM: Artificial
<220> FEATURE:
<223> OTHER INFORMATION: oligonucleotide primer

<400> SEQUENCE: 30
gtttttgaca ctttttttct cgtggccggc atggtcccag cc 42

<210> SEQ ID NO 31
<211> LENGTH: 33
<212> TYPE: DNA
<213> ORGANISM: Artificial
<220> FEATURE:
<223> OTHER INFORMATION: oligonucleotide primer

<400> SEQUENCE: 31
gatctagagc tccaagcttg cggccgcgtc gac 33

<210> SEQ ID NO 32
<211> LENGTH: 46
<212> TYPE: DNA
<213> ORGANISM: Artificial
<220> FEATURE:
<223> OTHER INFORMATION: oligonucleotide primer

<400> SEQUENCE: 32
gggtaccccc gggtaatacg actcactata gggacgggaa aaaatg 46

<210> SEQ ID NO 33
<211> LENGTH: 24
<212> TYPE: DNA
<213> ORGANISM: Artificial
<220> FEATURE:
<223> OTHER INFORMATION: oligonucleotide primer

<400> SEQUENCE: 33
gttaacttag agctctacat catc 24

<210> SEQ ID NO 34
<211> LENGTH: 24
<212> TYPE: DNA
<213> ORGANISM: Artificial
<220> FEATURE:
<223> OTHER INFORMATION: oligonucleotide primer

<400> SEQUENCE: 34
gtgtggtcct aggcaatgca gcag 24

<210> SEQ ID NO 35
<211> LENGTH: 29
<212> TYPE: DNA

-continued

<213> ORGANISM: Artificial
<220> FEATURE:
<223> OTHER INFORMATION: oligonucleotide primer

<400> SEQUENCE: 35
gacacagcat gatggtagag ctctatgtg 29

<210> SEQ ID NO 36
<211> LENGTH: 28
<212> TYPE: DNA
<213> ORGANISM: Artificial
<220> FEATURE:
<223> OTHER INFORMATION: oligonucleotide primer

<400> SEQUENCE: 36
gctaagtgaa cataaaacat tctgtaac 28

<210> SEQ ID NO 37
<211> LENGTH: 26
<212> TYPE: DNA
<213> ORGANISM: Artificial
<220> FEATURE:
<223> OTHER INFORMATION: oligonucleotide primer

<400> SEQUENCE: 37
ccattaataa tgggatccat tttgtc 26

<210> SEQ ID NO 38
<211> LENGTH: 29
<212> TYPE: DNA
<213> ORGANISM: Artificial
<220> FEATURE:
<223> OTHER INFORMATION: oligonucleotide primer

<400> SEQUENCE: 38
cacatagagc tctaccatca tgctgtgtc 29

<210> SEQ ID NO 39
<211> LENGTH: 27
<212> TYPE: DNA
<213> ORGANISM: Artificial
<220> FEATURE:
<223> OTHER INFORMATION: oligonucleotide primer

<400> SEQUENCE: 39
cattaatgag ggacccacag gctttag 27

<210> SEQ ID NO 40
<211> LENGTH: 27
<212> TYPE: DNA
<213> ORGANISM: Artificial
<220> FEATURE:
<223> OTHER INFORMATION: oligonucleotide primer

<400> SEQUENCE: 40
ctaaagcctg tgggtccctc attaatg 27

<210> SEQ ID NO 41
<211> LENGTH: 32
<212> TYPE: DNA
<213> ORGANISM: Artificial
<220> FEATURE:
<223> OTHER INFORMATION: oligonucleotide primer

<400> SEQUENCE: 41
catggttaat acactggttc aatttatata ca 32

-continued

<210> SEQ ID NO 42
<211> LENGTH: 32
<212> TYPE: DNA
<213> ORGANISM: Artificial
<220> FEATURE:
<223> OTHER INFORMATION: oligonucleotide primer

<400> SEQUENCE: 42
tgtatataaa ttgaaccagt gtattaacca tg 32

<210> SEQ ID NO 43
<211> LENGTH: 41
<212> TYPE: DNA
<213> ORGANISM: Artificial
<220> FEATURE:
<223> OTHER INFORMATION: oligonucleotide primer

<400> SEQUENCE: 43
gtcttaaaaa acgaaataaa acgctacaag ggcctcatac c 41

<210> SEQ ID NO 44
<211> LENGTH: 41
<212> TYPE: DNA
<213> ORGANISM: Artificial
<220> FEATURE:
<223> OTHER INFORMATION: oligonucleotide primer

<400> SEQUENCE: 44
ggtatgaggc ccttgtagcg ttttatttcg ttttttaaga c 41

<210> SEQ ID NO 45
<211> LENGTH: 24
<212> TYPE: DNA
<213> ORGANISM: Artificial
<220> FEATURE:
<223> OTHER INFORMATION: oligonucleotide primer

<400> SEQUENCE: 45
gatgatgtag agctttaagt taac 24

<210> SEQ ID NO 46
<211> LENGTH: 24
<212> TYPE: DNA
<213> ORGANISM: Artificial
<220> FEATURE:
<223> OTHER INFORMATION: oligonucleotide primer

<400> SEQUENCE: 46
gttaacttaa agctctacat catc 24

<210> SEQ ID NO 47
<211> LENGTH: 44
<212> TYPE: DNA
<213> ORGANISM: Artificial
<220> FEATURE:
<223> OTHER INFORMATION: oligonucleotide primer

<400> SEQUENCE: 47
ctaactggta aagaaagaga gcttagtgta ggtagaatgt ttgc 44

<210> SEQ ID NO 48
<211> LENGTH: 44
<212> TYPE: DNA
<213> ORGANISM: Artificial
<220> FEATURE:

-continued

<223> OTHER INFORMATION: oligonucleotide primer

<400> SEQUENCE: 48
gcaaacattc tacctacact aagctctctt tctttaccag ttag 44

<210> SEQ ID NO 49
<211> LENGTH: 40
<212> TYPE: DNA
<213> ORGANISM: Artificial
<220> FEATURE:
<223> OTHER INFORMATION: oligonucleotide primer

<400> SEQUENCE: 49
gtttaacaac caatgagctt aaaaagctga ttaaaattac 40

<210> SEQ ID NO 50
<211> LENGTH: 40
<212> TYPE: DNA
<213> ORGANISM: Artificial
<220> FEATURE:
<223> OTHER INFORMATION: oligonucleotide primer

<400> SEQUENCE: 50
gtaattttaa tcagcttttt aagctcattg gttgttaaac 40

<210> SEQ ID NO 51
<211> LENGTH: 23
<212> TYPE: DNA
<213> ORGANISM: Artificial
<220> FEATURE:
<223> OTHER INFORMATION: oligonucleotide primer

<400> SEQUENCE: 51
cggtctaatg gatgataatt gtg 23

<210> SEQ ID NO 52
<211> LENGTH: 23
<212> TYPE: DNA
<213> ORGANISM: Artificial
<220> FEATURE:
<223> OTHER INFORMATION: oligonucleotide primer

<400> SEQUENCE: 52
atgaagctac tgcacaaagt agg 23

<210> SEQ ID NO 53
<211> LENGTH: 27
<212> TYPE: DNA
<213> ORGANISM: Artificial
<220> FEATURE:
<223> OTHER INFORMATION: oligonucleotide primer

<400> SEQUENCE: 53
gtaatcatct tttggttttt ttggtgg 27

<210> SEQ ID NO 54
<211> LENGTH: 33
<212> TYPE: DNA
<213> ORGANISM: Artificial
<220> FEATURE:
<223> OTHER INFORMATION: oligonucleotide primer

<400> SEQUENCE: 54
ccaaccatca aacccacaaa caaaccaacc gtc 33

NUCLEIC ACIDS ENCODING RESPIRATORY SYNCYTIAL VIRUS SUBGROUP B STRAIN 9320

CROSS REFERENCE TO RELATED APPLICATIONS

This application is a non-provisional utility patent application claiming priority to and benefit of the following prior provisional patent applications: U.S. Ser. No. 60/458,331, filed Mar. 28, 2003, entitled "Compositions and Methods Involving Respiratory Syncytial Virus Subgroup B Strain 9320" by Xing Cheng, et al., and U.S. Ser. No. 60/508,320, filed Oct. 3, 2003, entitled "Compositions and Methods Involving Respiratory Syncytial Virus Subgroup B Strain 9320" by Xing Cheng, et al., each of which is incorporated herein by reference in its entirety for all purposes.

FIELD OF THE INVENTION

The present invention is in the field of virology. More specifically, the invention relates to human respiratory syncytial virus, including the diagnosis, treatment, and prevention of human RSV infections.

BACKGROUND OF THE INVENTION

Human Respiratory Syncytial Virus (RSV) is the leading cause of hospitalization for viral respiratory tract disease (e.g., bronchiolitis and pneumonia) in infants and young children worldwide, as well as a significant source of morbidity and mortality in immunocompromised adults and in the elderly (see, e.g., Shay et al. (1999) "Bronchiolitis-associated hospitalizations among U.S. children, 1980-1996" *JAMA* 282:1440-1446, Falsey et al. (1995) "Respiratory syncytial virus and influenza A infections in the hospitalized elderly" *J Infect Dis* 172:389-394, Falsey et al. (1992) "Viral respiratory infections in the institutionalized elderly: clinical and epidemiologic findings" *J Am Geriatr Soc* 40:115-119, Falsey and Walsh (1998) "Relationship of serum antibody to risk of respiratory syncytial virus infection in elderly adults" *J Infect Dis* 177:463-466, Hall et al. (1986) "Respiratory syncytial viral infection in children with compromised immune function" *N Engl J Med* 315:77-81, and Harrington et al. (1992) "An outbreak of respiratory syncytial virus in a bone marrow transplant center" *J Infect Dis* 165:987-993). To date, no vaccines have been approved which are able to prevent the diseases associated with RSV infection. RSV is an enveloped virus that has a single-stranded negative sense non-segmented RNA genome, and it is classified in the Pneumovirus genus of the Paramyxoviridae family (Collins et al. (2001) Respiratory syncytial virus. pp. 1443-1485. In; Knipe and Howley (eds.) *Fields Virology vol.* 1. Lippincott, Williams and Wilkins, Philadelphia; Lamb and Kolakofsky (2001) *Paramyxoviridae: the viruses and their replication* pp. 1305-1340. In; Knipe and Howley (eds.) *Fields Virology* vol. 1. Lippincott, Williams and Wilkins, Philadelphia). Human RSV is classified into two subgroups, subgroups A and B, based on antigenic diversity and nucleotide sequence divergence. For example, the attachment protein G is most divergent and the fusion protein F is relatively conserved between the two subgroups.

Considerable progress has been made towards understanding the molecular biology of subgroup A RSV; however, much less information is available for subgroup B RSV. Most work to date has focused on subgroup A strains. For example, RSV strain A2 has been sequenced. The genome of the A2 strain RSV is 15,222 nt in length and contains 10 transcriptional units that encode 11 proteins (NS1, NS2, N, P, M, SH, G, F, M2-1, M2-2, and L). The genome is tightly bound by the N protein to form the nucleocapsid, which is the template for the viral RNA polymerase comprising the N, P and L proteins (Grosfeld et al. (1995) *J. Virol.* 69:5677-5686; Yu et al. (1995) *J. Virol.* 69:2412-2419). Each transcription unit is flanked by a highly conserved 10-nt gene-start (GS) signal, at which mRNA synthesis begins, and ends with a semiconserved 12- to 13-nt gene-end (GE) signal that directs polyadenylation and release of mRNAs (Harmon et al. (2001) *J. Virol.* 75:36-44; Kuo et al. (1996) *J. Virol.* 70:6892-6901). Transcription of RSV genes is sequential, and there is a gradient of decreasing mRNA synthesis due to transcription attenuation (Barik (1992) *J. Virol.* 66:6813-6818; Dickens et al. (1984) *J. Virol.* 52:364-369). The viral RNA polymerase must first terminate synthesis of the upstream message in order to initiate synthesis of the downstream mRNA.

The nucleocapsid protein (N), phosphoprotein (P), and large polymerase protein (L) constitute the minimal components for viral RNA replication and transcription in vitro (Grosfield et al. (1995) *J. Virol.* 69:5677-5686; Yu et al. (1995) *J. Virol.* 69:2412-2419). The N protein associates with the genomic RNA to form the nucleocapsid, which serves as the template for RNA synthesis. The L protein is a multifunctional protein that contains RNA-dependent RNA polymerase catalytic motifs and is also probably responsible for capping and polyadenylation of viral mRNAs. However, the L protein alone is not sufficient for the polymerase function; the P protein is also required. Transcription and replication of RSV RNA are also modulated by the M2-1, M2-2, NS1, and NS2 proteins that are unique to the pneumoviruses. M2-1 is a transcription antitermination (or elongation) factor required for processive RNA synthesis and transcription read-through at gene junctions, essential for RNA transcription and virus replication (Collins et al. (1996) "Transcription elongation factor of respiratory syncytial virus, a nonsegmented negative-strand RNA virus" *Proc Natl Acad Sci USA* 93:81-85; Hardy and Wertz (2000) "The Cys3-His1 motif of the respiratory syncytial virus M2-1 protein is essential for protein function" *J Virol* 74:5880-5885; Tang et al. (2001) "Requirement of cysteines and length of the human respiratory syncytial virus M2-1 protein for protein function and virus viability" *J Virol* 75:11328-11335; Collins et al. (2001) in D. M. Knipe et al. (eds.), *Fields Virology*, $4^{th}$ ed. Lippincott, Philadelphia; Hardy et al. (1999) *J. Virol.* 73:170-176; and Hardy and Wertz (1998) *J. Virol.* 72:520-526). M2-2, though not essential for virus replication in tissue culture, is involved in the switch between viral RNA transcription and replication (Bermingham and Collins (1999) *Proc. Natl. Acad. Sci. USA* 96:11259-11264; Jin et al. (2000) *J. Virol.* 74:74-82). NS1 and NS2 have been shown to inhibit minigenome synthesis in vitro (Atreya et al. (1998) *J. Virol.* 72:1452-1461).

NS1, NS2, SH, M2-2 and G are accessory proteins that can be deleted from the RSV A2 strain without affecting virus viability (Bermingham and Collins (1999) *Proc. Natl. Acad. Sci. USA* 96:11259-11264; Jin et al. (2000) *J. Virol.* 74:74-82; Jin et al. (2000) "Recombinant respiratory syncytial viruses with deletions in the NS1, NS2, SH, and M2-2 genes are attenuated in vitro and in vivo" *Virology* 273:210-218; Bukreyev et al. (1997) "Recombinant respiratory syncytial virus from which the entire SH gene has been deleted grows efficiently in cell culture and exhibits site- specific attenuation in the respiratory tract of the mouse" *J Virol* 71:8973-8982; Teng and Collins (1999) "Altered growth characteristics of recombinant respiratory syncytial viruses which do not produce NS2 protein" *J Virol* 73:466-473; Teng et al. (2000)

"Recombinant respiratory syncytial virus that does not express the NS1 or M2-2 protein is highly attenuated and immunogenic in chimpanzees" *J Virol* 74:9317-9321; Karron et al. (1997) "Respiratory syncytial virus (RSV) SH and G proteins are not essential for viral replication in vitro: clinical evaluation and molecular characterization of a cold-passaged, attenuated RSV subgroup B mutant" *Proc Natl Acad Sci USA* 94:13961-13966). However, except for the SH deletion mutant, most of the gene deletion mutants do not replicate as well as the wild type RSV either in tissue culture or in animal hosts.

The G and F proteins are the two major surface antigens that elicit anti-RSV neutralizing antibodies to provide protective immunity against RSV infection and reinfection. High levels of circulating antibodies correlate with protection against RSV infections or reduction of disease severity (Crowe (1999) *Microbiol. Immunol.* 236:191-214). As noted, two antigenic RSV subgroups (A and B) have been recognized based on virus antigenic and sequence divergence (Anderson et al. (1985) *J. Infect. Dis.* 151:626-633; Mufson et al. (1985) *J. Gen. Virol.* 66:2111-2124). By using a reciprocal cross-neutralization assay, it has been determined that the F proteins between the two subgroups are 50% related and the G proteins are only 1-7% related (reviewed by Collins et al. (2001) "Respiratory syncytial virus" In: D. M. Knipe et al. (Ed) *Fields Virology*, pp. 1443-1485, Vol. 1, Lippincott Williams & Wilkins, Philadelphia). This antigenic diversity may be partly responsible for repeated RSV infection. The antigenic diversity of these two RSV subgroups enables viruses from both subgroups to circulate concurrently in a community, and the prevalence of each subgroup can alternate during successive years. Epidemic studies of RSV infection in children have suggested that naturally acquired infection elicits a relatively higher protection against disease caused by the homologous subgroup virus (McIntosh and Chanock (1990) "Respiratory syncytial virus" In: D. M. Knipe et al. (Ed) *Second Edition Virology*, pp. 1045-1072, Raven Press, Ltd., New York). The immunity induced by RSV infection is transient and subsequent reinfection can occur. However, RSV reinfection usually does not cause severe disease. An RSV vaccine is therefore typically targeted to provide protection against severe lower respiratory disease caused by RSV subgroup A and B viruses.

Efforts to produce a safe and effective RSV vaccine have focused on the administration of purified viral antigen or the development of live attenuated RSV for intranasal administration. For example, a formalin-inactivated virus vaccine not only failed to provide protection against RSV infection, but was shown to exacerbate symptoms during subsequent infection by the wild-type virus in infants (Kapikian et al. (1969) *Am. J. Epidemiol.* 89:405-421; Chin et al. (1969) *Am. J. Epidemiol.* 89:449-63). More recently, efforts have been aimed towards developing live attenuated temperature-sensitive mutants by chemical mutagenesis or cold passage of the wild-type RSV (Crowe et al. (1994) *Vaccine* 12:691-9). Typically, the virus candidates have been either underattenuated or overattenuated (Kim et al. (1973) *Pediatrics* 52:56-63; Wright et al. (1976) *J. Pediatrics* 88:931-6), and some of the candidates were genetically unstable, resulting in the loss of the attenuated phenotype (Hodges et al. (1974) *Proc Soc. Exp. Bio. Med.* 145:1158-64). To date, no live attenuated vaccine has been brought to market.

Characterization of additional strains of RSV, particularly from subgroup B, will assist in production of effective vaccines (e.g., regions of homology or identity between strains can indicate functionally conserved regions that can be targeted by mutagenesis). Although short regions of various subgroup B strains have been sequenced (e.g., B9320 protein G, SEQ ID NO:14, from GenBank accession number M73544; a B9320 intergenic region, SEQ ID NO:15, from GenBank accession number S75820; B9320 G and F gene start and end sequences, SEQ ID NOs:16-19, from Jin et al. (1998) *Virology* 251:206-214 and Cheng et al. (2001) *Virology* 283:59-68; and various B18537 coding and intergenic regions, GenBank accession numbers D00334, D00392-D00397, D00736, D01042, and M17213), only one subgroup B strain, strain B1, has been sequenced in its entirety (SEQ ID NO:13, from GenBank accession number AF013254).

Accordingly, this invention presents the complete polynucleotide sequence of human RSV subgroup B strain 9320. Polypeptides encoded by the B9320 genome are also provided, as are other benefits which will become apparent upon review of the disclosure.

SUMMARY OF THE INVENTION

The present invention provides the complete polynucleotide sequence of human respiratory syncytial virus subgroup B strain 9320. Amino acid sequences of proteins encoded by the B9320 genome are also provided. The invention provides isolated or recombinant nucleic acids and polypeptides comprising the novel B9320 sequences. Isolated or recombinant RSV comprising the nucleic acids and polypeptides of the invention (e.g., attenuated recombinant RSV) are also provided, as are immunogenic compositions including such nucleic acids, polypeptides, and RSV that are suitable for use as vaccines. Recovery of infectious recombinant 9320 viruses from cDNAs is described.

In a first aspect, the present invention provides isolated or recombinant nucleic acids comprising a polynucleotide sequence of the invention. Thus, for example, an isolated or recombinant nucleic acid comprising the polynucleotide sequence of SEQ ID NO:1 or a complementary polynucleotide sequence thereof is a favored embodiment of the invention. An isolated or recombinant nucleic acid comprising at least one unique polynucleotide subsequence of SEQ ID NO:1 or a complementary polynucleotide sequence thereof, with the proviso that the unique polynucleotide subsequence includes at least one subsequence not included in SEQ ID NOs:14-19 or a complementary polynucleotide sequence thereof, is another favored embodiment. The unique polynucleotide subsequence can, for example, comprise at least 10 contiguous nucleotides of SEQ ID NO:1 or a complementary polynucleotide sequence thereof (e.g., at least 20 contiguous nucleotides, at least 50 contiguous nucleotides, at least 100 contiguous nucleotides, at least 500 contiguous nucleotides, or even at least 1000 contiguous nucleotides). In some embodiments, the polynucleotide subsequence includes at least one compete open reading frame (ORF) of SEQ ID NO:1.

In addition to the sequences explicitly provided in the accompanying sequence listing, polynucleotide sequences that are highly related structurally and/or functionally (e.g., as defined by hybridization and/or sequence identity) are polynucleotides of the invention. For example, a polynucleotide sequence that is greater than 97.8% identical to SEQ ID NO:1 or a complementary polynucleotide sequence thereof, as determined by BLASTN using default parameters, is a polynucleotide of the invention. As another example, a polynucleotide sequence that hybridizes under stringent conditions over substantially the entire length of a polynucleotide subsequence comprising at least 100 contiguous nucleotides of SEQ ID NO:1 or a complementary polynucleotide sequence thereof, wherein the polynucleotide sequence hybridizes to the polynucleotide subsequence of SEQ ID NO:1 or the complementary polynucleotide sequence thereof under said stringent conditions with at least 2× a signal to noise ratio that the polynucleotide sequence hybridizes to a corresponding polynucleotide subsequence of SEQ ID NO:13 or a complementary polynucleotide sequence thereof, is a polynucleotide sequence of the invention. Similarly, polynucleotide sequences of the invention include a polynucleotide sequence encoding a polypeptide of the invention, e.g., encoding an amino acid sequence or unique subsequence selected from the group consisting of SEQ ID NOs:2-11 or an artificial conservative variation thereof.

A nucleic acid of the invention optionally comprises at least one artificially mutated nucleotide, e.g., at least one artificially deleted, inserted, and/or substituted nucleotide. In certain embodiments, mutation of the polynucleotide sequence results in alteration of an encoded amino acid sequence. Thus, in one class of embodiments, at least one polypeptide encoded by the nucleic acid comprises at least one deleted, inserted, and/or substituted amino acid residue (e.g., at least one conservatively or non-conservatively substituted amino acid residue). For example, the mutated nucleotide can be located in an ORF encoding a polypeptide selected from SEQ ID NOs:2-12.

Another class of embodiments provides vectors comprising the nucleic acids of the invention. Yet another class of embodiments provides a host cell into which such a vector has been introduced. Another class of embodiments provides methods of producing a recombinant respiratory syncytial virus. In the methods, such a host cell is cultured in a suitable culture medium under conditions permitting expression of the nucleic acid, and the recombinant respiratory syncytial virus is isolated from the host cell and/or the medium. Recombinant RSV produced according to these methods form another feature of the invention, as do recombinant RSV comprising a nucleic acid of the invention. A related class of embodiments provides methods of producing an isolated or recombinant polypeptide. In the methods, a host cell comprising a vector that includes a nucleic acid of the invention is cultured in a suitable culture medium under conditions permitting expression of the nucleic acid, and the polypeptide is isolated from the host cell and/or the medium. Polypeptides produced according to these methods form another feature of the invention, as do polypeptides comprising an amino acid sequence or subsequence that is encoded by a nucleic acid of the invention.

One aspect of the invention provides isolated or recombinant polypeptides comprising an amino acid sequence of the invention. Thus, for example, an isolated or recombinant polypeptide comprising an amino acid sequence selected from the group consisting of SEQ ID NOs:2-11 is a favored embodiment of the invention. An isolated or recombinant polypeptide comprising a unique amino acid subsequence comprising at least 7 (e.g., at least 8, at least 10, at least 20, at least 50, or more) contiguous amino acid residues of any one of SEQ ID NOs:2-11 is another favored embodiment. Artificial conservative variations of amino acid sequences or subsequences of the invention are also amino acid sequences of the invention, as are amino acid sequences that are substantially identical to an amino acid sequence of the invention. For example, an amino acid sequence that is greater than 99.3% identical to SEQ ID NO:2, greater than 98.4% identical to SEQ ID NO:3, greater than 99.7% identical to SEQ ID NO:4, greater than 98.3% identical to SEQ ID NO:5, greater than 99.6% identical to SEQ ID NO:6, greater than 97.0% identical to SEQ ID NO:7, greater than 99.3% identical to SEQ ID NO:8, greater than 99.5% identical to SEQ ID NO:9, greater than 96.4% identical to SEQ ID NO:10, or greater than 99.2% identical to SEQ ID NO:11, as determined by BLASTP using default parameters, is an amino acid sequence of the invention. Similarly, an amino acid sequence or subsequence that is specifically bound by an antibody that specifically binds to an amino acid sequence or subsequence encoded by SEQ ID NO:1, wherein said antibody does not specifically bind to an amino acid sequence or subsequence encoded by SEQ ID NO:13 or SEQ ID NO:14, is an amino acid sequence of the invention.

A polypeptide of the invention optionally comprises at least one artificially altered amino acid, e.g., at least one deleted, inserted, and/or substituted amino acid. For example, one class of embodiments provides an isolated or recombinant polypeptide comprising the amino acid sequence of SEQ ID NO:12 with a deletion of residues 164-197, or an artificial conservative variation thereof.

Immunogenic compositions comprising an immunologically effective amount of a recombinant respiratory syncytial virus, polypeptide, and/or nucleic acid of the invention form another aspect of the invention. Similarly, another feature of the invention provides methods for stimulating the immune system of an individual to produce a protective immune response against respiratory syncytial virus. In the methods, an immunologically effective amount of a respiratory syncytial virus, polypeptide, and/or nucleic acid of the invention is administered to the individual in a physiologically acceptable carrier.

DEFINITIONS

Figure 1:
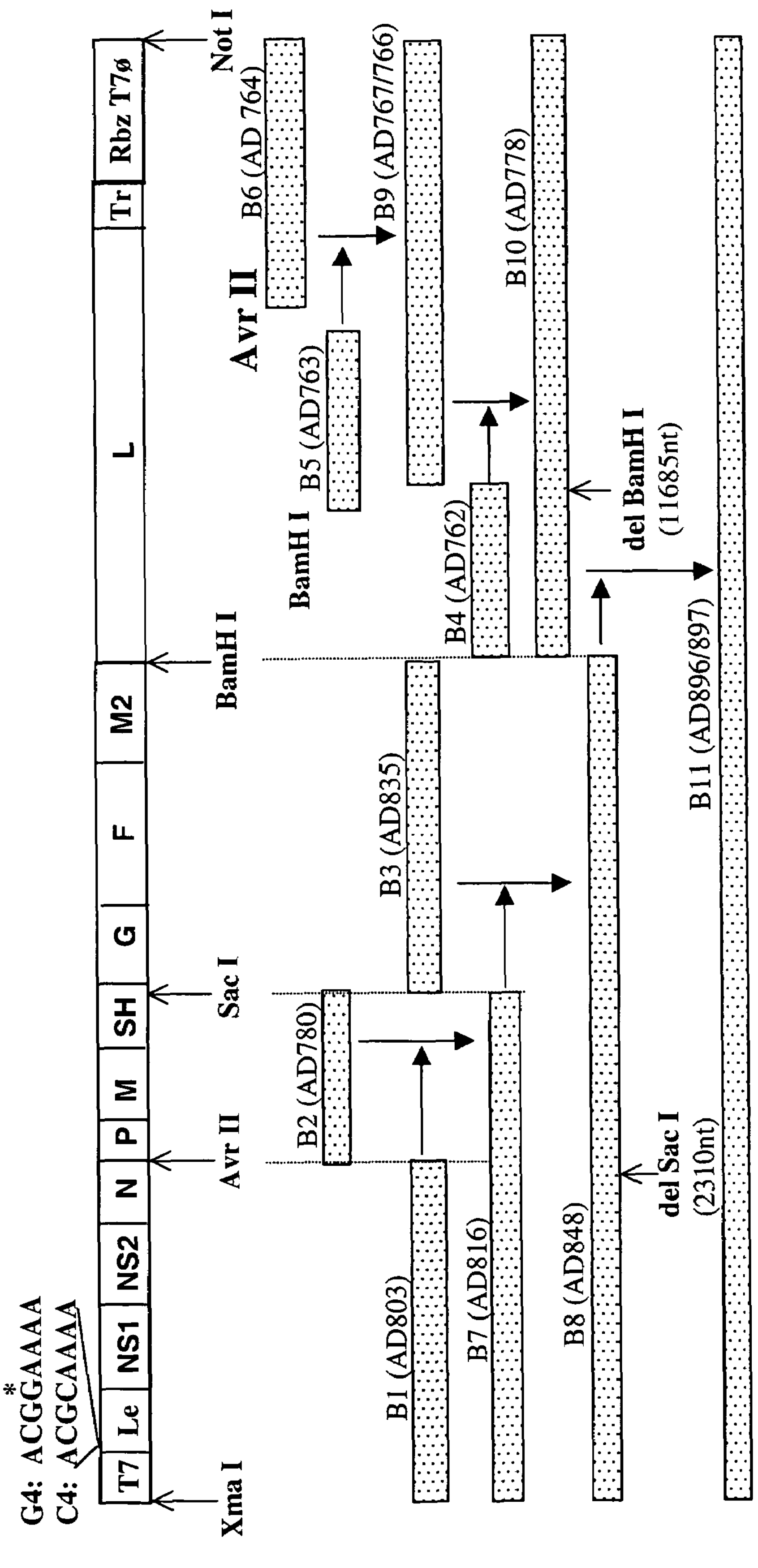
FIG. 1 schematically illustrates assembly of the full-length antigenomic RSV 9320 cDNA. Positions of various subclones used to assemble the full length antigenomic cDNA are indicated. The cDNA fragments obtained by RT/PCR were ligated through the indicated restriction enzyme sites. The fourth residue of the leader sequence at the antigenomic sense was either C (SEQ ID NO:56) or G (SEQ ID NO:55) as indicated.

Unless defined otherwise, all technical and scientific terms used herein have the same meaning as commonly understood by one of ordinary skill in the art to which the invention pertains. The following definitions supplement those in the art and are directed to the current application and are not to be imputed to any related or unrelated case, e.g., to any commonly owned patent or application. Although any methods and materials similar or equivalent to those described herein can be used in the practice for testing of the present invention, the preferred materials and methods are described herein.

Accordingly, the terminology used herein is for the purpose of describing particular embodiments only, and is not intended to be limiting.

As used in this specification and the appended claims, the singular forms "a," "an" and "the" include plural referents unless the context clearly dictates otherwise. Thus, for example, reference to "a virus" includes a plurality of viruses; reference to "a host cell" includes mixtures of host cells, and the like.

An "amino acid sequence" is a polymer of amino acid residues (a protein, polypeptide, etc.) or a character string representing an amino acid polymer, depending on context.

A "polynucleotide sequence" or "nucleotide sequence" is a polymer of nucleotides (an oligonucleotide, a DNA, a nucleic acid, etc.) or a character string representing a nucleotide polymer, depending on context. From any specified polynucleotide sequence, either the given nucleic acid or the complementary polynucleotide sequence (e.g., the complementary nucleic acid) can be determined.

A "subsequence" is any portion of an entire sequence, up to and including the complete sequence. Typically, a subsequence comprises less than the full-length sequence. A "unique subsequence" is a subsequence that is not found in any previously determined RSV polynucleotide or polypeptide sequence (e.g., the A2, B1, and B18537 sequences listed and/or referenced herein).

An "artificial mutation" is a mutation introduced by human intervention, e.g., under laboratory conditions. Thus, an "artificially mutated" nucleotide is a nucleotide that has been mutated as a result of human intervention, an "artificially altered" amino acid residue is a residue that has been altered as a result of human intervention, and an "artificial conservative variation" is a conservative variation that has been produced by human intervention. For example, a wild type virus (e.g., one circulating naturally among human hosts) or other parental strain of virus can be "artificially mutated" using recombinant DNA techniques to alter the viral genome (e.g., the viral genome can be altered by in vitro mutagenesis, or by exposing it to a chemical, ionizing radiation, or the like and then performing in vitro or in vivo selection for a temperature sensitive, cold sensitive, or otherwise attenuated strain of virus). As another example, a wild type protein can be "artificially altered" by artificially mutating the gene encoding that protein.

The term "variant" with respect to a polypeptide refers to an amino acid sequence that is altered by one or more amino acids with respect to a reference sequence. The variant can have "conservative" changes, wherein a substituted amino acid has similar structural or chemical properties, e.g., replacement of leucine with isoleucine. Alternatively, a variant can have "nonconservative" changes, e.g., replacement of a glycine with a tryptophan. Analogous minor variation can also include amino acid deletion or insertion, or both. Guidance in determining which amino acid residues can be substituted, inserted, or deleted without eliminating biological or immunological activity can be found using computer programs well known in the art, for example, DNASTAR software. Examples of conservative substitutions are also described below.

The term "nucleic acid" or "polynucleotide" encompasses any physical string of monomer units that can be corresponded to a string of nucleotides, including a polymer of nucleotides (e.g., a typical DNA or RNA polymer), PNAs, modified oligonucleotides (e.g., oligonucleotides comprising bases that are not typical to biological RNA or DNA in solution, such as 2'-O-methylated oligonucleotides), and the like. A nucleic acid can be e.g., single-stranded or double-stranded. Unless otherwise indicated, a particular nucleic acid sequence of this invention encompasses complementary sequences, in addition to the sequence explicitly indicated.

The term "gene" is used broadly to refer to any nucleic acid associated with a biological function. Thus, genes include coding sequences and/or the regulatory sequences required for their expression. The term "gene" applies to a specific genomic sequence, as well as to a cDNA or an mRNA encoded by that genomic sequence. Genes also include non-expressed nucleic acid segments that, for example, form recognition sequences for other proteins. Non-expressed regulatory sequences include "promoters" and "enhancers," to which regulatory proteins such as transcription factors bind, resulting in transcription of adjacent or nearby sequences.

"Expression of a gene" or "expression of a nucleic acid" means transcription of DNA into RNA (optionally including modification of the RNA, e.g., splicing), translation of RNA into a polypeptide (possibly including subsequent modification of the polypeptide, e.g., posttranslational modification), or both transcription and translation, as indicated by the context.

The term "vector" refers to the means by which a nucleic acid can be propagated and/or transferred between organisms, cells, or cellular components. Vectors include plasmids, viruses, bacteriophage, pro-viruses, phagemids, transposons, and artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not autonomously replicating. Most commonly, the vectors of the present invention are plasmids.

An "expression vector" is a vector, such as a plasmid, which is capable of promoting expression as well as replication of a nucleic acid incorporated therein. Typically, the nucleic acid to be expressed is "operably linked" to a promoter and/or enhancer, and is subject to transcription regulatory control by the promoter and/or enhancer.

The term "host cell" means a cell which contains a heterologous nucleic acid, such as a vector, and supports the replication and/or expression of the nucleic acid. Host cells can be prokaryotic cells such as *E. coli*, or eukaryotic cells such as yeast, insect, amphibian, avian or mammalian cells, including human cells. Exemplary host cells in the context of the invention include HEp-2 cells and Vero cells.

The term "introduced" when referring to a heterologous or isolated nucleic acid refers to the transfer of a nucleic acid into a eukaryotic or prokaryotic cell where the nucleic acid can be incorporated into the genome of the cell (e.g., chromosome, plasmid, plastid or mitochondrial DNA), converted into an autonomous replicon, or transiently expressed (e.g., transfected mRNA). The term includes such methods as "infection," "transfection," "transformation" and "transduction." In the context of the invention a variety of methods can be employed to introduce nucleic acids into host cells, including electroporation, calcium phosphate precipitation, lipid mediated transfection (lipofection), etc.

An "open reading frame" or "ORF" is a possible translational reading frame of DNA or RNA (e.g., of a gene), which is capable of being translated into a polypeptide. That is, the reading frame is not interrupted by stop codons. However, it should be noted that the term ORF does not necessarily indicate that the polynucleotide is, in fact, translated into a polypeptide.

A "polypeptide" is a polymer comprising two or more amino acid residues (e.g., a peptide or a protein). The polymer can optionally comprise modifications such as glycosylation or the like. The amino acid residues of the polypeptide can be natural or non-natural and can be unsubstituted, unmodified, substituted or modified.

The term "recombinant" indicates that the material (e.g., a virus, a nucleic acid, or a protein) has been artificially or synthetically (non-naturally) altered by human intervention. The alteration can be performed on the material within, or removed from, its natural environment or state. For example, a "recombinant nucleic acid" is one that is made by recombining nucleic acids, e.g., during cloning, DNA shuffling or other procedures, or by chemical or other mutagenesis; a "recombinant polypeptide" or "recombinant protein" is a polypeptide or protein which is produced by expression of a recombinant nucleic acid; and a "recombinant virus", e.g., a recombinant respiratory syncytial virus, is produced by the expression of a recombinant nucleic acid.

The term "isolated" refers to a biological material, such as a virus, a nucleic acid or a protein, which is substantially free from components that normally accompany or interact with it in its naturally occurring environment. The isolated material optionally comprises material not found with the material in its natural environment, e.g., a cell. For example, if the material is in its natural environment, such as a cell, the material has been placed at a location in the cell (e.g., genome or genetic element) not native to a material found in that environment. For example, a naturally occurring nucleic acid (e.g., a coding sequence, a promoter, an enhancer, etc.) becomes isolated if it is introduced by non-naturally occurring means to a locus of the genome (e.g., a vector, such as a plasmid or virus vector, or amplicon) not native to that nucleic acid. Such nucleic acids are also referred to as "heterologous" nucleic acids. An isolated virus, for example, is in an environment (e.g., a cell culture system, or purified from cell culture) other than the native environment of wild-type virus (e.g., the nasopharynx of an infected individual).

The term "chimeric" or "chimera," when referring to a virus, indicates that the virus includes genetic and/or polypeptide components derived from more than one parental viral strain or source. Similarly, the term "chimeric" or "chimera," when referring to a viral protein, indicates that the protein includes polypeptide components (i.e., amino acid subsequences) derived from more than one parental viral strain or source.

An RSV "having an attenuated phenotype" or an "attenuated" RSV exhibits a substantially lower degree of virulence as compared to a wild-type virus (e.g., one circulating naturally among human hosts). An attenuated RSV typically exhibits a slower growth rate and/or a reduced level of replication (e.g., a peak titer, e.g., in cell culture, in an animal model of infection, or in a human vacinee's nasopharynx, that is at least about ten fold, preferably at least about one hundred fold, less than that of a wild-type RSV).

An "immunologically effective amount" of RSV is an amount sufficient to enhance an individual's (e.g., a human's) own immune response against a subsequent exposure to RSV. Levels of induced immunity can be monitored, e.g., by measuring amounts of neutralizing secretory and/or serum antibodies, e.g., by plaque neutralization, complement fixation, enzyme-linked immunosorbent, or microneutralization assay.

A "protective immune response" against RSV refers to an immune response exhibited by an individual (e.g., a human) that is protective against serious lower respiratory tract disease (e.g., pneumonia and/or bronchiolitis) when the individual is subsequently exposed to and/or infected with wild-type RSV. In some instances, the wild-type (e.g., naturally circulating) RSV can still cause infection, particularly in the upper respiratory tract (e.g., rhinitis), but it can not cause a serious infection. Typically, the protective immune response results in detectable levels of host engendered serum and secretory antibodies that are capable of neutralizing virus of the same strain and/or subgroup (and possibly also of a different, non-vaccine strain and/or subgroup) in vitro and in vivo.

As used herein, an "antibody" is a protein comprising one or more polypeptides substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively. Antibodies exist as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the (Fab')2 dimer into a Fab' monomer. The Fab' monomer is essentially a Fab with part of the hinge region (see, Fundamental Immunology, W. E. Paul, ed., Raven Press, N.Y. (1999), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein, includes antibodies or fragments either produced by the modification of whole antibodies or synthesized de novo using recombinant DNA methodologies. Antibodies include, e.g., polyclonal antibodies, monoclonal antibodies, multiple or single chain antibodies, including single chain Fv (sFv or scFv) antibodies in which a variable heavy and a variable light chain are joined together (directly or through a peptide linker) to form a continuous polypeptide, and humanized or chimeric antibodies.

An "antigenome" is a polynucleotide that is complementary (typically, perfectly complementary) to a single-stranded viral (e.g., RSV) genome. Since RSV is a negative-sense RNA virus, the genome is the "antisense" strand, and the antigenome is the "sense" strand that corresponds to mRNA.

A variety of additional terms are defined or otherwise characterized herein.

DETAILED DESCRIPTION

The present invention provides the complete polynucleotide sequence of human RSV subgroup B strain 9320. The sequence of a B9320 antigenomic cDNA is listed as SEQ ID NO:1. As will be evident, the RSV genome is an RNA with a polynucleotide sequence complementary to that of SEQ ID NO:1.

The B9320 genome comprises 10 transcriptional units encoding 11 proteins. Amino acid sequences of the proteins are also provided: NS1 is listed as SEQ ID NO:2, NS2 as SEQ ID NO:3, N as SEQ ID NO:4, P as SEQ ID NO:5, M as SEQ ID NO:6, SH as SEQ ID NO:7, G as SEQ ID NO:12, F as SEQ ID NO:8, M2-1 as SEQ ID NO:9, M2-2 as SEQ ID NO:10, and L as SEQ ID NO:11.

The invention provides isolated or recombinant polynucleotides and polypeptides comprising the novel B9320 sequences. Recombinant RSV comprising the nucleic acids and/or polypeptides (e.g., attenuated recombinant RSV suitable for use in attenuated live viral vaccines) are also provided.

Polynucleotides of the Invention

One aspect of the present invention provides isolated or recombinant nucleic acids comprising a polynucleotide sequence of the invention. Polynucleotide sequences of the invention include the polynucleotide sequence represented by SEQ ID NO:1, with the caveat that SEQ ID NOs:14-19, representing limited subsequences of RSV B9320, have been previously described (e.g., in GenBank accession numbers M73544 and S75820; Jin et al. (1998) Virology 251:206-214; and Cheng et al. (2001) Virology 283:59-68). Thus, for example, an isolated or recombinant nucleic acid comprising the polynucleotide sequence of SEQ ID NO:1 or a complementary polynucleotide sequence thereof is a favored embodiment of the invention. An isolated or recombinant nucleic acid comprising at least one unique polynucleotide subsequence of SEQ ID NO:1 (e.g., a unique coding subsequence) or a complementary polynucleotide sequence thereof, with the proviso that the unique polynucleotide subsequence includes at least one subsequence not included in SEQ ID NOs:14-19 or a complementary polynucleotide sequence thereof, is another favored embodiment. The unique polynucleotide subsequence can, for example, comprise at least 10 contiguous nucleotides of SEQ ID NO:1 or a complementary polynucleotide sequence thereof (e.g., at least 20 contiguous nucleotides, at least 50 contiguous nucleotides, at least 100 contiguous nucleotides, at least 500 contiguous nucleotides, or even at least 1000 contiguous nucleotides).

In addition to the sequences explicitly provided in the accompanying sequence listing, polynucleotide sequences that are highly related structurally and/or functionally are polynucleotides of the invention. Thus, polynucleotide sequences of the invention include a polynucleotide sequence that hybridizes under stringent conditions over substantially the entire length of the polynucleotide sequence of SEQ ID NO:1 (or a complementary sequence thereof) with at least 2× a signal to noise ratio (e.g., at least 5× or at least 10× the signal to noise ratio) that the polynucleotide sequence hybridizes to the polynucleotide sequence of SEQ ID NO:13 or a complementary polynucleotide sequence thereof. Polynucleotide sequences of the invention also include a polynucleotide sequence that hybridizes under stringent conditions over substantially the entire length of a polynucleotide subsequence comprising at least 100 contiguous nucleotides of SEQ ID NO:1 or its complementary sequence (e.g., a unique subsequence) with at least 2× a signal to noise ratio (e.g., at least 5× or at least 10× the signal to noise ratio) that the polynucleotide sequence hybridizes to the corresponding subsequence of SEQ ID NO:13 or a complementary polynucleotide sequence thereof (or, optionally, the corresponding subsequence of a genome of another naturally occurring respiratory syncytial virus or a complementary polynucleotide sequence thereof).

Similarly, polynucleotide sequences of the invention include a polynucleotide sequence encoding an amino acid sequence or unique subsequence selected from the group consisting of SEQ ID NOs:2-11 or an artificial conservative variation thereof.

In addition to the polynucleotide sequences of the invention, e.g., listed in SEQ ID NO:1, polynucleotide sequences that are substantially identical to a polynucleotide of the invention can be used in the compositions and methods of the invention. Substantially identical or substantially similar polynucleotide sequences are defined as polynucleotide sequences that are identical, on a nucleotide by nucleotide basis, with at least a subsequence of a reference polynucleotide, e.g., selected from SEQ ID NO:1. Such polynucleotides can include, e.g., insertions, deletions, and substitutions relative to SEQ ID NO:1. For example, isolated or recombinant nucleic acids comprising polynucleotide sequences (or subsequences) having greater than 97.8% sequence identity to SEQ ID NO:1 or a complementary polynucleotide sequence thereof, as determined by BLASTN using default parameters, with the proviso that the polynucleotide sequence includes at least one subsequence not selected from SEQ ID NOs:14-19, are favored embodiments of the invention. For example, the polynucleotide sequences (or subsequences) can be at least 98.5% (e.g., at least 99.0%, at least 99.5%, or more) identical to SEQ ID NO:1 or a complementary polynucleotide sequence thereof.

The nucleic acids of the invention can be, e.g., single-stranded or double-stranded, and can be, e.g., a DNA (e.g., a cDNA), an RNA, or an artificial nucleic acid (e.g., a peptide nucleic acid). SEQ ID NO:1 presents the DNA sequence of the antigenomic B9320 cDNA; however, it will be understood that the complementary genomic polynucleotide sequence can readily be determined from SEQ ID NO:1 and that U in an RNA sequence corresponds to T in a DNA sequence.

Nucleic acids of the invention include nucleic acids encoding polypeptides of the invention. In one general class of embodiments, the nucleic acid comprises at least one unique polynucleotide subsequence of SEQ ID NO:1 (or a complementary polynucleotide sequence thereof) encoding at least 20 contiguous amino acid residues of any one of SEQ ID NOs:2-12 (e.g., at least 50, at least 100, at least 200, or more contiguous amino acid residues). In one class of embodiments, the unique polynucleotide subsequence comprises at least one complete ORF, preferably at least one complete ORF encoding a polypeptide selected from among SEQ ID NOs: 2-12. In some embodiments, the nucleic acid comprises a plurality of complete open reading frames.

A nucleic acid of the invention optionally comprises at least one artificially mutated nucleotide, e.g., at least one artificially deleted, inserted, and/or substituted nucleotide (e.g., in a noncoding region, e.g., a C to G change at the fourth position of the antigenomic sequence, and/or in a coding region). For example, the nucleic acid can comprise a plurality of artificially mutated nucleotides. The artificially mutated nucleotide(s) can be introduced by site-directed mutagenesis, chemical mutagenesis, or the like.

In certain embodiments, mutation of the polynucleotide sequence results in alteration of an encoded amino acid sequence. Thus, in one class of embodiments, at least one polypeptide encoded by the nucleic acid comprises at least one deleted, inserted, and/or substituted amino acid residue (e.g., at least one conservatively or non-conservatively substituted amino acid residue). For example, the mutated nucleotide can be located in an ORF encoding a polypeptide selected from SEQ ID NOs:2-12. Thus, in one class of example embodiments, the at least one artificially mutated nucleotide is located in the open reading frame encoding the polypeptide of SEQ ID NO:12. The artificially mutated nucleotide(s) can comprise, e.g., a deletion, e.g., a deletion resulting in a deletion of one or more amino acid residues from the G protein encoded by SEQ ID NO:12 (e.g., a deletion of residues 164-197), or a deletion resulting in a deletion of the open reading frame encoding G. In another class of example embodiments, the at least one artificially mutated nucleotide is located in the open reading frame encoding the polypeptide of SEQ ID NO:10. The artificially mutated nucleotide(s) can comprise, e.g., a deletion, e.g., a deletion resulting in a deletion of one or more amino acid residues from the M2-2 protein encoded by SEQ ID NO:10, or a deletion resulting in a deletion of the open reading frame encoding M2-2. As another example, at least one of the nucleotides encoding amino acid residue 1, amino acid residue 4 and/or amino acid residue 10 of M2-2 can be mutated (e.g., substituted or deleted, e.g., forcing use of the second and/or third start codon and resulting in a deletion of amino acid residues 1-3 or 1-9 of M2-2).

The nucleic acids of the invention include chimeric nucleic acids, for example, a nucleic acid comprising at least one subsequence of SEQ ID NO:1 or a complementary polynucleotide sequence thereof and at least one polynucleotide subsequence from a different strain of virus. The subsequence of SEQ ID NO:1 is preferably a unique polynucleotide subsequence that comprises at least 10 contiguous nucleotides of SEQ ID NO:1 or its complement and that includes at least one subsequence not included in SEQ ID NOs:14-19 or a complementary polynucleotide sequence thereof. The different strain of virus can be, e.g., a different strain of human RSV (e.g., A2, B1, or the like) or a different species of virus (e.g., another paramyxovirus, e.g., pneumonia virus of mice, bovine RSV, or metapneumovirus). Such chimeric nucleic acids can, for example, encode chimeric proteins and/or chimeric viruses (e.g., for use in vaccines to induce a protective immune response against one or more strains of RSV and/or another virus). For example, in certain embodiments, the nucleic acid comprises at least one complete open reading frame of SEQ ID NO:1 and at least one complete open reading frame of the different strain of virus.

Another class of embodiments provides vectors comprising the nucleic acids of the invention. Yet another class of embodiments provides a host cell into which such a vector has been introduced.

Polypeptides of the Invention

One aspect of the present invention provides RSV B9320 polypeptides and variants thereof, for example, a polypeptide comprising an amino acid sequence or subsequence that is encoded by a nucleic acid of the invention, with the proviso that the amino acid sequence or subsequence is not encoded by SEQ ID NO:14.

One general class of embodiments provides isolated or recombinant polypeptides comprising an amino acid sequence of the invention. Thus, for example, an isolated or recombinant polypeptide comprising an amino acid sequence selected from the group consisting of SEQ ID NOs:2-11 is a favored embodiment of the invention. An isolated or recombinant polypeptide comprising a unique amino acid subsequence comprising at least 7 (e.g., at least 8, at least 10, at least 20, at least 50, or more) contiguous amino acid residues of any one of SEQ ID NOs:2-11 is another favored embodiment. Artificial conservative variations of amino acid sequences or subsequences of the invention are also amino acid sequences of the invention. Such polypeptides are optionally immunogenic.

In addition to the amino acid sequences of the invention, e.g., listed in SEQ ID NOs:2-11, amino acid sequences that are substantially identical to an amino acid sequence of the invention can be used in the compositions and methods of the invention. Substantially identical or substantially similar polypeptide sequences are defined as amino acid sequences that are identical, on an amino acid by amino acid basis, with at least a subsequence of a reference polypeptide, e.g., selected from among SEQ ID NOs:2-11. Such amino acid sequences can include, e.g., insertions, deletions, and substitutions relative to SEQ ID NOs:2-11. For example, an isolated or recombinant polypeptide comprising an amino acid sequence that is greater than 99.3% identical to SEQ ID NO:2, an amino acid sequence that is greater than 98.4% identical to SEQ ID NO:3, an amino acid sequence that is greater than 99.7% identical to SEQ ID NO:4, an amino acid sequence that is greater than 98.3% identical to SEQ ID NO:5, an amino acid sequence that is greater than 99.6% identical to SEQ ID NO:6, an amino acid sequence that is greater than 97.0% identical to SEQ ID NO:7, an amino acid sequence that is greater than 99.3% identical to SEQ ID NO:8, an amino acid sequence that is greater than 99.5% identical to SEQ ID NO:9, an amino acid sequence that is greater than 96.4% identical to SEQ ID NO:10, or an amino acid sequence that is greater than 99.2% identical to SEQ ID NO:11, as determined by BLASTP using default parameters, is a favored embodiment of the invention. For example, the isolated or recombinant polypeptide can comprise an amino acid sequence (or subsequence) that is at least 99.5% identical to SEQ ID NO:2, at least 98.6% identical to SEQ ID NO:3, at least 99.9% identical to SEQ ID NO:4, at least 98.5% identical to SEQ ID NO:5, at least 99.8% identical to SEQ ID NO:6, at least 97.2% identical to SEQ ID NO:7, at least 99.5% identical to SEQ ID NO:8, at least 99.7% identical to SEQ ID NO:9, at least 96.6% identical to SEQ ID NO:10, or at least 99.4% identical to SEQ ID NO:11, as determined by BLASTP using default parameters.

A polypeptide of the invention optionally comprises at least one artificially altered amino acid, e.g., at least one deleted, inserted, and/or substituted amino acid. For example, the polypeptide can comprise a plurality of artificially altered amino acids.

One class of embodiments provides an isolated or recombinant polypeptide comprising the amino acid sequence of SEQ ID NO:12 with a deletion of residues 164-197, or an artificial conservative variation thereof.

Methods of producing isolated or recombinant polypeptides form another aspect of the invention. In the methods, a host cell into which a vector (e.g., an expression vector, e.g., an expression vector comprising one or more ORFs, or a vector comprising an entire viral genome or antigenome) comprising a nucleic acid of the invention has been introduced is cultured in a suitable culture medium under conditions permitting expression of the nucleic acid. The polypeptide is then isolated from the host cell and/or the medium. For example, the polypeptide can be purified from the host cell and/or the medium such that the resulting purified polypeptide is enriched at least 5× as compared to its initial state. Polypeptides produced according to the methods described herein are also features of the invention. Such polypeptides can comprise, e.g., subsequences (e.g., unique subsequences, immunogenic subsequences, etc.) of SEQ ID NOs:2-11 from a few amino acids (e.g., 7 or more, 10 or more, or 20 or more) up to the full length proteins.

Determining Sequence Relationships

A variety of methods for determining relationships (e.g., identity, similarity and/or homology) between two or more sequences, such as SEQ ID NO:1 and SEQ ID NO:13, are available and well known in the art. The methods include manual alignment, computer assisted sequence alignment, and combinations thereof. A number of algorithms (which are generally computer implemented) for performing sequence alignment are widely available, or can be produced by one of skill. These methods include, e.g., the local homology algorithm of Smith and Waterman (1981) *Adv. Appl. Math.* 2:482; the homology alignment algorithm of Needleman and Wunsch (1970) *J. Mol. Biol.* 48:443; the search for similarity method of Pearson and Lipman (1988) *Proc. Natl. Acad. Sci.* (*USA*) 85:2444; and/or by computerized implementations of these algorithms (e.g., GAP, BESTFIT, FASTA, and TFASTA in the Wisconsin Genetics Software Package Release 7.0, Genetics Computer Group, 575 Science Dr., Madison, Wis.).

For example, software for performing sequence identity (and sequence similarity) analysis using the BLAST algorithm is described in Altschul et al. (1990) *J. Mol. Biol.* 215:403-410. This software is publicly available, e.g., through the National Center for Biotechnology Information on the world wide web at ncbi.nlm.nih.gov. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP (BLAST Protein) program uses as defaults a wordlength (W) of 3, an expectation (E) of 10, and the BLOSUM62 scoring matrix (see, Henikoff and Henikoff (1989) *Proc. Natl. Acad. Sci. USA* 89:10915).

Additionally, the BLAST algorithm performs a statistical analysis of the similarity between two sequences (see, e.g., Karlin and Altschul (1993) *Proc. Nat'l. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence (and, therefore, in this context, homologous) if the smallest sum probability in a comparison of the test nucleic acid to the reference nucleic acid is less than about 0.1, or less than about 0.01, and or even less than about 0.001.

Another example of a useful sequence alignment algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng and Doolittle (1987) *J. Mol. Evol.* 35:351-360. The method used is similar to the method described by Higgins and Sharp (1989) *CABIOS* 5:151-153. The program can align, e.g., up to 300 sequences of a maximum length of 5,000 letters. The multiple alignment procedure begins with the pairwise alignment of the two most similar sequences, producing a cluster of two aligned sequences. This cluster can then be aligned to the next most related sequence or cluster of aligned sequences. Two clusters of sequences can be aligned by a simple extension of the pairwise alignment of two individual sequences. The final alignment is achieved by a series of progressive, pairwise alignments. The program can also be used to plot a dendogram or tree representation of clustering relationships. The program is run by designating specific sequences and their amino acid or nucleotide coordinates for regions of sequence comparison.

An additional example of an algorithm that is suitable for multiple DNA, or amino acid, sequence alignments is the CLUSTALW program (Thompson, J. D. et al. (1994) *Nucl. Acids. Res.* 22: 4673-4680). CLUSTALW performs multiple pairwise comparisons between groups of sequences and assembles them into a multiple alignment based on homology. Gap open and Gap extension penalties can be, e.g., 10 and 0.05 respectively. For amino acid alignments, the BLOSUM algorithm can be used as a protein weight matrix. See, e.g., Henikoff and Henikoff (1992) *Proc. Natl. Acad. Sci. USA* 89: 10915-10919.

Nucleic Acid Hybridization

Similarity between nucleic acids can also be evaluated by "hybridization" between single stranded (or single stranded regions of) nucleic acids with complementary or partially complementary polynucleotide sequences. Hybridization is a measure of the physical association between nucleic acids, typically, in solution, or with one of the nucleic acid strands immobilized on a solid support, e.g., a membrane, a bead, a chip, a filter, etc. Nucleic acid hybridization occurs based on a variety of well characterized physico-chemical forces, such as hydrogen bonding, solvent exclusion, base stacking and the like. Numerous protocols for nucleic acid hybridization are well known in the art. An extensive guide to the hybridization of nucleic acids is found in Tijssen (1993) *Laboratory Techniques in Biochemistry and Molecular Biology—Hybridization with Nucleic Acid Probes*, part I, chapter 2, "Overview of principles of hybridization and the strategy of nucleic acid probe assays," (Elsevier, N.Y.), as well as in Ausubel et al. *Current Protocols in Molecular Biology* (supplemented through 2003) John Wiley & Sons, New York ("Ausubel"); Sambrook et al. *Molecular Cloning—A Laboratory Manual* (3rd Ed.), Vol. 1-3, Cold Spring Harbor Laboratory, Cold Spring Harbor, N.Y., 2001 ("Sambrook"), and Berger and Kimmel *Guide to Molecular Cloning Techniques, Methods in Enzymology* volume 152 Academic Press, Inc., San Diego, Calif. ("Berger"). Hames and Higgins (1995) *Gene Probes* 1, IRL Press at Oxford University Press, Oxford, England (Hames and Higgins 1) and Hames and Higgins (1995) *Gene Probes* 2, IRL Press at Oxford University Press, Oxford, England (Hames and Higgins 2) provide details on the synthesis, labeling, detection and quantification of DNA and RNA, including oligonucleotides.

Conditions suitable for obtaining hybridization, including differential hybridization, are selected according to the theoretical melting temperature ($T_m$) between complementary and partially complementary nucleic acids. Under a given set of conditions, e.g., solvent composition, ionic strength, etc., the $T_m$ is the temperature at which the duplex between the hybridizing nucleic acid strands is 50% denatured. That is, the $T_m$ corresponds to the temperature corresponding to the midpoint in transition from helix to random coil; it depends on length, nucleotide composition, and ionic strength for long, stretches of nucleotides.

After hybridization, unhybridized nucleic acids can be removed by a series of washes, the stringency of which can be adjusted depending upon the desired results. Low stringency washing conditions (e.g., using higher salt and lower temperature) increase sensitivity, but can produce nonspecific hybridization signals and high background signals. Higher stringency conditions (e.g., using lower salt and higher temperature that is closer to the $T_m$) lower the background signal, typically with primarily the specific signal remaining. See, also, Rapley, R. and Walker, J. M. eds., *Molecular Biomethods Handbook* (Humana Press, Inc. 1998).

"Stringent hybridization wash conditions" or "stringent conditions" in the context of nucleic acid hybridization experiments, such as Southern and northern hybridizations, are sequence dependent, and are different under different environmental parameters. An extensive guide to the hybridization of nucleic acids is found in Tijssen (1993), supra, and in Hames and Higgins 1 and Hames and Higgins 2, supra.

An example of stringent hybridization conditions for hybridization of complementary nucleic acids which have more than 100 complementary residues on a filter in a Southern or northern blot is 2×SSC, 50% formamide at 42° C., with the hybridization being carried out overnight (e.g., for approximately 20 hours). An example of stringent wash conditions is a 0.2×SSC wash at 65° C. for 15 minutes (see Sambrook, supra for a description of SSC buffer). Often, the wash determining the stringency is preceded by a low stringency wash to remove signal due to residual unhybridized probe. An example low stringency wash is 2×SSC at room temperature (e.g., 20° C. for 15 minutes).

In general, a signal to noise ratio of at least 2× (or higher, e.g., at least 5×, 10×, 20×, 50×, 100×, or more) than that observed for an unrelated probe in the particular hybridization assay indicates detection of a specific hybridization. Detection of at least stringent hybridization between two sequences in the context of the present invention indicates relatively strong structural similarity to, e.g., the nucleic acids of the present invention provided in the sequence listings herein.

For purposes of the present invention, generally, "highly stringent" hybridization and wash conditions are selected to be about 5° C. or less lower than the thermal melting point ($T_m$) for the specific sequence at a defined ionic strength and pH (as noted below, highly stringent conditions can also be referred to in comparative terms). Target sequences that are closely related or identical to the nucleotide sequence of interest (e.g., "probe") can be identified under stringent or highly stringent conditions. Lower stringency conditions are appropriate for sequences that are less complementary.

For example, in determining stringent or highly stringent hybridization (or even more stringent hybridization) and wash conditions, the hybridization and wash conditions are gradually increased (e.g., by increasing temperature, decreasing salt concentration, increasing detergent concentration and/or increasing the concentration of organic solvents, such as formamide, in the hybridization or wash), until a selected set of criteria are met. For example, the hybridization and wash conditions are gradually increased until a probe comprising one or more polynucleotide sequences of the invention, e.g., sequences or unique subsequences selected from SEQ ID NO:1 and/or complementary polynucleotide sequences, binds to a perfectly matched complementary target (again, a nucleic acid comprising one or more nucleic acid sequences or subsequences selected from SEQ ID NO:1 and/or complementary polynucleotide sequences thereof), with a signal to noise ratio that is at least 2× (and optionally 5×, 10×, or 100× or more) as high as that observed for hybridization of the probe to an unmatched target (e.g., a polynucleotide sequence comprising the corresponding one or more sequences or subsequences selected from SEQ ID NO:13 and/or complementary polynucleotide sequences thereof), as desired. Preferably, the sequences or subsequences are selected from a portion of SEQ ID NO:1 that includes at least a subsequence that is not included in SEQ ID NOs:14-19

Using the polynucleotides of the invention, or subsequences thereof, novel target nucleic acids can be obtained; such target nucleic acids are also a feature of the invention. For example, such target nucleic acids include sequences that hybridize under stringent conditions to a unique oligonucleotide probe corresponding to any of the polynucleotides of the invention, e.g., SEQ ID NO:1.

Higher ratios of signal to noise can be achieved by increasing the stringency of the hybridization conditions such that ratios of about 15×, 20×, 30×, 50× or more are obtained. The particular signal will depend on the label used in the relevant assay, e.g., a fluorescent label, a colorimetric label, a radioactive label, or the like.

Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

Defining Proteins by Immunoreactivity

Because the polypeptides of the invention provide a variety of new polypeptide sequences, the polypeptides also provide new structural features which can be recognized, e.g., in immunological assays. The generation of antibodies or antisera which specifically bind the polypeptides of the invention, as well as the polypeptides which are bound by such antibodies or antisera, and the antibodies or antisera themselves, are a feature of the invention.

Thus, the proteins of the invention can also be identified by immunoreactivity; e.g., a polypeptide of the invention can include an amino acid sequence or subsequence that is specifically bound by an antibody that specifically binds to an amino acid sequence or subsequence encoded by SEQ ID NO:1, wherein the antibody does not specifically bind to an amino acid sequence or subsequence encoded by SEQ ID NO:13 or SEQ ID NO:14 (or, optionally, to an amino acid sequence or subsequence encoded by the genome of another naturally occurring respiratory syncytial virus).

Methods of producing antibodies, performing immunoassays, and the like are well known in the art. See e.g., the section entitled "Antibodies" below and references therein.

In one typical format, an immunoassay to identify a polypeptide of the invention uses a polyclonal antiserum which was raised against one or more of the RSV 9320 polypeptides of the invention (e.g., a polypeptide comprising SEQ ID NOs:2-11 or SEQ ID NO:12 with a deletion of residues 164-197), or a substantial subsequence thereof (i.e., at least about 30%, 40%, 50%, 60%, 70%, 80%, 90%, 95%, or 98% or more of the full length sequence provided). The full set of potential polypeptide immunogens derived from one or more of the RSV 9320 polypeptides of the invention are collectively referred to below as "the immunogenic polypeptides." The resulting antisera is optionally selected to have low cross-reactivity against the control RSV B1 polypeptides and/or other known, e.g., naturally occurring, RSV polypeptides, and any such cross-reactivity is removed by immunoabsorption with one or more of the control RSV polypeptides, prior to use of the polyclonal antiserum in the immunoassay.

In order to produce antisera for use in an immunoassay, one or more of the immunogenic polypeptides is produced and purified as described herein. For example, recombinant protein can be produced in a mammalian cell line. An inbred strain of mice (used in this assay because results are more reproducible due to the virtual genetic identity of the mice) is immunized with the immunogenic polypeptide(s) in combination with a standard adjuvant, such as Freund's adjuvant, and a standard mouse immunization protocol (see Harlow and Lane (1988) *Antibodies, A Laboratory Manual* Cold Spring Harbor Press, New York, for a standard description of antibody generation, immunoassay formats and conditions that can be used to determine specific immunoreactivity). Alternatively, one or more synthetic or recombinant polypeptides derived from the sequences disclosed herein is conjugated to a carrier protein and used as an immunogen.

Polyclonal sera are collected and titered against the immunogenic polypeptide(s) in an immunoassay, for example, a solid phase immunoassay with one or more of the immunogenic polypeptides immobilized on a solid support. Polyclonal antisera with a titer of $10^6$ or greater are selected, pooled and subtracted with the control RSV polypeptides to produce subtracted pooled titered polyclonal antisera.

The subtracted pooled titered polyclonal antisera are tested for cross reactivity against the control RSV polypeptides. Preferably at least two of the immunogenic RSV 9320 polypeptides are used in this determination, preferably in conjunction with at least two of the control RSV polypeptides, to identify antibodies which are specifically bound by the immunogenic polypeptides(s).

In this comparative assay, discriminatory binding conditions are determined for the subtracted titered polyclonal antisera which result in at least about a 5-10 fold higher signal to noise ratio for binding of the titered polyclonal antisera to the immunogenic RSV 9320 polypeptides as compared to binding to the control RSV polypeptides. That is, the stringency of the binding reaction is adjusted by the addition of non-specific competitors, such as albumin or non-fat dry milk, or by adjusting salt conditions, temperature, or the like. These binding conditions are used in subsequent assays for determining whether a test polypeptide is specifically bound by the pooled subtracted polyclonal antisera. In particular, a test polypeptide which shows at least a 2-5× higher signal to noise ratio than the control polypeptides under discriminatory binding conditions, and at least about a 1/2 signal to noise ratio as compared to the immunogenic polypeptide(s), shares substantial structural similarity or homology with the immunogenic polypeptide(s) as compared to the control RSV polypeptides, and is, therefore, a polypeptide of the invention.

In another example, immunoassays in the competitive binding format are used for detection of a test polypeptide. For example, as noted, cross-reacting antibodies are removed from the pooled antisera mixture by immunoabsorption with the control RSV polypeptides. The immunogenic polypeptide(s) are then immobilized to a solid support which is exposed to the subtracted pooled antisera. Test proteins are added to the assay to compete for binding to the pooled subtracted antisera. The ability of the test protein(s) to compete for binding to the pooled subtracted antisera as compared to the immobilized protein(s) is compared to the ability of the immunogenic polypeptide(s) added to the assay to compete for binding (the immunogenic polypeptides compete effectively with the immobilized immunogenic polypeptides for binding to the pooled antisera). The percent cross-reactivity for the test proteins is calculated, using standard calculations.

In a parallel assay, the ability of the control proteins to compete for binding to the pooled subtracted antisera is determined as compared to the ability of the immunogenic polypeptide(s) to compete for binding to the antisera. Again, the percent cross-reactivity for the control polypeptides is calculated, using standard calculations. Where the percent cross-reactivity is at least 5-10× as high for the test polypeptides, the test polypeptides are said to specifically bind the pooled subtracted antisera, and are, therefore, polypeptides of the invention.

In general, the immunoabsorbed and pooled antisera can be used in a competitive binding immunoassay as described herein to compare any test polypeptide to the immunogenic polypeptide(s). In order to make this comparison, the two polypeptides are each assayed at a wide range of concentrations and the amount of each polypeptide required to inhibit 50% of the binding of the subtracted antisera to the immobilized protein is determined using standard techniques. If the amount of the test polypeptide required is less than twice the amount of the immunogenic polypeptide that is required, then the test polypeptide is said to specifically bind to an antibody generated to the immunogenic polypeptide, provided the amount is at least about 5-10× as high as for a control polypeptide.

As a final determination of specificity, the pooled antisera is optionally fully immunosorbed with the immunogenic polypeptide(s) (rather than the control polypeptides) until little or no binding of the resulting immunogenic polypeptide subtracted pooled antisera to the immunogenic polypeptide(s) used in the immunoabsorption is detectable. This fully immunosorbed antisera is then tested for reactivity with the test polypeptide. If little or no reactivity is observed (i.e., no more than 2× the signal to noise ratio observed for binding of the fully immunosorbed antisera to the immunogenic polypeptide), then the test polypeptide is specifically bound by the antisera elicited by the immunogenic protein.

Sequence Variations

Silent Variations

Due to the degeneracy of the genetic code, any of a variety of nucleic acid sequences encoding polypeptides and/or viruses of the invention are optionally produced, some which can bear lower levels of sequence identity to the RSV nucleic acid and polypeptide sequences in the figures. The following provides a typical codon table specifying the genetic code, found in many biology and biochemistry texts.

TABLE 1

Codon Table

| Amino acids | | | Codon | | | |
|---|---|---|---|---|---|---|
| Alanine | Ala | A | GCA | GCC | GCG | GCU |
| Cysteine | Cys | C | UGC | UGU | | |
| Aspartic acid | Asp | D | GAC | GAU | | |
| Glutamic acid | Glu | E | GAA | GAG | | |

TABLE 1-continued

| Codon Table | | | | | | | | |
|---|---|---|---|---|---|---|---|---|
| Amino acids | | | Codon | | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

The codon table shows that many amino acids are encoded by more than one codon. For example, the codons AGA, AGG, CGA, CGC, CGG, and CGU all encode the amino acid arginine. Thus, at every position in the nucleic acids of the invention where an arginine is specified by a codon, the codon can be altered to any of the corresponding codons described above without altering the encoded polypeptide. It is understood that U in an RNA sequence corresponds to T in a DNA sequence.

As an example, a nucleic acid sequence corresponding to the amino acid sequence FEV (residues 164-166 of SEQ ID NO:12) is TTTGAAGTG. A silent variation of this sequence includes TTCGAGGTA (also encoding FEV).

Such "silent variations" are one species of "conservatively modified variations", discussed below. One of skill will recognize that each codon in a nucleic acid (except ATG, which is ordinarily the only codon for methionine, and TTG, which is ordinarily the only codon for tryptophan) can be modified by standard techniques to encode a functionally identical polypeptide. Accordingly, each silent variation of a nucleic acid which encodes a polypeptide is implicit in any described sequence. The invention, therefore, explicitly provides each and every possible variation of a nucleic acid sequence encoding a polypeptide of the invention that could be made by selecting combinations based on possible codon choices. These combinations are made in accordance with the standard triplet genetic code (e.g., as set forth in Table 1, or as is commonly available in the art) as applied to the nucleic acid sequence encoding an RSV polypeptide of the invention. All such variations of every nucleic acid herein are specifically provided and described by consideration of the sequence in combination with the genetic code. One of skill is fully able to make these silent substitutions using the methods herein.

Conservative Variations

"Conservatively modified variations" or, simply, "conservative variations" of a particular nucleic acid sequence or polypeptide are those which encode identical or essentially indentical amino acid sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid.

Conservative substitution tables providing functionally similar amino acids are well known in the art. Table 2 sets forth six groups which contain amino acids that are "conservative substitutions" for one another. Alternative conservative substitution charts are available in the art and can be used in a similar manner.

TABLE 2

| Conservative Substitution Groups | | | | |
|---|---|---|---|---|
| 1 | Alanine (A) | Serine (S) | Threonine (T) | |
| 2 | Aspartic acid (D) | Glutamic acid (E) | | |
| 3 | Asparagine (N) | Glutamine (Q) | | |
| 4 | Arginine (R) | Lysine (K) | | |
| 5 | Isoleucine (I) | Leucine (L) | Methionine (M) | Valine (V) |
| 6 | Phenylalanine (F) | Tyrosine (Y) | Tryptophan (W) | |

Thus, "conservatively substituted variations" of a polypeptide sequence of the present invention include substitutions of a small percentage, typically less than 5%, more typically less than 2% or 1%, of the amino acids of the polypeptide sequence, with a conservatively selected amino acid of the same conservative substitution group.

For example, a conservatively substituted variation of the RSV strain B9320 M2-1 polypeptide in SEQ ID NO:9 will contain "conservative substitutions", e.g., according to the six groups defined above, in up to about 10 residues (i.e., about 5% of the amino acids) in the full-length polypeptide.

In a further example, if conservative substitutions were localized in the region corresponding to amino acids 10-12 of RSV 9320 M2-1 (EIR), examples of conservatively substituted variations of this region include conservative substitutions of DLK or DMR (or any others that can be made according to Table 2) for EIR.

Listing of a protein sequence herein, in conjunction with the above substitution table, provides an express listing of all conservatively substituted proteins.

Finally, the addition or deletion of sequences which do not alter the encoded activity of a nucleic acid molecule, such as the addition or deletion of a non-functional sequence, an epitope tag, a polyhistidine tag, GFP, or the like, is a conservative variation of the basic nucleic acid or polypeptide.

One of skill will appreciate that many conservative variations of the nucleic acid constructs which are disclosed yield a functionally identical construct. For example, as discussed above, owing to the degeneracy of the genetic code, "silent substitutions" (i.e., substitutions in a nucleic acid sequence which do not result in an alteration in an encoded polypeptide) are an implied feature of every nucleic acid sequence which encodes an amino acid. Similarly, "conservative amino acid substitutions," in which one or a few amino acids in an amino acid sequence are substituted with different amino acids with highly similar properties, are also readily identified as being highly similar to a disclosed construct. Such conservative variations of each disclosed or claimed virus, nucleic acid or protein are a feature of the present invention. Such conservative (e.g., silent) variations can be used, e.g., to produce antibodies for detection of or immunoprotection against RSV.

Production of Viral Nucleic Acids

In the context of the invention, viral (e.g., RSV) nucleic acids and/or proteins are manipulated according to well known molecular biology techniques. Detailed protocols for numerous such procedures, including amplification, cloning, mutagenesis, transformation, and the like, are described in, e.g., in Ausubel et al. *Current Protocols in Molecular Biology* (supplemented through 2003) John Wiley & Sons, New York ("Ausubel"); Sambrook et al. *Molecular Cloning—A Laboratory Manual* (3rd Ed.), Vol. 1-3, Cold Spring Harbor Laboratory, Cold Spring Harbor, N.Y., 2001 ("Sambrook"), and Berger and Kimmel *Guide to Molecular Cloning Techniques, Methods in Enzymology* volume 152 Academic Press, Inc., San Diego, Calif. ("Berger").

In addition to the above references, protocols for in vitro amplification techniques, such as the polymerase chain reaction (PCR), the ligase chain reaction (LCR), Qβ-replicase amplification, and other RNA polymerase mediated techniques (e.g., NASBA), useful e.g., for amplifying cDNA polynucleotides of the invention, are found in Mullis et al. (1987) U.S. Pat. No. 4,683,202*; PCR Protocols A Guide to Methods and Applications* (Innis et al. eds) Academic Press Inc. San Diego, Calif. (1990) ("Innis"); Arnheim and Levinson (1990) *C&EN* 36*; The Journal Of NIH Research* (1991) 3:81; Kwoh et al. (1989) *Proc Natl Acad Sci USA* 86, 1173; Guatelli et al. (1990) *Proc Natl Acad Sci USA* 87:1874; Lomell et al. (1989) *J Clin Chem* 35:1826; Landegren et al. (1988) *Science* 241:1077; Van Brunt (1990) *Biotechnology* 8:291; Wu and Wallace (1989) *Gene* 4: 560; Barringer et al. (1990) *Gene* 89:117, and Sooknanan and Malek (1995) *Biotechnology* 13:563. Additional methods, useful for cloning nucleic acids in the context of the present invention, include Wallace et al. U.S. Pat. No. 5,426,039. Improved methods of amplifying large nucleic acids by PCR are summarized in Cheng et al. (1994) *Nature* 369:684 and the references therein.

Certain polynucleotides of the invention, e.g., oligonucleotides, can be synthesized utilizing various solid-phase strategies including mononucleotide- and/or trinucleotide-based phosphoramidite coupling chemistry. For example, nucleic acid sequences can be synthesized by the sequential addition of activated monomers and/or trimers to an elongating polynucleotide chain. See e.g., Caruthers, M. H. et al. (1992) *Meth Enzymol* 211:3.

In lieu of synthesizing the desired sequences, essentially any nucleic acid can be custom ordered from any of a variety of commercial sources, such as The Midland Certified Reagent Company (www.mcrc.com), The Great American Gene Company (www.genco.com), ExpressGen, Inc. (www.expressgen.com), QIAGEN (http://oligos.qiagen.com), and many others.

In addition, substitutions of selected amino acid residues in viral polypeptides can be accomplished by, e.g., site directed mutagenesis. For example, viral polypeptides with amino acid substitutions functionally correlated with desirable phenotypic characteristic, e.g., an attenuated phenotype, cold adaptation and/or temperature sensitivity, can be produced by introducing specific mutations into a viral nucleic acid segment (e.g., a cDNA) encoding the polypeptide. Methods for site directed mutagenesis are well known in the art, and are described, e.g., in Ausubel, Sambrook, and Berger, supra. Numerous kits for performing site directed mutagenesis are commercially available, e.g., the ExSite™ and Chameleon™ site directed mutagenesis kits (Stratagene, La Jolla), and can be used according to the manufacturer's instructions to introduce, e.g., one or more nucleotide substitutions specifying one or more amino acid substitutions into an RSV polynucleotide.

Various types of mutagenesis are optionally used in the present invention, e.g., to modify nucleic acids and encoded polypeptides and/or viruses to produce conservative or non-conservative variants. Any available mutagenesis procedure can be used. Such mutagenesis procedures optionally include selection of mutant nucleic acids and polypeptides for one or more activity of interest. Procedures that can be used include, but are not limited to: site-directed point mutagenesis, random point mutagenesis, in vitro or in vivo homologous recombination (DNA shuffling), mutagenesis using uracil containing templates, oligonucleotide-directed mutagenesis, phosphorothioate-modified DNA mutagenesis, mutagenesis using gapped duplex DNA, point mismatch repair, mutagenesis using repair-deficient host strains, restriction-selection and restriction-purification, deletion mutagenesis, mutagenesis by total gene synthesis, double-strand break repair, and many others known to persons of skill. In one embodiment, mutagenesis can be guided by information known about the naturally occurring molecule or altered or mutated naturally occurring molecules, e.g., sequence, sequence comparisons, physical properties, crystal structure or the like. In another class of embodiments, modification is essentially random (e.g., as in classical DNA shuffling).

Several of these procedures are set forth in Sambrook and Ausubel, herein. Additional information on these procedures is found in the following publications and the references cited therein: Arnold (1993) "Protein engineering for unusual environments" *Current Opinion in Biotechnology* 4:450-455; Bass et al. (1988) "Mutant Trp repressors with new DNA-binding specificities" *Science* 242:240-245; Botstein and Shortle (1985) "Strategies and applications of in vitro mutagenesis" *Science* 229:1193-1201; Carter et al. (1985) "Improved oligonucleotide site-directed mutagenesis using M13 vectors" *Nucl. Acids Res.* 13: 4431-4443; Carter (1986) "Site-directed mutagenesis" *Biochem. J.* 237:1-7; Carter (1987) "Improved oligonucleotide-directed mutagenesis using M13 vectors" *Methods in Enzymol.* 154: 382-403; Dale et al. (1996) "Oligonucleotide-directed random mutagenesis using the phosphorothioate method" *Methods Mol. Biol.* 57:369-374; Eghtedarzadeh and Henikoff (1986) "Use of oligonucleotides to generate large deletions" *Nucl. Acids Res.* 14: 5115; Fritz et al. (1988) "Oligonucleotide-directed construction of mutations: a gapped duplex DNA procedure without enzymatic reactions in vitro" *Nucl. Acids Res.* 16: 6987-6999; Grundstrom et al. (1985) "Oligonucleotide-directed mutagenesis by microscale 'shot-gun' gene synthesis" *Nucl. Acids Res.* 13: 3305-3316; Kunkel (1987) "The efficiency of oligonucleotide directed mutagenesis" in *Nucleic Acids and Molecular Biology* (Eckstein, F. and Lilley, D. M. J. eds., Springer Verlag, Berlin)); Kunkel (1985) "Rapid and efficient site-specific mutagenesis without phenotypic selection" *Proc. Natl. Acad. Sci. USA* 82:488-492; Kunkel et al. (1987) "Rapid and efficient site-specific mutagenesis without phenotypic selection" *Methods in Enzymol.* 154, 367-382; Kramer et al. (1984) "The gapped duplex DNA approach to oligonucleotide-directed mutation construction" *Nucl. Acids Res.* 12: 9441-9456; Kramer and Fritz (1987) "Oligonucleotide-directed construction of mutations via gapped duplex DNA" *Methods in Enzymol.* 154:350-367; Kramer et al. (1984) "Point Mismatch Repair" *Cell* 38:879-887; Kramer et al. (1988) "Improved enzymatic in vitro reactions in the gapped duplex DNA approach to oligonucleotide-directed construction of mutations" *Nucl. Acids Res*. 16: 7207; Ling et al. (1997) "Approaches to DNA mutagenesis: an overview" *Anal Biochem*. 254(2): 157-178; Lorimer and Pastan (1995) *Nucleic Acids Res*. 23, 3067-8; Mandecki (1986) "Oligonucleotide-directed double-strand break repair in plasmids of *Escherichia coli*: a method for site-specific mutagenesis" *Proc. Natl. Acad. Sci. USA* 83:7177-7181; Nakamaye and Eckstein (1986) "Inhibition of restriction endonuclease Nci I cleavage by phosphorothioate groups and its application to oligonucleotide-directed mutagenesis" *Nucl. Acids Res*. 14: 9679-9698; Nambiar et al. (1984) "Total synthesis and cloning of a gene coding for the ribonuclease S protein" *Science* 223: 1299-1301; Sakamar and Khorana (1988) "Total synthesis and expression of a gene for the a-subunit of bovine rod outer segment guanine nucleotide-binding protein (transducin)" *Nucl. Acids Res*. 14: 6361-6372; Sayers et al. (1988) "Y-T Exonucleases in phosphorothioate-based oligonucleotide-directed mutagenesis" *Nucl. Acids Res*. 16:791-802; Sayers et al. (1988) "Strand specific cleavage of phosphorothioate-containing DNA by reaction with restriction endonucleases in the presence of ethidium bromide" *Nucl. Acids Res*. 16: 803-814; Sieber et al.(2001) *Nature Biotechnology* 19:456-460; Smith (1985) "In vitro mutagenesis" *Ann. Rev. Genet*. 19:423-462; Methods in Enzymol. 100: 468-500 (1983); *Methods in Enzymol*. 154: 329-350 (1987); Stemmer (1994) *Nature* 370, 389-91; Taylor et al. (1985) "The use of phosphorothioate-modified DNA in restriction enzyme reactions to prepare nicked DNA" *Nucl. Acids Res*. 13: 8749-8764; Taylor et al. (1985) "The rapid generation of oligonucleotide-directed mutations at high frequency using phosphorothioate-modified DNA" *Nucl. Acids Res*. 13: 8765-8787; Wells et al. (1986) "Importance of hydrogen-bond formation in stabilizing the transition state of subtilisin" *Phil. Trans. R. Soc. Lond. A* 317: 415-423; Wells et al. (1985) "Cassette mutagenesis: an efficient method for generation of multiple mutations at defined sites" *Gene* 34:315-323; Zoller and Smith (1982) "Oligonucleotide-directed mutagenesis using M13-derived vectors: an efficient and general procedure for the production of point mutations in any DNA fragment" *Nucleic Acids Res*. 10:6487-6500; Zoller and Smith (1983) "Oligonucleotide-directed mutagenesis of DNA fragments cloned into M13 vectors" *Methods in Enzymol*. 100: 468-500; and Zoller and Smith (1987) "Oligonucleotide-directed mutagenesis: a simple method using two oligonucleotide primers and a single-stranded DNA template" *Methods in Enzymol*. 154:329-350. Additional details on many of the above methods can be found in *Methods in Enzymology* Volume 154, which also describes useful controls for trouble-shooting problems with various mutagenesis methods.

Vectors, Promoters and Expression Systems

The present invention includes recombinant constructs incorporating one or more of the nucleic acid sequences described above. Such constructs include a vector, for example, a plasmid, a cosmid, a phage, a virus, a bacterial artificial chromosome (BAC), a yeast artificial chromosome (YAC), etc., into which one or more of the polynucleotide sequences of the invention, for example, SEQ ID NO:1 or subsequences thereof, e.g., including at least one ORF selected from SEQ ID NO:1, has been inserted, in a forward or reverse orientation. For example, the inserted nucleic acid can include all or part of at least one of the polynucleotide sequences of the invention. Typically the vector is selected based on the characteristics, e.g., size of the selected polynucleotide sequence, and on the intended use, e.g., expression, amplification, etc. In a preferred embodiment, the construct further comprises regulatory sequences, including, for example, a promoter, operably linked to the sequence. Large numbers of suitable vectors and promoters are known to those of skill in the art and are commercially available.

The polynucleotides of the present invention can be included in any one of a variety of vectors suitable for generating sense or antisense RNA, and optionally, polypeptide (or peptide) expression products, e.g., selected from SEQ ID NOs:2-11. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated virus, retroviruses, and many others, as well as viral amplicon vectors. Any vector that is capable of introducing genetic material into a cell, and, if replication is desired, which is replicable in the relevant host, can be used.

In an expression vector, the polynucleotide sequence, commonly a subsequence of SEQ ID NO:1, e.g., comprising an ORF, such as an ORF encoding a polypeptide (or peptide) selected from among SEQ ID NOs: 2-11 (or variants thereof, e.g., conservative variations thereof), is physically arranged in proximity and orientation to an appropriate transcription control sequence (promoter, and optionally, one or more enhancers) to direct mRNA synthesis. For example, a subsequence of SEQ ID NO:1, e.g., encoding a polypeptide selected from a subsequence of one of SEQ ID NOs:2-11, can be inserted into an expression vector to produce antigenic peptide for the production of antibodies, e.g., for diagnostic or therapeutic purposes. That is, the polynucleotide sequence of interest is operably linked to an appropriate transcription control sequence. Examples of such promoters include: LTR or SV40 promoter, *E. coli* lac or trp promoter, phage lambda $P_L$ promoter, and other promoters known to control expression of genes in prokaryotic or eukaryotic cells or their viruses. The expression vector typically also contains a ribosome binding site for translation initiation, and a transcription terminator. The vector optionally includes appropriate sequences for amplifying expression. In addition, the expression vectors optionally comprise one or more selectable marker genes to provide a phenotypic trait for selection of transformed host cells, such as dihydrofolate reductase or neomycin resistance for eukaryotic cell culture, or such as tetracycline or ampicillin resistance in *E. coli*.

Where translation of polypeptide encoded by a nucleic acid comprising a polynucleotide sequence of the invention is desired, additional translation specific initiation signals can improve the efficiency of translation. These signals can include, e.g., an ATG initiation codon and adjacent sequences. In some cases, for example, full-length cDNA molecules or chromosomal segments including a coding sequence incorporating, e.g., a polynucleotide sequence of the invention, a translation initiation codon and associated sequence elements are inserted into the appropriate expression vector simultaneously with the polynucleotide sequence of interest. In such cases, additional translational control signals are not required. However, in cases where only a polypeptide coding sequence, e.g., encoding an amino acid sequence selected from among SEQ ID NOs:2-11 or a portion thereof, is inserted, exogenous translational control signals, including an ATG initiation codon is provided for expression of the relevant sequence. The initiation codon is put in the correct reading frame to ensure transcription of the polynucleotide sequence of interest. Exogenous transcriptional elements and initiation codons can be of various origins, both natural and synthetic. The efficiency of expression can be enhanced by the inclusion of enhancers appropriate to the cell system in use (Scharf D et al. (1994) *Results Probl Cell Differ* 20:125-62; Bittner et al. (1987) *Methods in Enzymol* 153:516-544).

Polypeptide Production and Recovery

The present invention also relates to the introduction of vectors incorporating the polynucleotides of the invention (e.g., polynucleotides including all or part of one or more ORFs selected from SEQ ID NO:1) into host cells and the production of polypeptides of the invention, e.g., one or more polypeptide selected from SEQ ID NOs:2-11 or subsequences thereof (e.g., unique subsequences thereof) by recombinant techniques. Recombinant and/or isolated polypeptides encoded by the polynucleotides of the invention, e.g., SEQ ID NOs:2-11, or subsequences (e.g., unique subsequences) thereof are used, for example, as antigens to produce antibodies in animal or human subjects. For example, antigenic polypeptides (or peptides) corresponding to all or part of a polypeptide represented by SEQ ID NOs: 2-11 can be injected into an experimental animal to produce antibodies specific for one or more strains of RSV, as further described in the section entitled “Antibodies” below. Additionally, the antigenic polypeptides can be administered, e.g., as a vaccine, to human subjects to elicit an immune response specific for one or more strains of RSV. For example, such an elicited immune response can be a protective immune response.

To produce the polypeptides of the invention, host cells are genetically engineered (e.g., transduced, transformed or transfected) with a vector, such as an expression vector, of this invention. As described above, the vector can be in the form of a plasmid, a viral particle, a phage, etc. Examples of appropriate expression hosts include: bacterial cells, such as *E. coli, Streptomyces*, and *Salmonella typhimurium*; fungal cells, such as *Saccharomyces cerevisiae, Pichia pastoris*, and *Neurospora crassa*; insect cells such as *Drosophila* and *Spodoptera frugiperda*; mammalian cells such as 3T3, COS, CHO, BHK, HEK 293 or Bowes melanoma; plant cells, etc.

The engineered host cells can be cultured in conventional nutrient media modified as appropriate for activating promoters, selecting transformants, or amplifying the inserted polynucleotide sequences. The culture conditions, such as temperature, pH and the like, are typically those previously used with the host cell selected for expression, and will be apparent to those skilled in the art and in the references cited herein, including, e.g., Freshney (1994) *Culture of Animal Cells, a Manual of Basic Technique*, third edition, Wiley-Liss, New York and the references cited therein. In addition to Sambrook, Berger and Ausubel, details regarding cell culture can be found in Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg N.Y.) and Atlas and Parks (eds) *The Handbook of Microbiological Media* (1993) CRC Press, Boca Raton, Fla.

In bacterial systems, a number of expression vectors can be selected depending upon the use intended for the expressed product. For example, when large quantities of a polypeptide or fragments thereof are needed for the production of antibodies, vectors which direct high level expression of fusion proteins that are readily purified are favorably employed. Such vectors include, but are not limited to, multifunctional *E. coli* cloning and expression vectors such as BLUESCRIPT (Stratagene), in which the coding sequence of interest, e.g., a polynucleotide of the invention as described above, can be ligated into the vector in-frame with sequences for the amino-terminal translation initiating Methionine and the subsequent 7 residues of beta-galactosidase producing a catalytically active beta galactosidase fusion protein; pIN vectors (Van Heeke and Schuster (1989) *J Biol Chem* 264:5503-5509); pET vectors (Novagen, Madison Wis.); and the like.

Similarly, in the yeast *Saccharomyces cerevisiae* a number of vectors containing constitutive or inducible promoters such as alpha factor, alcohol oxidase and PGH can be used for production of the desired expression products. For reviews, see Berger, Ausubel, and, e.g., Grant et al. (1987) *Methods in Enzymology* 153:516-544.

Vectors suitable for replication in mammalian cells are also known in the art. Exemplary vectors include those derived from SV40, retroviruses, bovine papilloma virus, vaccinia virus, other herpesviruses and adenovirus. Such suitable mammalian expression vectors optionally contain a promoter to mediate transcription of foreign DNA sequences and, optionally, an enhancer. Suitable promoters are known in the art and include viral promoters such as those from SV40, cytomegalovirus (CMV), Rous sarcoma virus (RSV), adenovirus (ADV), and bovine papilloma virus (BPV).

The optional presence of an enhancer, combined with the promoter described above, will typically increase expression levels. An enhancer is any regulatory DNA sequence that can stimulate transcription up to 1000-fold when linked to endogenous or heterologous promoters, with synthesis beginning at the normal mRNA start site. Enhancers are also active when placed upstream or downstream from the transcription initiation site, in either normal or flipped orientation, or at a distance of more than 1000 nucleotides from the promoter. See, e.g., Maniatis (1987) *Science* 236:1237 and Alberts (1989) *Molecular Biology of the Cell*, 2nd Ed. (or later). Enhancers derived from viruses may be particularly useful, because they typically have a broader host range. Examples include the SV40 early gene enhancer (see Dijkema (1985) *EMBO J.* 4:761) and the enhancer/promoters derived from the long terminal repeat (LTR) of the RSV (see Gorman (1982) *Proc. Natl. Acad. Sci.* 79:6777) and from human cytomegalovirus (see Boshart (1985) *Cell* 41:521). Additionally, some enhancers are regulatable and become active only in the presence of an inducer, such as a hormone or metal ion (see Sassone-Corsi and Borelli (1986) *Trends Genet.* 2:215); Maniatis (1987) *Science* 236:1237), In addition, the expression vector can and will typically also include a termination sequence and poly (A) addition sequences which are operably linked to the heterologous coding sequence.

Sequences that cause amplification of the gene may also be desirably included in the expression vector or in another vector that is co-translated with the expression vector, as are sequences which encode selectable markers. Selectable markers for mammalian cells are known in the art, and include, for example, thymidine kinase, dihydrofolate reductase (together with methotrexate as a DHFR amplifier), aminoglycoside phosphotransferase, hygromycin B phosphotransferase, asparagine synthetase, adenosine deaminase, metallothionien, and antibiotic resistant genes such as neomycin.

Mammalian cell lines available as hosts for expression are known in the art and include many immortalized cell lines available from the American Type Culture Collection (ATCC) as well as primary cultured cells and established cell lines, including but not limited to Vero, HEp-2, 3T3, COS, CHO, HeLa, BHK, MDCK, 293, WI38, Hep G2, MRC-5, and many others.

Host cells containing the vectors (e.g., expression vectors) described above are also a feature of the invention. The host cell can be a eukaryotic cell, such as a mammalian cell, a yeast cell, or a plant cell, or the host cell can be a prokaryotic cell, such as a bacterial cell. Introduction of the construct into the host cell can be effected by calcium phosphate transfection, DEAE-Dextran mediated transfection, electroporation, encapsulation of the polynucleotide(s) in liposomes, direct microinjection of the DNA into nuclei, or other common techniques (see, e.g., Davis, L., Dibner, M., and Battey, I. (1986) *Basic Methods in Molecular Biology*).

A host cell strain is optionally chosen for its ability to modulate the expression of the inserted sequences or to process the expressed protein in the desired fashion. Such modifications of the protein include, but are not limited to, acetylation, carboxylation, glycosylation, phosphorylation, lipidation and acylation. Post-translational processing which cleaves a precursor form into a mature form of the protein is sometimes important for correct insertion, folding and/or function. Different host cells have specific cellular machinery and characteristic mechanisms for such post-translational activities and can be chosen to ensure the correct modification and processing of the introduced, foreign protein.

Host cells transformed with a nucleotide sequence encoding a polypeptide of the invention are optionally cultured under conditions suitable for the expression and recovery of the encoded protein from cell culture. The protein or fragment thereof produced by a recombinant cell can be secreted, membrane-bound, or contained intracellularly, depending on the sequence -and/or the vector used.

Following transduction of a suitable host cell line or strain and growth of the host cells to an appropriate cell density, the selected promoter is induced if necessary by appropriate means (e.g., temperature shift or chemical induction) and cells are cultured for an additional period. The secreted polypeptide product is then recovered from the culture medium. Alternatively, cells can be harvested by centrifugation, disrupted by physical or chemical means, and the resulting crude extract retained for further purification. Eukaryotic or microbial cells employed in expression of proteins can be disrupted by any convenient method, including freeze-thaw cycling, sonication, mechanical disruption, or use of cell lysing agents, or other methods, which are well know to those skilled in the art.

Expressed polypeptides can be recovered and purified from recombinant cell cultures by any of a number of methods well known in the art, including ammonium sulfate or ethanol precipitation, acid extraction, anion or cation exchange chromatography, phosphocellulose chromatography, hydrophobic interaction chromatography, affinity chromatography (e.g., using any of the tagging systems noted herein), hydroxylapatite chromatography, and lectin chromatography. Protein refolding steps can be used, as desired, in completing configuration of the mature protein. Finally, high performance liquid chromatography (HPLC) can be employed in the final purification steps. In addition to the references noted above, a variety of purification methods are well known in the art, including, e.g., those set forth in Deutscher, *Methods in Enzymology Vol.* 182*: Guide to Protein Purification*, Academic Press, Inc. N.Y. (1990); Sandana (1997) *Bioseparation of Proteins*, Academic Press, Inc.; Bollag et al. (1996) *Protein Methods*, *2nd Edition* Wiley-Liss, NY; Walker (1996) *The Protein Protocols Handbook* Humana Press, NJ; Harris and Angal (1990) *Protein Purification Applications: A Practical Approach* IRL Press at Oxford, Oxford, U.K.; Scopes (1993) *Protein Purification: Principles and Practice* 3*rd Edition Springer Verlag, NY; Janson and Ryden (*1998) *Protein Purification: Principles, High Resolution Methods and Applications, Second Edition* Wiley-VCH, NY; and Walker (1998) *Protein Protocols on CD-ROM* Humana Press, NJ.

Alternatively, cell-free transcription/translation systems can be employed to produce polypeptides comprising an amino acid sequence or subsequence encoded by the polynucleotides of the invention. A number of suitable in vitro transcription and translation systems are commercially available. A general guide to in vitro transcription and translation protocols is found in Tymms (1995) *In vitro Transcription and Translation Protocols: Methods in Molecular Biology* Volume 37, Garland Publishing, NY. Cell free transcription/translation systems can be particularly useful for the production of polypeptides, including proteins for administration to human subjects.

In addition, the polypeptides, or subsequences thereof, e.g., subsequences comprising antigenic peptides, can be produced manually or by using an automated system, by direct peptide synthesis using solid-phase techniques (see, e.g., Stewart et al. (1969) *Solid-Phase Peptide Synthesis*, WH Freeman Co, San Francisco; Merrifield J (1963) *J. Am. Chem. Soc.* 85:2149-2154). Exemplary automated systems include the Applied Biosystems 431A Peptide Synthesizer (Perkin Elmer, Foster City, Calif.). If desired, subsequences can be chemically synthesized separately, and combined using chemical methods to provide full-length polypeptides.

Modified Amino Acids

Expressed polypeptides of the invention can contain one or more modified amino acid. The presence of modified amino acids can be advantageous in, for example, (a) increasing polypeptide serum half-life, (b) reducing polypeptide antigenicity or (c) increasing polypeptide storage stability. Amino acid(s) are modified, for example, co-translationally or post-translationally during recombinant production (e.g., N-linked glycosylation at N-X-S/T motifs during expression in mammalian cells) or are modified by synthetic means (e.g., via PEGylation).

Non-limiting examples of a modified amino acid include a glycosylated amino acid, a sulfated amino acid, a prenlyated (e.g., famesylated, geranylgeranylated) amino acid, an acetylated amino acid, an acylated amino acid, a PEG-ylated amino acid, a biotinylated amino acid, a carboxylated amino acid, a phosphorylated amino acid, and the like, as well as amino acids modified by conjugation to, e.g., lipid moieties or other organic derivatizing agents. References adequate to guide one of skill in the modification of amino acids are replete throughout the literature. Example protocols are found in Walker (1998) *Protein Protocols on CD-ROM* Human Press, Towata, N.J.

Antibodies

The polypeptides of the invention can be used to produce antibodies specific for the polypeptides comprising amino acid sequences or subsequences encoded by the polynucleotides of the invention. Antibodies specific for antigenic peptides encoded by, e.g., SEQ ID NO:1 (e.g., SEQ ID NOs:2-11), and related variant polypeptides are useful, e.g., for diagnostic and therapeutic purposes, e.g., related to the activity, distribution, and expression of target polypeptides.

Antibodies specific for the polypeptides of the invention can be generated by methods well known in the art. Such antibodies can include, but are not limited to, polyclonal, monoclonal, chimeric, humanized, single chain, Fab fragments and fragments produced by an Fab expression library.

Polypeptides do not require biological activity for antibody production. However, the polypeptide or oligopeptide is antigenic. Peptides used to induce specific antibodies typically have an amino acid sequence of at least about 5 amino acids, and often at least 10 or 20 amino acids. Short stretches of a polypeptide, e.g., encoded by a polynucleotide of the invention such a sequence selected from SEQ ID NO:1 (such as a polypeptide selected from among SEQ ID NOs:2-11) can optionally be fused with another protein, such as keyhole limpet hemocyanin (KLH), and antibodies produced against the fusion protein or polypeptide.

Numerous methods for producing polyclonal and monoclonal antibodies are known to those of skill in the art, and can be adapted to produce antibodies specific for the polypeptides or peptides of the invention. See, e.g., Coligan (1991) *Current Protocols in Immunology* Wiley/Greene, NY; and Harlow and Lane (1989) *Antibodies: A Laboratory Manual* Cold Spring Harbor Press, NY; Stites et al. (eds.) *Basic and Clinical Immunology* ($4^{th}$ ed.) Lange Medical Publications, Los Altos, Calif., and references cited therein; Goding (1986) *Monoclonal Antibodies: Principles and Practice* (2d ed.) Academic Press, New York, N.Y.; *Fundamental Immunology*, e.g., $4^{th}$ Edition (or later),W. E. Paul (ed.), Raven Press, N.Y. (1998); and Kohler and Milstein (1975) *Nature* 256: 495-497. Other suitable techniques for antibody preparation include selection of libraries of recombinant antibodies in phage or similar vectors. See, Huse et al. (1989) *Science* 246: 1275-1281; and Ward, et al. (1989) *Nature* 341: 544-546. Specific monoclonal and polyclonal antibodies and antisera will usually bind with a $K_D$ of at least about 0.1 μM, preferably at least about 0.01 μM or better, and most typically and preferably, 0.001 μM or better.

For certain therapeutic applications (e.g., administration of an antibody or antiserum specific for one or more strains of RSV to provide passive immunity to a subject, e.g., a human, to prevent or decrease the severity of RSV disease), humanized antibodies are desirable. Detailed methods for preparation of humanized antibodies can be found in U.S. Pat. No. 5,482,856. Additional details on humanization and other antibody production and engineering techniques can be found in Borrebaeck (ed) (1995) *Antibody Engineering*. *$2^{nd}$ Edition* Freeman and Company, NY (Borrebaeck); McCafferty et al. (1996) *Antibody Engineering, A Practical Approach* IRL at Oxford Press, Oxford, England (McCafferty), and Paul (1995) *Antibody Engineering Protocols* Humana Press, Towata, N.J. (Paul). Additional details regarding specific procedures can be found, e.g., in Ostberg et al. (1983) *Hybridoma* 2: 361-367, Ostberg, U.S. Pat. No. 4,634,664, and Engelman et al. U.S. Pat. No. 4,634,666.

Diagnostic Assays

The novel nucleic acid sequences of the present invention can be used in diagnostic assays to detect RSV in a sample, to detect RSV B9320-like sequences, and to detect strain differences in clinical isolates of RSV using either chemically synthesized or recombinant RSV B9320 polynucleotide fragments, e.g., selected from SEQ ID NO:1. For example, fragments of the novel B9320 sequences (SEQ ID NO:1) comprising at least between 10 and 20 nucleotides can be used as primers to amplify nucleic acids using polymerase chain reaction (PCR) methods well known in the art (e.g., reverse transcription-PCR) and as probes in nucleic acid hybridization assays to detect target genetic material such as RSV RNA in clinical specimens.

The novel RSV B9320 polynucleotide sequences can be used in their entirety or as fragments to detect the presence of RNA sequences or transcription products in cells, tissues, samples and the like using hybridization techniques known in the art or in conjunction with one of the methods discussed herein. The probes can be either DNA or RNA molecules, such as fragments of viral RNA, isolated restriction fragments of cloned DNA, cDNAs, amplification products, transcripts, and oligonucleotides, and can vary in length from oligonucleotides as short as about 10 nucleotides in length to viral RNA fragments or cDNAs in excess of one or more kilobases. For example, in some embodiments, a probe of the invention includes a polynucleotide sequence or subsequence (e.g., a unique subsequence) selected from SEQ ID NO:1 or sequences complementary thereto. Preferably the polynucleotide sequence (or subsequence) is selected from a portion of SEQ ID NO:1 that includes at least a subsequence that is not included in SEQ ID NOs:14-19. Alternatively, polynucleotide sequences that are variants of one of the above designated sequences are used as probes. Most typically, such variants include one or a few nucleotide variations. For example, pairs (or sets) of oligonucleotides can be selected, in which the two (or more) polynucleotide sequences are substantially identical variants of each other, wherein one polynucleotide sequence or set corresponds identically to a first viral strain (e.g., B9320) and the other sequence(s) or set(s) correspond identically to additional viral strains (e.g., B1, A2, etc.). Such pairs of oligonucleotide probes are particularly useful, for example, in the context of an allele specific hybridization experiment to determine the identity of an RSV virus or viral nucleic acid, e.g., for diagnostic or monitoring purposes. In other applications, probes are selected that are more or less divergent, that is probes that are at least about 70% (or 80%, 90%, 95%, 98%, or 99%) identical are selected.

The probes of the invention, e.g., as exemplified by unique subsequences selected from SEQ ID NO:1, can also be used to identify additional useful polynucleotide sequences (such as to characterize additional strains of RSV) according to procedures routine in the art. In one set of preferred embodiments, one or more probes, as described above, are utilized to screen libraries of expression products or cloned viral nucleic acids (i.e., expression libraries or genomic libraries) to identify clones that include sequences identical to, or with significant sequence identity to SEQ ID NO:1. In turn, each of these identified sequences can be used to make probes, including pairs or sets of variant probes as described above. It will be understood that in addition to such physical methods as library screening, computer assisted bioinformatic approaches, e.g., BLAST and other sequence homology search algorithms, and the like, can also be used for identifying related polynucleotide sequences.

The probes of the invention are particularly useful for detecting the presence and for determining the identity of RSV nucleic acids in cells, tissues or other biological samples (e.g., a nasal wash or bronchial lavage). For example, the probes of the invention are favorably utilized to determine whether a biological sample, such as a subject (e.g., a human subject) or model system (such as a cultured cell sample) has been exposed to, or become infected with, RSV. Detection of hybridization of the selected probe to nucleic acids originating in (e.g., isolated from) the biological sample or model system is indicative of exposure to or infection with the virus (or a related virus) from which the probe polynucleotide is selected. For example, a polynucleotide sequence that hybridizes preferentially to a subsequence of SEQ ID NO:1 as compared to the corresponding subsequence of SEQ ID NO:13 (or the genome of another naturally occurring RSV strain) can be used to distinguish RSV B 9320 from RSV B1 (or another RSV strain).

It will be appreciated that probe design is influenced by the intended application. For example, where several allele-specific probe-target interactions are to be detected in a single assay, e.g., on a single DNA chip, it is desirable to have similar melting temperatures for all of the probes. Accordingly, the length of the probes are adjusted so that the melting temperatures for all of the probes on the array are closely similar (it will be appreciated that different lengths for different probes may be needed to achieve a particular $T_m$ where different probes have different GC contents). Although melting temperature is a primary consideration in probe design, other factors are optionally used to further adjust probe construction, such as selecting against primer self-complementarity and the like.

In other circumstances, e.g., relating to functional attributes of cells or organisms expressing the polynucleotides and polypeptides of the invention, probes that are polypeptides, peptides or antibodies are favorably utilized. For example, polypeptides, polypeptide fragments and peptides encoded by or having subsequences encoded by the polynucleotides of the invention, e.g., SEQ ID NO:1, are favorably used to identify and isolate antibodies or other binding proteins, e.g., from phage display libraries, combinatorial libraries, polyclonal sera, and the like.

Antibodies specific for a polypeptide subsequence encoded by any subsequence (e.g., unique subsequence) or ORF of SEQ ID NO:1 are likewise valuable as probes for evaluating expression products, e.g., from cells or tissues. For example, suitable polypeptide sequences are selected from among the amino acid sequences represented by SEQ ID NOs:2-11. In addition, antibodies are particularly suitable for evaluating expression of proteins comprising amino acid subsequences encoded by SEQ ID NO:1 (e.g., SEQ ID NOs:2-11), e.g., in a sample from a subject infected with or exposed to RSV. Antibodies can be directly labeled with a detectable reagent as described below, or detected indirectly by labeling of a secondary antibody specific for the heavy chain constant region (i.e., isotype) of the specific antibody. Additional details regarding production of specific antibodies are provided above in the section entitled “Antibodies.”

Labeling and Detecting Probes

Numerous methods are available for labeling and detection of the nucleic acid and polypeptide (or peptide or antibody) probes of the invention. These include: 1) fluorescence (using, e.g., fluorescein, Cy-5, rhodamine or other fluorescent tags); 2) isotopic methods, e.g., using end-labeling, nick translation, random priming, or PCR to incorporate radioactive isotopes into the probe polynucleotide/oligonucleotide; 3) chemifluorescence, e.g., using alkaline phosphatase and the substrate AttoPhos (Amersham) or other substrates that produce fluorescent products; 4) chemiluminescence (e.g., using either horseradish peroxidase and/or alkaline phosphatase with substrates that produce photons as breakdown products; kits providing reagents and protocols are available from such commercial sources as Amersham, Boehringer-Mannheim, and Life TechnologieslGibco BRL); and, 5) colorimetric methods (again using, e.g., horseradish peroxidase and/or alkaline phosphatase with substrates that produce a colored precipitate; kits are available from Life Technologies/Gibco BRL, and Boehringer-Mannheim). Other methods for labeling and detection will be readily apparent to one skilled in the art.

More generally, a probe can be labeled with any composition detectable by spectroscopic, photochemical, biochemical, immunochemical, electrical, optical, chemical or other available means. Useful labels in the present invention include spectral labels such as fluorescent dyes (e.g., fluorescein isothiocyanate, Texas red, rhodamine, and the like), radiolabels (e.g., $^{3}H$, $^{125}I$, $^{35}S$, $^{14}C$, $^{32}P$, $^{33}P$, etc.), enzymes (e.g., horse-radish peroxidase, alkaline phosphatase, etc.), spectral calorimetric labels such as colloidal gold or colored glass or plastic (e.g. polystyrene, polypropylene, latex, etc.) beads. The label may be coupled directly or indirectly to a component of the detection assay (e.g., a probe, such as an oligonucleotide, isolated DNA, amplicon, restriction fragment, or the like) according to methods well known in the art. As indicated above, a wide variety of labels may be used, with the choice of label depending on sensitivity required, ease of conjugation with the compound, stability requirements, available instrumentation, and disposal provisions. In general, a detector which monitors a probe-target nucleic acid hybridization is adapted to the particular label which is used. Typical detectors include spectrophotometers, phototubes and photodiodes, microscopes, scintillation counters, cameras, film and the like, as well as combinations thereof. Examples of suitable detectors are widely available from a variety of commercial sources known to persons of skill. Commonly, an optical image of a substrate comprising a nucleic acid array with particular set of probes bound to the array is digitized for subsequent computer analysis.

Because incorporation of radiolabeled nucleotides into nucleic acids is straightforward, this detection represents one favorable labeling strategy. Exemplary technologies for incorporating radiolabels include end-labeling with a kinase or phosphatase enzyme, nick translation, incorporation of radio-active nucleotides with a polymerase and many other well known strategies.

Fluorescent labels are desirable, having the advantage of requiring fewer precautions in handling, and being amenable to high-throughput visualization techniques. Preferred labels are typically characterized by one or more of the following: high sensitivity, high stability, low background, low environmental sensitivity and high specificity in labeling. Fluorescent moieties, which are incorporated into the labels of the invention, are generally are known, including Texas red, fluorescein isothiocyanate, rhodamine, etc. Many fluorescent tags are commercially available from SIGMA chemical company (Saint Louis, Mo.), Molecular Probes (Eugene, Oreg.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), and Applied Biosystems (Foster City, Calif.) as well as other commercial sources known to one of skill. Similarly, moieties such as digoxygenin and biotin, which are not themselves fluorescent but are readily used in conjunction with secondary reagents, i.e., anti-digoxygenin antibodies, avidin (or streptavidin), that can be labeled, are suitable as labeling reagents in the context of the probes of the invention.

The label is coupled directly or indirectly to a molecule to be detected (a product, substrate, enzyme, or the like) according to methods well known in the art. As indicated above, a wide variety of labels are used, with the choice of label depending on the sensitivity required, ease of conjugation of the compound, stability requirements, available instrumentation, and disposal provisions. Non radioactive labels are often attached by indirect means. Generally, a ligand molecule (e.g., biotin) is covalently bound to a nucleic acid such as a probe, primer, amplicon, or the like. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with labeled anti-ligands. Alternatively, any haptenic or antigenic compound can be used in combination with an antibody. Labels can also be conjugated directly to signal generating compounds, e.g., by conjugation with an enzyme or fluorophore or chromophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. Means of detecting labels are well known to those of skill in the art. Thus, for example, where the label is a radioactive label, means for detection include a scintillation counter or photographic film as in autoradiography. Where the label is optically detectable, typical detectors include microscopes, cameras, phototubes and photodiodes and many other detection systems which are widely available.

Production of Recombinant Virus

Negative strand RNA viruses can be genetically engineered and recovered using a recombinant reverse genetics approach (U.S. Pat. No. 5,166,057 to Palese et al.). Although this method was originally applied to engineer influenza viral genomes (Luytjes et al. (1989) *Cell* 59:1107-1113; Enami et al. (1990) *Proc. Natl. Acad. Sci. USA* 92:11563-11567), it has been successfully applied to a wide variety of segmented and nonsegmented negative strand RNA viruses, e.g., rabies (Schnell et al. (1994) *EMBO J.* 13: 4195-4203); VSV (Lawson et al. (1995) *Proc. Natl. Acad. Sci. USA* 92: 4477-4481); measles virus (Radecke et al.(1995) *EMBO J.* 14:5773-5784); rinderpest virus (Baron and Barrett (1997) *J. Virol.* 71: 1265-1271); human parainfluenza virus (Hoffman and Banerjee (1997) *J. Virol.* 71: 3272-3277; Dubin et al. (1997) *Virology* 235:323-332); SV5 (He et al. (1997) *Virology* 237: 249-260); canine distemper virus (Gassen et al. (2000) *J. Virol.* 74:10737-44); and Sendai virus (Park et al. (1991) *Proc. Natl. Acad. Sci. USA* 88: 5537-5541; Kato et al. (1996) *Genes to Cells* 1:569-579).

Recently, a system for producing recombinant subgroup A RSV (e.g., attenuated recombinant RSV suitable for vaccine production) has been described by the inventors and coworkers in WO 02/44334 by Jin et al. entitled "Recombinant RSV virus expression systems and vaccines," the disclosure of which is incorporated herein in its entirety. Rescue of subgroup A RSV has also been described, e.g., in Jin et al. (1998) *Virology* 251:206-214 and Collins et al. (1995) *Proc. Natl. Acad. Sci.* USA 92:11563-11567. (See also e.g., Jin et al. (2000) *J. Virol.* 74:74-82; Jin et al. (2000) *Virology* 273:210-218; Cheng et al. (2001) *Virology* 283:59-68; Tang et al. (2001) *J. Virol.* 75:11328-11335; U.S. patent application Ser. No. 60/444,287 (filed on Jan. 31, 2003) by Jin et al. entitled "Functional mutations in respiratory syncytial virus"; and U.S. patent application Ser. No. 10/672,302 (filed on Sep. 26, 2003) by Jin et al. entitled "Functional mutations in respiratory syncytial virus.") Rescue of subgroup B RSV is briefly described below and in the examples herein.

In brief, recombinant RSV incorporating the nucleic acids of this invention are generated, for example, in a suitable cell line (e.g., Vero or Hep-2 cells) by transfection of the cells with an antigenomic cDNA. Typically, the antigenomic cDNA is flanked by a T7 RNA polymerase promoter and a hepatitis delta virus ribozyme plus the T7 transcriptional terminator. Plasmids expressing the viral N, P, and L proteins (and optionally also the M2-1 protein) are also introduced into the cells, and a T7 RNA polymerase is typically expressed in the transfected cells (e.g., by infection of the cells with a modified vaccinia virus Ankara expressing T7 RNA polymerase). Recombinant RSV can also be produced by infection of suitable cells with previously isolated recombinant virus. Techniques for propagation, separation from host cell cellular components, and/or further purification of RSV are well known to those skilled in the art.

Methods of producing recombinant RSV are a feature of the invention. In the methods, a host cell into which a vector comprising a nucleic acid of the invention has been introduced is cultured in a suitable culture medium under conditions permitting expression of the nucleic acid (e.g., coexpression of RSV N, P, and L and optionally M2-1 and/or T7 RNA polymerase). The recombinant respiratory syncytial virus is then isolated from the host cell and/or the medium. Typically, the nucleic acid comprises an entire RSV genome or antigenome. Alternatively, the nucleic acid can comprise a portion of an RSV genome or antigenome (e.g., one or more open reading frames encoding proteins to be assembled with an RSV genome from another source to form the recombinant virus).

Recombinant RSV (e.g., attenuated recombinant RSV) produced according to the methods described herein are also a feature of the invention, as are recombinant RSV (e.g., attenuated recombinant RSV) comprising one or more nucleic acids and/or polypeptides of the invention.

Cell Culture

Typically, propagation of a recombinant virus (e.g., recombinant RSV) is accomplished in the media compositions in which the host cell is commonly cultured. Suitable host cells for the replication of RSV include, e.g., Vero cells and HEp-2 cells. Typically, cells are cultured in a standard commercial culture medium, such as Dulbecco's modified Eagle's medium supplemented with serum (e.g., 10% fetal bovine serum), or in serum free medium, under controlled humidity and $CO_2$ concentration suitable for maintaining neutral buffered pH (e.g., at pH between 7.0 and 7.2). Optionally, the medium contains antibiotics to prevent bacterial growth, e.g., penicillin, streptomycin, etc., and/or additional nutrients, such as L-glutamine, sodium pyruvate, non-essential amino acids, additional supplements to promote favorable growth characteristics, e.g., trypsin, β-mercaptoethanol, and the like.

Procedures for maintaining mammalian cells in culture have been extensively reported, and are known to those of skill in the art. General protocols are provided, e.g., in Freshney (1983) *Culture of Animal Cells: Manual of Basic Technique*, Alan R. Liss, New York; Paul (1975) *Cell and Tissue Culture*, $5^{th}$ ed., Livingston, Edinburgh; Adams (1980) *Laboratory Techniques in Biochemistry and Molecular Biology-Cell Culture for Biochemists*, Work and Burdon (eds.) Elsevier, Amsterdam. Additionally, variations in such procedures adapted to the present invention are readily determined through routine experimentation.

Cells for production of RSV can be cultured in serum-containing or serum free medium. In some cases, e.g., for the preparation of purified viruses, it is desirable to grow the host cells in serum free conditions. For example, cells can be grown to the desired density in serum-containing medium, infected, and then maintained in serum-free medium. Cells can be cultured in small scale, e.g., less than 25 ml medium, culture tubes or flasks or in large flasks with agitation, in rotator bottles, or on microcarrier beads (e.g., DEAE-Dextran microcarrier beads, such as Dormacell, Pfeifer & Langen; Superbead, Flow Laboratories; styrene copolymer-tri-methylamine beads, such as Hillex, SoloHill, Ann Arbor) in flasks, bottles or reactor cultures. Microcarrier beads are small spheres (in the range of 100-200 microns in diameter) that provide a large surface area for adherent cell growth per volume of cell culture. For example a single liter of medium can include more than 20 million microcarrier beads providing greater than 8000 square centimeters of growth surface. For commercial production of viruses, e.g., for vaccine production, it is often desirable to culture the cells in a bioreactor or fermenter. Bioreactors are available in volumes from under 1 liter to in excess of 100 liters, e.g., Cyto3 Bioreactor (Osmonics, Minnetonka, Minn.); NBS bioreactors (New Brunswick Scientific, Edison, N.J.); and laboratory and commercial scale bioreactors from B. Braun Biotech International (B. Braun Biotech, Melsungen, Germany).

Other useful references, e.g. for cell isolation and culture (e.g., of bacterial cells containing recombinant nucleic acids, e.g., for subsequent nucleic acid isolation) include Freshney (1994) *Culture of Animal Cells, a Manual of Basic Technique*, third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg N.Y.) and Atlas and Parks (eds) *The Handbook of Microbiological Media* (1993) CRC Press, Boca Raton, Fla.

Introduction of Vectors Into Host Cells

Vectors, e.g., vectors incorporating RSV polynucleotides, are introduced (e.g., transfected) into host cells according to methods well known in the art for introducing heterologous nucleic acids into eukaryotic cells, including, e.g., calcium phosphate co-precipitation, electroporation, microinjection, lipofection, and transfection employing polyamine transfection reagents. For example, vectors, e.g., plasmids, can be transfected into host cells, e.g., Vero cells or Hep-2 cells, using the transfection reagent LipofectACE or Lipofectamine 2000 (Invitrogen) according to the manufacturer's instructions. Alternatively, electroporation can be employed to introduce vectors incorporating RSV genome segments into host cells.

Model Systems

Attenuated RSV, e.g. those described herein comprising all or part of SEQ ID NO:1 or variations thereof, can be tested in in vitro and in vivo models to confirm adequate attenuation, genetic stability, and/or immunogenicity for vaccine use. In in vitro assays, e.g., replication in cultured cells, the virus can be tested, e.g., for genetic stability, temperature sensitivity of virus replication and/or a small plaque phenotype. RSV can be further tested in animal models of infection. A variety of animal models, e.g., primate (e.g., chimpanzee, African green monkey) and rodent (e.g., cotton rat), are known in the art, as described briefly herein and in U.S. Pat. No. 5,922,326 to Murphy et al. (Jul. 13, 1999) entitled "Attenuated respiratory syncytial virus compositions"; U.S. Pat. No. 4,800,078; Meignier et al. eds. (1991) *Animal Models of Respiratory Syncvtial Virus Infection*, Merieux Foundation Publication; Prince et al. (1985) *Virus Res*. 3:193-206; Richardson et al. (1978) *J. Med. Virol*. 3:91-100; Wright et al. *Infect. Immun*. (1982) 37:397-400; and Crowe et al. (1993) *Vaccine* 11:1395-1404.

Methods and Compositions for Prophylactic Administration of Vaccines

One aspect of the invention provides immunogenic compositions (e.g., vaccines) comprising an immunologically effective amount of a recombinant RSV of the invention (e.g., an attenuated live recombinant RSV), an immunologically effective amount of a polypeptide of the invention, and/or an immunologically effective amount of a nucleic acid of the invention.

A related aspect of the invention provides methods for stimulating the immune system of an individual to produce a protective immune response against respiratory syncytial virus. In the methods, an immunologically effective amount of a recombinant RSV of the invention, an immunologically effective amount of a polypeptide of the invention, and/or an immunologically effective amount of a nucleic acid of the invention is administered to the individual in a physiologically acceptable carrier.

The RSV, polypeptides, and nucleic acids of the invention can be administered prophylactically in an appropriate carrier or excipient to stimulate an immune response specific for one or more strains of RSV. Typically, the carrier or excipient is a pharmaceutically acceptable carrier or excipient, such as sterile water, aqueous saline solution, aqueous buffered saline solutions, aqueous dextrose solutions, aqueous glycerol solutions, ethanol, or combinations thereof. The preparation of such solutions insuring sterility, pH, isotonicity, and stability is effected according to protocols established in the art. Generally, a carrier or excipient is selected to minimize allergic and other undesirable effects, and to suit the particular route of administration, e.g., subcutaneous, intramuscular, intranasal, oral, topical, etc. The resulting aqueous solutions can e.g., be packaged for use as is or lyophilized, the lyophilized preparation being combined with a sterile solution prior to administration Generally, the RSV (or RSV components) of the invention are administered in a quantity sufficient to stimulate an immune response specific for one or more strains of RSV (e.g., an immunologically effective amount of RSV or an RSV component is administered). Preferably, administration of RSV elicits a protective immune response. Dosages and methods for eliciting a protective anti-viral immune response, adaptable to producing a protective immune response against RSV, are known to those of skill in the art. See, e.g., U.S. Pat. No. 5,922,326; Wright et al. (1982) *Infect. Immun*. 37:397-400; Kim et al. (1973) *Pediatrics* 52:56-63; and Wright et al. (1976) *J. Pediatr*. 88:931-936. For example, virus can be provided in the range of about $10^3$-$10^6$ pfu (plaque forming units) per dose administered (e.g., $10^4$-$10^5$ pfu per dose administered). Typically, the dose will be adjusted based on, e.g., age, physical condition, body weight, sex, diet, mode and time of administration, and other clinical factors. The prophylactic vaccine formulation can be systemically administered, e.g., by subcutaneous or intramuscular injection using a needle and syringe or a needleless injection device. Preferably, the vaccine formulation is administered intranasally, e.g., by drops, aerosol (e.g., large particle aerosol (greater than about 10 microns)), or spray into the upper respiratory tract. While any of the above routes of delivery results in a protective systemic immune response, intranasal administration confers the added benefit of eliciting mucosal immunity at the site of entry of the virus. For intranasal administration, attenuated live virus vaccines are often preferred, e.g., an attenuated, cold adapted and/or temperature sensitive recombinant RSV, e.g., a chimeric recombinant RSV. As an alternative or in addition to attenuated live virus vaccines, killed virus vaccines, nucleic acid vaccines, and/or polypeptide subunit vaccines, for example, can be used, as suggested by Walsh et al. (1987) *J. Infect. Dis*. 155:1198-1204 and Murphy et al. (1990) *Vaccine* 8:497-502.

Typically, the attenuated recombinant RSV of this invention as used in a vaccine is sufficiently attenuated such that symptoms of infection, or at least symptoms of serious infection, will not occur in most individuals immunized (or otherwise infected) with the attenuated RSV. In embodiments in which viral components (e.g., the nucleic acids or polypeptides herein) are used as vaccine or immunogenic components, serious infection is not typically an issue. In some instances, the attenuated RSV (or RSV components of the invention) can still be capable of producing symptoms of mild illness (e.g., mild upper respiratory illness) and/or of dissemination to unvaccinated individuals. However, virulence is sufficiently abrogated such that severe lower respiratory tract infections do not typically occur in the vaccinated or incidental host.

While stimulation of a protective immune response with a single dose is preferred, additional dosages can be administered, by the same or different route, to achieve the desired prophylactic effect. In neonates and infants, for example, multiple administrations may be required to elicit sufficient levels of immunity. Administration can continue at intervals throughout childhood, as necessary to maintain sufficient levels of protection against wild-type RSV infection. Similarly, adults who are particularly susceptible to repeated or serious RSV infection, such as, for example, health care workers, day care workers, family members of young children, the elderly, and individuals with compromised cardiopulmonary function may require multiple immunizations to establish and/or maintain protective immune responses. Levels of induced immunity can be monitored, for example, by measuring amounts of neutralizing secretory and serum antibodies, and dosages adjusted or vaccinations repeated as necessary to elicit and maintain desired levels of protection.

Alternatively, an immune response can be stimulated by ex vivo or in vivo targeting of dendritic cells with virus. For example, proliferating dendritic cells are exposed to viruses in a sufficient amount and for a sufficient period of time to permit capture of the RSV antigens by the dendritic cells. The cells are then transferred into a subject to be vaccinated by standard intravenous transplantation methods.

Optionally, the formulation for prophylactic administration of the RSV also contains one or more adjuvants for enhancing the immune response to the RSV antigens. Suitable adjuvants include, for example: complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, bacille Calmette-Guerin (BCG), *Corynebacterium parvum*, and the synthetic adjuvant QS-21.

If desired, prophylactic vaccine administration of RSV can be performed in conjunction with administration of one or more immunostimulatory molecules. Immunostimulatory molecules include various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc. The immunostimulatory molecules can be administered in the same formulation as the RSV, or can be administered separately. Either the protein or an expression vector encoding the protein can be administered to produce an immunostimulatory effect.

Although vaccination of an individual with an attenuated RSV of a particular strain of a particular subgroup can induce cross-protection against RSV of different strains and/or subgroups, cross-protection can be enhanced, if desired, by vaccinating the individual with attenuated RSV from at least two strains, e.g., each of which represents a different subgroup. Similarly, the attenuated RSV vaccines of this invention can optionally be combined with vaccines that induce protective immune responses against other infectious agents.

Kits and Reagents

The present invention is optionally provided to a user as a kit. For example, a kit of the invention contains one or more nucleic acid, polypeptide, antibody, or cell line described herein. Most often, the kit contains a diagnostic nucleic acid or polypeptide (e.g., an antibody or a probe, e.g., as a cDNA microarray packaged in a suitable container) or other nucleic acid such as one or more expression vector. The kit typically further comprises one or more additional reagents, e.g., substrates, labels, primers, tubes and/or other accessories, reagents for collecting samples, buffers, hybridization chambers, cover slips, etc. The kit optionally further comprises an instruction set or user manual detailing preferred methods of using the kit components.

Digital Systems

The present invention provides digital systems, e.g., computers, computer readable media and integrated systems comprising character strings corresponding to the sequence information herein for the polypeptides and nucleic acids herein, including, e.g., those sequences listed herein and the various silent substitutions and conservative substitutions thereof. Integrated systems can further include, e.g., gene synthesis equipment for making genes and/or peptide synthesis equipment for making polypeptides corresponding to the character strings.

Various methods known in the art can be used to detect homology or similarity between different character strings, or can be used to perform other desirable functions such as to control output files, provide the basis for making presentations of information including the sequences and the like. Examples include BLAST, discussed supra. Computer systems of the invention can include such programs, e.g., in conjunction with one or more data file or data base comprising a sequence as noted herein.

Thus, different types of homology and similarity of various stringency and length can be detected and recognized in the integrated systems herein. For example, many homology determination methods have been designed for comparative analysis of sequences of biopolymers, for spell-checking in word processing, and for data retrieval from various databases. With an understanding of double-helix pair-wise complement interactions among 4 principal nucleobases in natural polynucleotides, models that simulate annealing of complementary homologous polynucleotide strings can also be used as a foundation of sequence alignment or other operations typically performed on the character strings corresponding to the sequences herein (e.g., word-processing manipulations, construction of figures comprising sequence or subsequence character strings, output tables, etc.).

Thus, standard desktop applications such as word processing software (e.g., Microsoft Word™ or Corel WordPerfec™) and database software (e.g., spreadsheet software such as Microsoft Excel™, Corel Quattro Pro™, or database programs such as Microsoft Access™ or Paradox™) can be adapted to the present invention by inputting a character string corresponding to one or more polynucleotides and polypeptides of the invention (either nucleic acids or proteins, or both). For example, a system of the invention can include the foregoing software having the appropriate character string information, e.g., used in conjunction with a user interface (e.g., a GUI in a standard operating system such as a Windows, Macintosh or LINUX system) to manipulate strings of characters corresponding to the sequences herein. As noted, specialized alignment programs such as BLAST can also be incorporated into the systems of the invention for alignment of nucleic acids or proteins (or corresponding character strings).

Systems in the present invention typically include a digital computer with data sets entered into the software system comprising any of the sequences herein. The computer can be, e.g., a PC (Intel x86 or Pentium chip- compatible DOS™, OS2™ WIDOWS™ WINDOWS NT™, WINDOWS95™, WINDOWS98™ LINUX based machine, a MACINTOSH™, Power PC, or a UNIX based (e.g., SUN™ work station) machine) or other commercially common computer which is known to one of skill. Software for aligning or otherwise manipulating sequences is available, or can easily be constructed by one of skill using a standard programming language such as Visualbasic, Fortran, Basic, Java, or the like.

Any controller or computer optionally includes a monitor which is often a cathode ray tube ("CRT") display, a flat panel display (e.g., active matrix liquid crystal display, liquid crystal display), or others. Computer circuitry is often placed in a box which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user and for user selection of sequences to be compared or otherwise manipulated in the relevant computer system.

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language, e.g., for instructing the operation of equipment, e.g., gene and/or peptide synthesis equipment, to carry out the desired operation.

The software can also include output elements for controlling nucleic acid synthesis (e.g., based upon a sequence or an alignment of a sequences herein) or other operations.

In an additional aspect, the present invention provides system kits embodying the methods, composition, systems and apparatus herein. System kits of the invention optionally comprise one or more of the following: (1) an apparatus, system, system component or apparatus component as described herein; (2) instructions for practicing the methods described herein, and/or for operating the apparatus or apparatus components herein and/or for using the compositions herein. In a further aspect, the present invention provides for the use of any apparatus, apparatus component, composition or kit herein, for the practice of any method or assay herein, and/or for the use of any apparatus or kit to practice any assay or method herein.

EXAMPLES

The following sets forth a series of experiments that demonstrate construction of RSV B9320 cDNAs and recovery of recombinant RSV from the cDNAs. It is understood that the examples and embodiments described herein are for illustrative purposes only and that various modifications or changes in light thereof will be suggested to persons skilled in the art and are to be included within the spirit and purview of this application and scope of the appended claims. Accordingly, the following examples are offered to illustrate, but not to limit, the claimed invention.

Materials and Methods

Cells and Viruses

Monolayer cultures of HEp-2 and Vero cells (obtained from the American Type Culture Collection, ATCC) were maintained in minimal essential medium (MEM) containing 5% fetal bovine serum. RSV A2 was obtained from the ATCC and grown in Vero cells in Opti-MEM. RSV subgroup B strain 9320, originally isolated in Massachusetts in 1977 (Hierholzer and Hirsch (1979) *J. Infect. Dis.* 140:826-828), was obtained from the ATCC and grown in Vero cells in Opti-MEM. Infected cells were maintained in serum-free Opti-MEM medium. Modified vaccinia virus Ankara expressing bacteriophage T7 RNA polymerase (MVA-T7; Sutter et al. (1995) *FEBS Lett.* 371:9-12 and Wyatt et al. (1995) *Virology* 210:202-205) was provided by Dr. Bernard Moss and amplified in CEK cells. Recombinant fowlpox virus expressing the T7 RNA polymerase (FPV-T7; Britton et al. (1996) "Expression of bacteriophage T7 RNA polymerase in avian and mammalian cells by a recombinant fowlpox virus" *J Gen Virol* 77:963-7) was obtained from Dr. Michael Skinner and grown in CEK cells.

Sequencing

RSV B9320 was grown in Vero cells and viral RNA was extracted from virus purified by ultracentrifugation from infected cell culture supernatant. 9320 genome sequences were obtained by sequencing DNA fragments generated by RT-PCR; the cDNA full length clone was also sequenced for comparison. All sequencing was done by Sequetech, Mountain View Calif. (www.sequetech.com).

Sequence Analysis

Sequence analysis was performed with Vector NTI version 6.0 and 8.0 ContigExpress and AlignX (Informax, Inc., www.informaxinc.com). Pairwise nucleic acid or polypeptide sequence alignments were performed with Vector NTI AlignX using default parameters set by the provider.

Construction of Full-length cDNA of RSV Subgroup B9320 Strain and Recovery of Infectious Respiratory Syncytial Virus from cDNA Construction of RSV 9320 Protein Expression Plasmids The 9320 N, P, and L protein coding regions were each cloned into a pCITE vector (Novagen, Madison, Wis.) under control of a T7 RNA polymerase promoter, to produce expression plasmids pB-N, pB-P, and pB-L.

pB-N: The N gene was amplified by RT-PCR from 9320 RNA extracted from virus particles purified by ultracentrifugation, using primers XC19 (5'-GATCCCATGGCTCTTAGCAAAGTCAAG-3' containing Nco I site, SEQ ID NO:20) and XC020 (5'-GTACGGATCCGTTGACTTATTTGCCCCGTAT-3' containing BamHI site, SEQ ID NO:21), and cloned between the NcoI and BamHI sites of pCITE2a/3a (Novagen) under the control of T7 promoter. This N protein expression plasmid was designated as AD740.

pB-P: The P gene was amplified by RT-PCR using primers XC17 (5'-GATCCCATGGAGAAGTTTTGCACCTG-3' with Nco I site, SEQ ID NO:22) and XC018 (5'-GTACGGATCCTGAGTGAGTTGATCACTG-3' with BamH I site, SEQ ID NO:23) and cloned between the NcoI and BamHI sites of pCITE2a/3a. This clone was designated as AD741.

pB-L: The L gene was cloned from three cDNA subclones obtained by RT-PCR and the clone was assigned as AD778.

To obtain one subclone, primers XC003 (5' GCTTGGCCATAACGATTCTATATCATCC-3', SEQ ID NO:24) and XC014 (5'-GGTAGTATAATGTTGTGCACTTTAG-3', SEQ ID NO:25) were used to amplify 9320 L from nt8511 to nt11685 and the cDNA was cloned into T/A vector (Invitrogen, pCR 2.1) to generate subclone AD762.

To obtain the second subclone, primers XC011 (5'-GGTCACGATTTACAAGATAAGCTCC-3', SEQ ID NO:26) and XC007 (5'-CAGATCCTTTTAACTTGCTACCTAGGCACA-3' SEQ ID NO:27) were used to amplify nt 11686 to nt14495 and the BamH I to Avr II fragment was cloned into the T/A vector as AD763.

To obtain the third subclone, primers XC009 (5'-CTTACGTGTGCCTAGGTAGCAAG-3', SEQ ID NO:28) and XC010 (5'-ACGAGAAAAAAAGTGTCAAAAACTAATGTCTCG, SEQ ID NO:29) were used to amplify 9320 nt 14495 to 15225, producing a first PCR product. To add the ribozyme cleavage sequence (RBZ) and T7 terminator sequence (T7ø), a second PCR product was obtained using XC015 (5'-GTTTTTGACACTTTTTTTCTCGTGGCCGGCATGGTCCCAGCC-3', SEQ ID NO:30) and XC016 (5'-GATCTAGAGCTCCAAGCTTGCGGCCGCGTCGAC-3' containing the Kpn I site, SEQ ID NO:31) as primers and pRSV-A2 full-length antigenomic cDNA (Jin et al. (1998) Virology 251:206-214) as template. Since primers XC010 and XC015 contained overlapping sequences, these two PCR products were annealed, extended and amplified by PCR using XC009 and XC016 as primers. The cDNA was cloned into the T/A vector and designated as AD764.

The three subclones were verified by sequence analysis. To join the three L subclones together, the AvrII and Kpn I fragment was removed from AD764 and cloned into AD763 and the larger clone was designated as AD767. The BamHI to NotI restriction fragment from nt11685 to the sequence downstream of the T7 terminator was removed from AD767 and cloned into pCITE2a/3a vector under the control of the T7 promoter and the plasmid was designated as AD766. The BamHI fragment from nt 8511 to nt 11685 was removed from clone AD762 and inserted into the BamH I site of AD766. The second BamHI site at position of nt 11685 was then knocked out by site-directed mutagenesis and the clone is designated as pB-L (AD778).

The functions of the pB-N, pB-P, and pB-L expression plasmids were examined by the RSV minigenome assay (as described in, e.g., Tang et al. (2002) Virology 302:207-216). A level of the CAT reporter gene similar to those of A2 expression plasmids was detected in cells transfected with pB-N, pB-P, pB-L and pRSVCAT minigenome, indicating all three of these plasmids are functional.

Assembly of Full-length Antigenomic cDNA of RSV 9320 Strain

An antigenomic cDNA spanning the entire RSV 9320 genome was assembled by sequential ligation of RSV cDNA fragments with the indicated unique restriction sites (FIG. 1). In brief, six cDNA fragments (B1-B6) were generated from 9320 viral RNA by RT-PCR using the pfu polymerase (Stratagene, La Jolla, Calif.) and cloned into a modified pET vector containing the RSV 9320 unique restriction enzyme sites (Xma I, Avr II, Sac I, BamH I, and BssHII). The Xma I-Avr II cDNA fragment (B1) containing the T7 RNA polymerase promoter proximal to the 5' antigenomic sense DNA was joined with the Avr II-Sac I cDNA fragment (B2) to form the B7 fragment (through a SacI site, as described below). The B7 fragment was used to replace the corresponding region in a full-length RSV A2-B9320 chimera containing the G, F and M2 sequence (B3). The Sac I restriction site at nt 2310 in the resulting pUC-B8 was mutated without affecting the coding sequence of the SH gene. The L gene fragment (B10) was assembled from B4 and B9 fragments. The hepatitis delta virus ribozyme (RBZ) and the T7 RNA polymerase terminator sequence was amplified from RSV A2 antigenomic cDNA (Jin et al. (1998) "Recombinant human respiratory syncytial virus (RSV) from cDNA and construction of subgroup A and B chimeric RSV" *Virology* 251:206-214) and ligated to the trailer sequence through PCR (B6). Ligation of B5 and B6 fragments were mediated through the Avr II and Not I restriction sites. The BamH I site at nt position 11685 was deleted from B10 cDNA by mutagenesis without affecting the protein coding sequence. The L gene (B10) was cloned into the chimeric clone that contained the 9320 B8 fragment and A2 L to replace the A2-L sequence through the BamH I and Not I restriction sites. The antigenomic cDNA clone (B11) encoding the complete RSV 9320 genome was designated pB9320C4. In addition, an antigenomic cDNA clone containing a single C to G change at the fourth position of the leader sequence was also obtained by mutagenesis and designated pB9320G4. A more detailed description of the cDNA construction follows.

Figure 2:
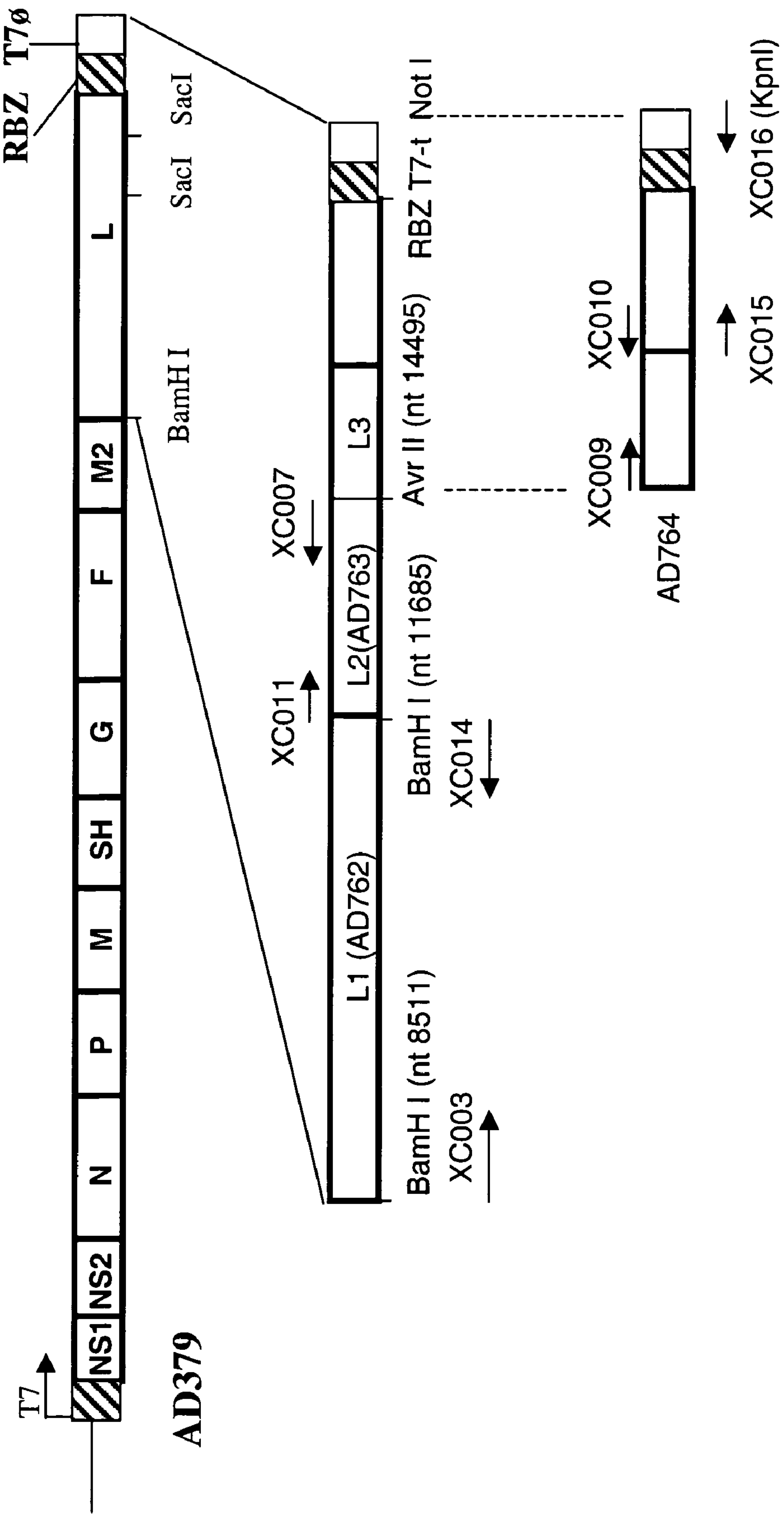
FIG. 2 schematically illustrates the cloning of pB-L, the assembly of the L coding region from three subclones. Positions of various subclones and primers used to assemble pB-L are indicated.
Figure 3:
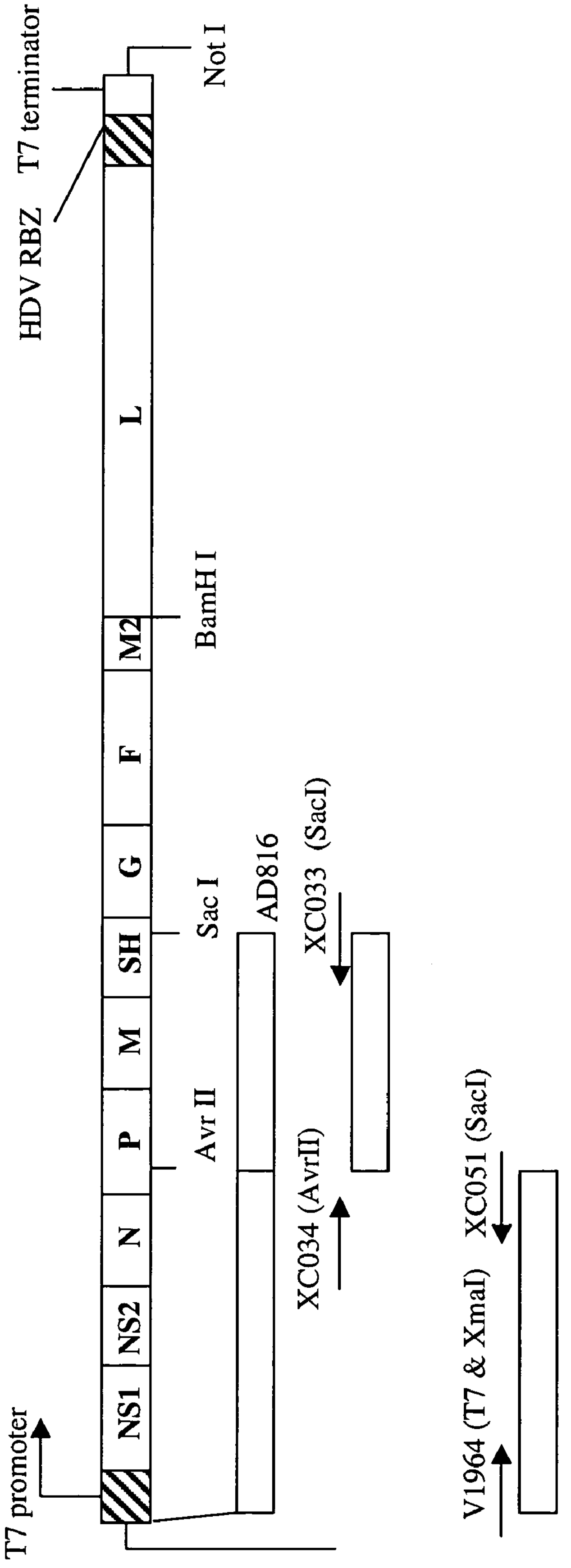
FIG. 3 schematically illustrates cloning of the 5' portion of the RSV 9320 antigenome. Positions of various subclones and primers are indicated.

Positions of various primers and subclones used in cloning the full length cDNA are illustrated in FIGS. 1-3. The 3' genome was amplified by RT-PCR using PFU polymerase with primer V1964 (5'-GGGTACCCCCGGGTAATACGACTCACTATAGGGACGGGAAAAAATG-3' containing Xma I restriction enzyme, the T7 promoter and the leader sequences, SEQ ID NO:32) and XC051 (5'-GTTAACTTAGAGCTCTACATCATC-3' containing the Sac I restriction site present in 9320 genome at position of nt 2310, SEQ ID NO:33). The PCR fragment was cloned between the Xma I and SacI sites of the modified pET vector (pET21b was cut with BspEI, and the pET21b was ligated with a polylinker with XmaI, SmaI, SacI, MscI, BamHI, SpeI, PmlI, and BssHII restriction sites to produce the modified pET-21b vector) and designated as AD803. A second PCR DNA that contained nt 2106 to 4494 was obtained by RT/PCR using XC034 (5'-GTGTGGTCCTAGGCAATGCAGCAG-3', SEQ ID NO:34) and XC032 (5'-GACACAGCATGATGGTAGAGCTCTATGTG-3', SEQ ID NO:35) as primers and was cloned into the Sac I site of the pET vector for sequence analysis. This SacI fragment was then moved to AD803 through the Sac I site in AD803 (producing B7). In order to ligate the cDNA encoding NS1, NS2, N, P, M and SH genes with the rest of the 9320 cDNA, the Sac I site at position nt 2310 was removed by mutagenesis and the resulting clone was designated as AD816. The Xma I to Sac I fragment from AD816 was released to replace the corresponding region of the A2 sequence in the chimeric cDNA AD379 that had the G and F genes of 9320 in place of A2 G and F genes (in a pUC19 backbone, Cheng et al. (2001) *Virology* 283:59-68). This clone was designated as AD827.

The cDNA containing the G, F, and M2 genes of 9320 strain was derived by RT-PCR using XC063 (5'-GCTAAGTGAACATAAAACATTCTGTAAC-3', SEQ ID NO:36) as RT primer and XC006 (5'-CCATTAATAATGGGATCCATTTTGTC-3' with SacI site, SEQ ID NO:37) and XC062 (5'-CACATAGAGCTCTACCATCATGCTGTGTC-3' with BamH I site, SEQ ID NO:38) as PCR primers and was initially cloned into pET vector as AD835 for sequence analysis. The SacI to BamH I fragment from AD835 was then moved to AD827 and the clone was designated as AD848.

The BamHI and NotI fragment from pB-L (AD869 encoding 9320 L with the two Sac I sites at positions of nt 10376 and nt 14951 knocked-out) was swapped into AD848 to complete the assembly of a full length antigenomic cDNA of RSV 9320.

Three mutations introduced by PCR during the cloning process were corrected by site-directed mutagenesis in their respective subclones, as follows. To reverse a His to Asn change in L at amino acid position 209, site-directed mutagenesis was performed to correct the His with primers XC081 (5'-CATGGTTAATACACTGGTTCAATT-TATATACA-3', SEQ ID NO:41) and XC082 (5'-TG-TATATAAATTGAACCAGTGTATTAACCATG-3', SEQ ID NO:42). To correct an Arg to Lys change in N at amino acid position 194 (nt 1748), site directed mutagenesis was performed with primers XC086 (5'-GTCTTAAAAAAC-GAAATAAAACGCTACAAGGGCCTCATACC-3', SEQ ID NO:43) and XC087 (5'GGTATGAGGCCCTTG-TAGCGTTTTATTTCGTTTTTTAAGAC-3', SEQ ID NO:44). A Ser to Asn change in NS1 at amino acid position 108 was not corrected.

The recombinant 9320 cDNA has the following genetic tags that are different from wild-type 9320 virus. (The enclosed sequence, SEQ ID NO:1, is the wild type RSV 9320 strain and does not reflect the recombinant DNA sequence.) First, Sac I sites at nt 2310, 10376 and 14951 were removed without changing the protein coding sequences, using the following primers: SacI at 2310 nt, XC049 (5'-GATGATG-TAGAGCTTTAAGTTAAC-3', SEQ ID NO:45) and XC050 (5'-GTTAACTTAAAGCTCTACATCATC-3', SEQ ID NO:46); SacI at 10376 nt, XC088 (5'-CTAACTGGTAAA-GAAAGAGAGCTTAGTGTAGGTAGAATGTTTGC-3', SEQ ID NO: 47) and XC089 (5'-GCAAACATTCTACCTA-CACTAAGCTCTCTTTCTTTACCAGTTAG-3', SEQ ID NO: 48); and SacI at 14951 nt, XC090 (5'-GTTTAACAAC-CAATGAGCTTAAAAAGCTGATTAAAATTAC-3', SEQ ID NO:49) and XC091 (5'-GTAATTTTAATCAGCTTT-TAAGCTCATTGGTTGTTAAAC-3', SEQ ID NO:50). The removal of the two Sac I sites at positions nt 10376 and 14951 in the L gene from AD864 to generate AD869 did not alter the amino acid sequence of L. Second, a BamH I site at nt 11685 was removed using primers XC067 (5'-CATTAATGAGG-GACCCACAGGCTTTAG-3', SEQ ID NO:39) and XC068 (5'-CTAAAGCCTGTGGGTCCCTCATTAATG-3', SEQ ID NO:40). Third, a Sac I site at nt 4477 was added using XC032 (5'-GACACAGCATGATGGTAGAGCTCTATGTG, SEQ ID NO:35).

It was previously reported that changing the C at the fourth nucleotide position of the leader region of RSV A2 to a G increased the promoter strength, resulting in increased transcription/replication of an RSV minigenome (Collins et al. (1993) "Rescue of a 7502-nucleotide (49.3% of full-length) synthetic analog of respiratory syncytial virus genomic RNA" Virology 195:252-256) and higher virus recovery efficiency (Jin et al. (1998) Virology 251:206-214). Thus, as noted, a 9320 cDNA with a C4 to G change in the leader sequence at the antigenomic sense was made to increase the promoter strength, and the resulting clone was designated as AD897 (pB9320G4).

Construction of G Gene Deletion Mutants

Two mutants were constructed to determine if the G gene of RSV B9320 strain is dispensable, e.g., for viral replication in tissue culture and/or an animal host. In one mutant, the entire open reading frame of the G gene was removed from the 9320 cDNA. In the other mutant, the region encoding the cysteine noose and heparin binding sites of G was removed from the 9320 cDNA.

For the RSV A2 strain, the G protein has been shown to be dispensable for virus replication in vitro (Techaarpomkul et al. (2001) "Functional analysis of recombinant respiratory syncytial virus deletion mutants lacking the small hydrophobic and/or attachment glycoprotein gene" *J Virol* 75:6825-34 and Teng et al. (2001) "Contribution of the respiratory syncytial virus G glycoprotein and its secreted and membrane-bound forms to virus replication in vitro and in vivo" *Virology* 289:283-96). However, rA2ΔG (RSV A2 lacking G) replicated poorly in HEp-2 cells, and its replication was attenuated in the respiratory tracts of mice. Previously, it was also shown that a cold-adapted RSV B1 strain, cp-52, had both the SH and G genes deleted (Karron et al. (1997) *Proc Natl Acad Sci USA* 94:13961-13966). However, this deletion mutant replicated poorly and was over-attenuated in animals and in humans. To determine whether the G protein was also dispensable for 9320 replication in vitro, an antigenomic cDNA was constructed in which the entire G gene (957 nt) including the gene start and gene end sequences was deleted from the cDNA and the new SH-F intergenic region contained 75 nt.

To construct the 9320 antigenomic cDNA that had the G gene deleted, deletion mutagenesis was performed on a pET-S/B cDNA subclone that contained sequences of the 9320 G, F and M2 genes using a pair of PCR primers flanking the G open reading frame in opposite orientations (5'-GATCCCAT-ACTAATAATTCATCATTATG-3', SEQ ID NO:51, and 5'-AGCAGAGAACCGTGATCTATCAAGCAAG-3', SEQ ID NO:52) using the ExSite PCR-based Site-Directed Mutagenesis Kit (Stratagene, La Jolla, Calif.). The deletion was confirmed by restriction enzyme digestion and nucleotide sequencing analysis. The Sac I-BamH I fragment containing only the F and M2 genes was introduced into pB9320G4, and the antigenomic cDNA was designated pB9320ΔG.

To delete only the cysteine noose and heparin binding sites of G (amino acids 164-197), a small cDNA fragment of nt 5179-5280 nt was deleted from the 9320 G gene using primers XC079 (5'-GTAATCATCTTTTGGTTTTTTTGGTGG-3', SEQ ID NO:53) and XC080 (5'-CCAACCATCAAAC-CCACAAACAAACCAACCGTC-3', SEQ ID NO:54). The cDNA containing the desired deletion was then removed from the subclone by digestion with Sac I and BamHI and shuffled into the full-length 9320 antigenomic cDNA. The resulting antigenomic cDNA was designated pB9320ΔHBS.

Recovery of Recombinant Viruses from cDNAs

Recovery of 9320 viruses (rg9320C4, rg9320G4, rg9320ΔG and rg9320ΔHBS) by reverse genetics (rg) was performed as described previously (Jin et al. (1998) *Virology* 251:206-214). Briefly, HEp-2 cells were infected with MVA-T7 at an m.o.i. of 5.0 and transfected with 0.4 μg of pB-N (pN), 0.4 μg of pB-P (pP), 0.2 μg of pB-L (pL), and 0.8 μg of pB9320C4, pB9320G4, pB9320ΔG or pB9320ΔHBS by Lipofectamine™ 2000 (Invitrogen, Carlsbad, Calif.). In some transfection reactions, 0.2 μg pRSV-M2-1 (encoding the RSV A2 M2-1 protein) was also included. Alternatively, Vero cells were infected with FPV-T7 (Britton et al. (1996) *J Gen Virol* 77:963-7) at an m.o.i. of 1.0 for 1 hr and transfected with the DNAs as above. Transfected cells were incubated at 35° C. Three days after transfection, the culture supernatant was used to infect Vero cells to amplify the recovered viruses. Six days after infection, the culture supernatant was harvested and virus-infected cells were identified by immunostaining using polyclonal anti-RSV A2 serum (Biogenesis, Kingston, N.H.). The recombinant virus from the culture supernatant was plaque purified and amplified in Vero cells.

Replication of rg9320C4, rg9320G4, rg9320ΔG in Tissue Culture

Replication of rg9320C4, rg9320G4 and rg9320ΔG in Vero and HEp-2 cells was compared with replication of wild type 9320. Vero or HEp-2 cell monolayers in 6-well plates were infected with each virus in duplicate at an m.o.i. of 0.1. After 1 hr adsorption at room temperature, the infected cells were washed with PBS three times and incubated with 2 ml of OptiMEM at 35° C. At 24 hr intervals, aliquots of 250 μl of culture supernatant were removed and stored at −80° C. prior to virus titration. Each aliquot taken was replaced with the same amount of fresh media. The virus titer was determined by plaque assay on Vero cells using an overlay consisting of 1% methylcellulose and 1×MEM/L15 (JRH Bioscience, Lenexa, Kans.) containing 2% FBS. After incubation at 35° C. for 6 days, the monolayers were fixed with methanol and plaques enumerated by immunostaining.

Western Blotting Analysis of Virus Infected Cells

Vero or HEp-2 cells were infected with virus at an m.o.i of 5.0 and the infected cells were lysed in Laemmli protein sample buffer (Bio-Rad, Hercules, Calif.). The cell lysates were electrophoresed on 12% polyacrylamide gels containing 0.1% SDS, and then transferred to a nylon membrane. The blots were incubated with either polyclonal anti-RSV A2 serum or a mixture of four monoclonal antibodies against the G protein of RSV B strain (2434DB3, 2218BD5, 2218AE7 and 2218DG7) obtained from Dr. Gregory Storch (Storch et al. (1991) "Antigenic and genomic diversity within group A respiratory syncytial virus" *J Infect Dis* 163:858-861). Viral proteins were visualized by incubation with horseradish peroxidase (HRP)-conjugated secondary antibodies followed by chemiluminescent detection (Amersham Biosciences, Piscataway, N.J.).

Results and Discussion

We have described the construction of a full-length antigenomic cDNA derived from RSV subgroup B9320 strain and recovery of infectious virus from the cDNA. The antigenomic sequence (complementary to the wild-type RSV 9320 genome and not including the changes introduced into our recombinant RSV) is listed as SEQ ID NO:1. The sequence is being deposited in GenBank (accession number AY353550).

The RSV 9320 genome contains 15,225 nucleotides and shares 97.8% and 86% identity compared to RSV B1 and A2 strains, respectively. As noted previously, the A2 genome contains 15,222 nucleotides; the B1 genome contains 15,225 nucleotides (Karron et al. (1997) *Proc Natl Acad Sci USA* 94:13961-13966). Like the RSV A2 strain, 9320 contains 10 transcriptional units encoding 11 proteins in the order of NS1/NS2/N/P/M/SH/G/F/M2-1/M2-2/L. Amino acid sequences of the proteins are also provided: NS1 is listed as SEQ ID NO:2, NS2 as SEQ ID NO:3, N as SEQ ID NO:4, P as SEQ ID NO:5, M as SEQ ID NO:6, SH as SEQ ID NO:7, G as SEQ ID NO:12, F as SEQ ID NO:8, M2-1 as SEQ ID NO:9, M2-2 as SEQ ID NO:10, and L as SEQ ID NO:11.

Table 3 lists the size of each of the 11 proteins for the 9320, B1, and A2 strains.

TABLE 3

| | Length of protein (amino acids) | | |
|---|---|---|---|
| | B9320 | B 1 | A2 |
| NS 1 | 139 | 139 | 139 |
| NS 2 | 124 | 124 | 124 |
| N | 391 | 391 | 391 |
| P | 241 | 241 | 241 |
| M | 256 | 256 | 256 |
| SH | 65 | 65 | 64 |
| G | 292 | 299 | 298 |
| F | 574 | 574 | 574 |
| M2-1 | 195 | 195 | 194 |
| M2-2 | 93 | 93 | 90 |
| L | 2166 | 2166 | 2165 |

Table 4 lists the length of the intergenic regions for the three RSV strains.

TABLE 4

| Length of intergenic region (nucleotides) | | | |
|---|---|---|---|
| INTERGENIC | B9320 | B 1 | A2 |
| NS 1/NS 2 | 16 | 16 | 19 |
| NS 2/N | 23 | 23 | 26 |
| N/P | 3 | 3 | 1 |
| P/M | 9 | 9 | 9 |
| M/SH | 9 | 9 | 9 |
| SH/G | 44 | 44 | 44 |
| G/F | 52 | 52 | 52 |
| F/M2 | 56 | 56 | 46 |
| GS L/GE M2 | 46 | 46 | 46 |

Table 5 lists the percentage amino acid sequence identity between strains B9320 and B1, 9320 and A2, and A2 and B1 for each protein. The SH, G and M2-2 proteins display the greatest differences between A2 and 9320, while the other proteins have an amino acid identity greater than 86%.

TABLE 5

| Amino acid identity (%) | | | |
|---|---|---|---|
| RSV Gene | B9320/B1 | B9320/A2 | A2/B1 |
| NS 1 | 99.3 | 86.3 | 87 |
| NS 2 | 98.4 | 90.4 | 92 |
| N | 99.7 | 95.9 | 96 |
| P | 98.3 | 90.9 | 91 |
| M | 99.6 | 92.2 | 91 |
| SH | 97.0 | 71.2 | 76 |
| G | 90.3 | 52.2 | 53 |
| F | 99.3 | 89.2 | 89 |
| M2-1 | 99.5 | 92.8 | N/A |
| M2-2 | 96.4 | 62.4 | 92 |
| L | 99.2 | 92.4 | 93 |

Recovery of Infectious 9320 from cDNA

A reverse genetics system for the A2 strain of subgroup A RSV was established several years ago (Collins et al. (1995) *Proc. Natl. Acad. Sci. USA* 92:11563-11567 and Jin et al. (1998) *Virology* 251:206-214). However, a system for recovery of subgroup B RSV has not previously been available. Herein we describe construction of an antigenomic cDNA derived from RSV subgroup B9320 and recovery of infectious RSV from cDNA. Similar to the A2 strain, rescue of 9320 depends on the expression of the viral polymerase proteins N, P and L. The M2-1 expression plasmid is not required for RSV 9320 recovery in either the FPV-T7 infected Vero or the MVA-T7 infected HEp-2 cells. However, M2-1 function was probably supplied by cryptic expression of the M2-1 protein from the transfected full-length antigenomic cDNA (Collins et al. (1999) *Virology* 259:251-255). The establishment of the reverse genetics system for the 9320 strain should greatly aid studies of viral protein structure and function of this divergent RSV subgroup.

Recovery of infectious RSV requires co-transfection of a minimum of three plasmids encoding the N, P and L proteins (Jin et al. (1998) *Virology* 251:206-214). In addition, the elongation function of M2-1 is also required for the virus recovery from cDNA (Collins et al. (1999) "Support plasmids and support proteins required for recovery of recombinant respiratory syncytial virus" *Virology* 259:251-255 and Collins et al. (1995) "Production of infectious human respiratory syncytial virus from cloned cDNA confirms an essential role for the transcription elongation factor from the 5' proximal open reading frame of the M2 mRNA in gene expression and provides a capability for vaccine development" *Proc. Natl.*

*Acad. Sci. USA* 92:11563-11567). The expression plasmids encoding the 9320 N, P, and L proteins were constructed and their functions were examined in the RSV minigenome assay using the pRSV/CAT replicon that contained the negative sense CAT gene flanked by the leader and trailer sequences derived from RSV A2 strain (Tang et al. (2001) *J Virol* 75:11328-11335). The minigenome assay indicated that the 9320 N, P and L expression plasmids functioned as well as those of RSV A2 strain.

To recover virus from RSV 9320 cDNA, pB9320C4 or pB9320G4 was transfected into MVA-T7 infected BEp-2 cells or FPV-T7 infected Vero cells together with the 9320 N, P and L expression plasmids with or without the RSV A2 M2-1 plasmid. Several days after inoculation of Vero cells with the transfected culture supernatant, syncytia formation was observed in the infected Vero cells and virus infection was confirmed by immunostaining.

Table 6 lists the recovery efficiency of recombinant RSV in the presence or absence of the M2-1 expression plasmid. FPV-T7 infected Vero cells or MVA-T7 infected HEp-2 cells were transfected with p9320C4 or p9320G4 in triplicate wells together with N, P, L expression plasmids with or without M2-1. Three days after transfection, the culture supernatants were titrated on Vero cells and the plaque numbers in pfu/ml from each well are shown. The average plaque number is given in parentheses.

The identity of the recombinant viruses generated from cDNA was analyzed by RT/PCR of each viral RNA using primer pairs spanning the introduced marker sites or the G deletion region. Digestion of the RT/PCR DNA product from nt 2104 to nt 3096 by the Sac I restriction enzyme showed that the Sac I site was present in 9320 virus but not in the recombinant viruses rg9320C4 and rg9320ΔG. Digestion of the RT/PCR product from nt 11593 to nt 11822 by BamH I confirmed that the BamH I site in the recombinant viruses was also abolished. RT/PCR using a pair of primers spanning the G gene confirmed that the G gene was deleted from rg9320ΔG, since its DNA product was approximately 1 kb shorter than that of rg9320. Sequencing of the G deletion junction region confirmed the expected deleted sequence.

The lack of G protein expression in rg9320ΔG infected cells was also confirmed by Western blotting analysis using monoclonal antibodies against the G protein of subgroup B RSV (Storch et al. (1991) *J Infect Dis* 163:858-861). The G protein was not expressed in rg9320ΔG-infected cells. Western blotting using a polyclonal antibody against RSV revealed an equivalent level of other viral proteins (F, N and P) synthesized by rg9320ΔG compared with rg9320G4.

Replication of the G Deletion Mutant in Tissue Culture

Figure 4B:
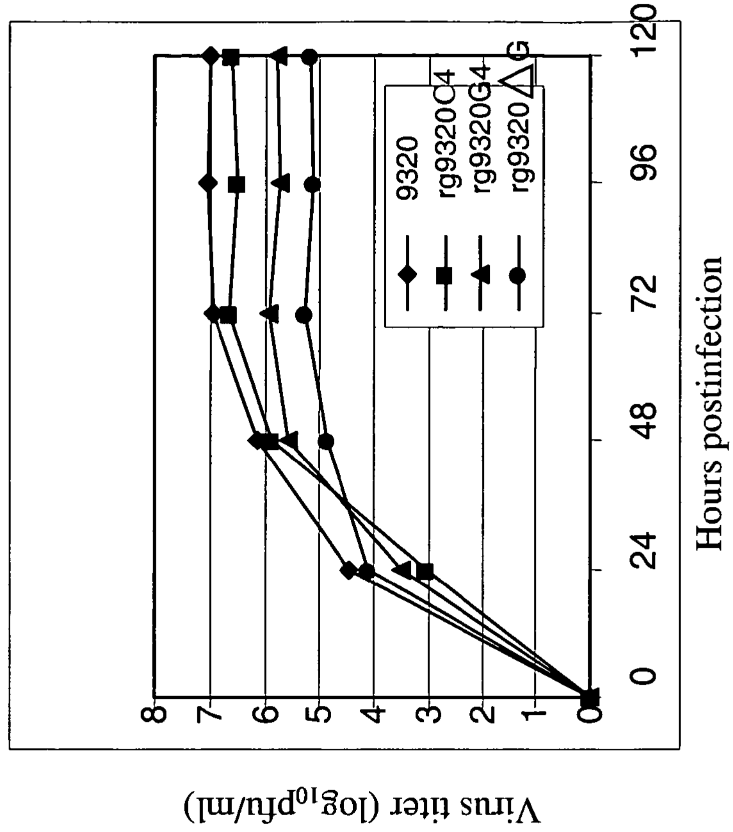
FIG. 4 presents line graphs illustrating the growth of wild type 9320 (diamonds), rg9320C4 (squares), rg9320G4(triangles), and rg9320ΔG (circles) in Vero cells (Panel A) and HEp-2 cells (Panel B). Vero or HEp-2 cells were infected with each virus at an m.o.i of 0.1 and incubated at 35° C. for 5 days. The viruses released into the culture supernatants at each day were titrated in Vero cells by plaque assay.
Figure 4A:
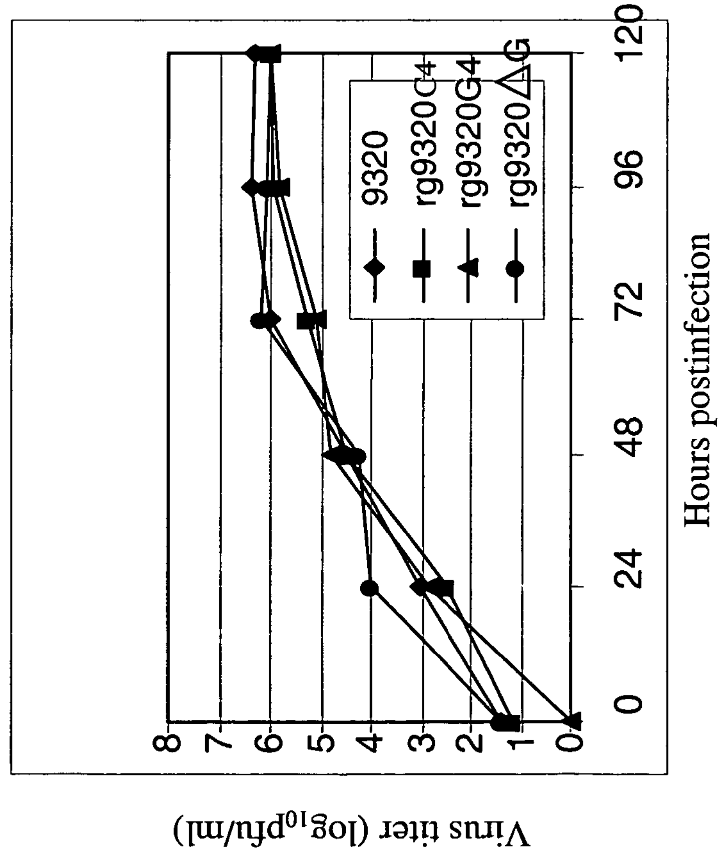

Replication of recombinant 9320 and its G deletion mutant were compared with replication of the biologically derived 9320 strain. Vero or HEp-2 cells were infected with 9320, rg9320C4, rg9320G4 or rg9320ΔG at an m.o.i. of 0.1, and the accumulated level of viruses released into the culture supernatant at each day was titrated in Vero cells. As shown in FIG. 4 Panel A, the growth kinetics of rg9320C4, rg9320G4 and rg9320ΔG were very similar to those of 9320 in Vero cells, reaching peak titers of 6.0 $\log_{10}$ pfu/ml at 96 hours post infection. In HEp-2 cells (FIG. 4 Panel B), rg9320C4 grew similarly to 9320 whereas rg9320G4 grew slightly slower. Replication of rg9320ΔG was reduced by 5-fold compared to rg9320G4.

TABLE 6

| | Average plaque number (pfu/ml) | | | |
|---|---|---|---|---|
| | FPV-T7 infected Vero cells (pfu/ml) | | MVA-T7 infected HEp-2 cells (pfu/ml) | |
| Virus | +M2-1 | −M2-1 | +M2-1 | −M2-1 |
| rg932004 | 70, 210, 93 (124) | 40, 40, 75 (52) | 55, 5, 3 (21) | 18, 0, 0 (6) |
| rg9320G4 | 1075, 1860, 1280 (1405) | 1140, 890, 900 (977) | 285, 3, 0 (96) | 18, 28, 0 (15) |

As shown in Table 6, rg9320G4 was rescued more efficiently than rg9320 in both the FPV-T7 infected Vero cells and the MVA-T7 infected HEp-2 cells. Inclusion of the M2-1 expression plasmid slightly increased rescue efficiency in both cell types.

For vaccine production, the vaccine is typically produced from a qualified cell line that is free of any adventitious agents. The BEp-2 cells currently used for recovery of infectious RSV A2 (e.g., Collins et al. (1995) *Proc. Natl. Acad. Sci. USA* 92:11563-11567 and Jin et al. (1998) *Virology* 251:206-214) are not suitable for vaccine production. Vero cells were therefore explored as the cell substrate for recovering 9320 virus from its cDNA. It was very difficult to recover virus from MVA-T7-infected Vero cells. FPV-T7 has been shown to have a less cytopathic effect in infected Vero cells and thus result in more efficient virus rescue of other viruses (Britton et al. (1996) *J Gen Virol* 77:963-7 and Das et al. (2000) "Improved technique for transient expression and negative strand virus rescue using fowlpox T7 recombinant virus in mammalian cells" *J Virol Meth* 89:119-127). Similarly, the recombinant RSV described here were more efficiently recovered from FPV-T7 infected Vero cells than from MVA-T7 infected cells, which may pave the way for recovering RSV vaccine candidates for clinical studies.

rg9320C4 and rg9320G4 were plaque purified and amplified in Vero cells, both reaching a titer of $1\times10^7$ pfu/ml. A recombinant virus with the G gene deleted from rg9320G4 was also obtained and the virus was designated rg9320ΔG.

The plaque morphology of rg9320ΔG was compared to that of rg9320G4 in Vero and HEp-2 cells. The spread of rg9320ΔG in Vero and HEp-2 cells in liquid medium was similar to that of rg9320G4. rg9320ΔG also formed plaques of similar size in both the Vero and HEp-2 cells. These data indicated that the deletion of G from 9320 did not have significant impact on virus replication in Vero and Hep-2 cells.

We have demonstrated that the G protein is not essential for RSV 9320 replication in tissue culture cells. However, deletion of G from RSV A2 strain severely affected virus replication in HEp-2 cells; rA2ΔG had a reduction of more than 3.0 $\log_{10}$ and did not form distinct plaques in HEp-2 cells (Teng et al. (2001) *Virology* 289:283-96). A study by Techaarpornkul et al. (Techaarpornkul et al. (2001) *J Virol* 75:6825-34) showed that rA2ΔG had 1-2 logs lower titer in HEp-2 cells and formed smaller plaques in HEp-2 cells. The G protein enhances virus binding to target cells, but it has no role in virus penetration once virus has attached the cells (Techaarpornkul et al. (2001) *J Virol* 75:6825-34). In Vero cells, rA2ΔG replicated as well as wt A2 strain, indicating an alternative pathway might be present in Vero cells for efficient virus entry that is independent of the G protein (Teng et al. (2001) *Virology* 289:283-96). Like rA2ΔG, rg9320ΔG replicated efficiently in Vero cells; however, in contrast to rA2ΔG, its replication was only slightly reduced in HEp-2 cells. The reduction of rg9320ΔG virus in HEp-2 cells was 5-fold compared to the parental rg9320G4 virus and the plaque size reduction in HEp-2 cells was also less apparent. Therefore, 9320 appears to be less dependent on the G protein for infectivity in HEp-2 cells than RSV A2.

rg9320ΔHBS, a recombinant 9320 virus with a partial deletion of G (the cysteine noose and heparin binding sites) was also recovered from cDNA as described above. Like rg9320ΔG, replication of rg9320ΔHBS in Vero cells is not significantly impaired.

Virus Replication in Cotton Rats

Subgroup B RSV typically replicates better in cotton rats than in mice. Therefore, in vivo replication of recombinant viruses rg9320C4, rg9320G4, rg9320ΔG and rg9320ΔHBS was examined in cotton rats (Sigmodon hispidus). Cotton rats in groups of five were inoculated intranasally with 150 μl of inoculum containing $10^6$ pfu of the specified virus per animal. Animals were sacrificed four days after inoculation. Lung tissues were harvested and homogenized, and virus titer was determined by plaque assay on Vero cells. Table 7 lists the mean viral titer for each recombinant virus. rg9320C4 and rg9320G4 replicated to a titer of 3.1 and 3.0 $\log_{10}$ pfu/g, respectively, in the lungs of cotton rats. Both G deletion mutants (rg9320ΔG and rg9320ΔHBS) replicated poorly, indicating G deletion affected RSV 9320 replication in the animal host. rg9320ΔG and rg9320ΔHBS are thus potential candidates for live attenuated RSV vaccines.

TABLE 7

Virus replication in cotton rat lung

| virus | log10 mean pfu/g tissue +/− SE |
|---|---|
| rg9320C4 | 3.1 +/− 0.2 |
| rg9320G4 | 3.0 +/− 0.1 |
| rg9320ΔG | 0.4 +/− 0.4 |
| rg9320ΔHBS | 1.0 +/− 0.6 |

Recombinant 9320 and Vaccines

An RSV vaccine would preferably provide protection against both subgroup A and subgroup B RSV infection, which tend to circulate concurrently in communities. Most RSV vaccines developed in the past have been based on the RSV A2 strain. However, it remains to be determined whether an RSV vaccine based solely on a subgroup A strain would provide sufficient immunity to both RSV subgroups. Although recombinant technology has been employed to express subgroup B RSV antigens in the A2 strain, including the replacement of the G and F genes by those of B1 (Whitehead et al. (1999) "Replacement of the F and G proteins of respiratory syncytial virus (RSV) subgroup A with those of subgroup B generates chimeric live attenuated RSV subgroup B vaccine candidates" *J Virol* 73:9773-9780) or 9320 (Cheng et al. (2001) "Chimeric subgroup A respiratory syncytial virus with the glycoproteins substituted by those of subgroup B and RSV without the M2-2 gene are attenuated in African green monkeys" *Virology* 283:59-68) or the insertion of the 9320 G gene in the A2 strain (Jin et al. (1998) *Virology* 251:206-214), subgroup B RSV vaccine development currently lags significantly behind subgroup A vaccine development. Availability of the subgroup B RSV rescue system described herein permits manipulation of the subgroup B RSV genome, e.g., for vaccine development. For example, RSV B9320 can optionally be attenuated by methods used to attenuate subgroup A strains. The methods that have been used to attenuate RSV subgroup A RSV include, e.g., mutagenesis of the viral internal proteins (Lu et al. (2002) "Identification of temperature-sensitive mutations in the phosphoprotein of respiratory syncytial virus that are likely involved in its interaction with the nucleoprotein" *J Virol* 76:2871-2880; Lu et al. (2002) "The major phosphorylation sites of the respiratory syncytial virus phosphoprotein are dispensable for virus replication in vitro" *J Virol* 76:10776-10784; Tang et al. (2002) "Clustered charged-to-alanine mutagenesis of human respiratory syncytial virus L polymerase generated temperature-sensitive viruses" *Virology* 302(207-216); and Tang et al. (2001) "Requirement of cysteines and length of the human respiratory syncytial virus M2-1 protein for protein function and virus viability" *J Virol* 75:11328-11335), deletion of the accessory genes (Bermingham and Collins (1999) *Proc. Natl. Acad. Sci. USA* 96:11259-11264; Jin et al. (2000) *J. Virol.* 74:74-82; Jin et al. (2000) *Virology* 273:210-218; Bukreyev et al. (1997) *J Virol* 71:8973-8982; Teng and Collins (1999) *J Virol* 73:466-473); and introduction of attenuating mutations from different strains to fine-tune the level of attenuation of a vaccine strain (Firestone et al. (1996) "Nucleotide sequence analysis of the respiratory syncytial virus subgroup A cold-passaged (cp) temperature sensitive (ts) cpts-248/404 live attenuated virus vaccine candidate" *Virology* 225:419-422 and Whitehead et al. (1999) "Addition of a missense mutation present in the L gene of respiratory syncytial virus (RSV) cpts530/1030 to RSV vaccine candidate cpts248/404 increases its attenuation and temperature sensitivity" *J Virol* 73:871-877). As one example, from the gene deletion approach, it appears that rA2ΔM2-2 exhibits some desired features for further clinical evaluation (Cheng et al. (2001) *Virology* 283:59-68; Jin et al. (2003) "Evaluation of recombinant respiratory syncytial virus gene deletion mutants in African green monkeys for their potential as live attenuated vaccine candidates" *Vaccine* 21:3647-3652; and Teng et al. (2000) *J Virol* 74:9317-9321); 9320 with a deletion of the M2-2 gene is thus an attenuated 9320 vaccine candidate. Similarly, forcing use of the second or third start codon of the A2 M2-2 mRNA (instead of the first or all three start codons) results in a decrease in M2-2 activity (U.S. patent application Ser. No. 10/672,302 (attorney docket number 26-000320US), filed on Sep. 26, 2003, Jin et al. entitled "Functional mutations in respiratory syncytial virus"). 9320 with a mutation (e.g., substitution or deletion) in the first, second, and/or third start codon of M2-2 is thus an attenuated 9320 vaccine candidate.

As noted, recombinant 9320 viruses with complete or partial deletions of the G gene, e.g., as described herein, are attenuated 9320 vaccine candidates.

While the foregoing invention has been described in some detail for purposes of clarity and understanding, it will be clear to one skilled in the art from a reading of this disclosure that various changes in form and detail can be made without departing from the true scope of the invention. For example, all the compositions and techniques described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. An isolated or recombinant nucleic acid comprising at least one artificially mutated nucleotide relative to SEQ ID NO: 1 or the complementary polynucleotide sequence thereof, wherein the mutated nucleotide comprises one or more of: a deleted nucleotide, an inserted nucleotide, or a substituted nucleotide, and wherein the nucleic acid comprises:

(a) a polynucleotide sequence that is greater than 97.8% identical to SEQ ID NO: 1 or the complementary polynucleotide sequence thereof, as determined by Nucleotide-Nucleotide Basic Local Alignment Search Tool (BLASTN) using default parameters, wherein the polynucleotide sequence encodes an infectious, replicating respiratory syncytial virus (RSV); or (b) a polynucleotide sequence encoding an amino acid sequence or unique subsequence selected from the group consisting of (i) an amino acid sequence that is greater than 99.5% identical to SEQ ID NO: 9, and (ii) an amino acid sequence that is greater than 96.4% identical to SEQ ID NO: 10, as determined by BLASTP using default parameters, wherein an RSV that comprises the amino acid sequence is infectious and replicating.

2. The nucleic acid of claim 1, wherein the nucleic acid is selected from the group consisting of a DNA, a cDNA, an RNA, and an artificial nucleic acid.

3. The nucleic acid of claim 1, wherein the polynucleotide sequence of (a) is at least 98.5% identical to SEQ ID NO: 1 or the complementary polynucleotide sequence thereof, as determined by BLASTN using default parameters.

4. The nucleic acid of claim 1, wherein at least one polypeptide encoded by the nucleic acid comprises at least one deleted, inserted, or substituted amino acid residue.

5. The nucleic acid of claim 4, wherein the polypeptide comprises at least one substituted amino acid residue wherein the substitution is a substitution of a first amino acid with a second amino acid wherein the first amino acid and the second amino acid are both within the same one of the following groups of amino acids: (i) Alanine, Serine, and Threonine; (ii) Aspartic acid and Glutamic acid; (iii) Asparagine and Glutamine; (iv) Arginine and Lysine; (v) Isoleucine, Leucine, Methionine, and Valine; or (vi) Phenylalanine, Tyrosine, and Tryptophan.

6. The nucleic acid of claim 1, wherein the at least one artificially mutated nucleotide is located in the open reading frame encoding the polypeptide of SEQ ID NO: 12.

7. The nucleic acid of claim 1, wherein the open reading frame encoding the polypeptide of SEQ ID NO: 12 is deleted, or wherein the open reading frame encoding the polypeptide of SEQ ID NO:10 is deleted.

8. The nucleic acid of claim 6, wherein the at least one artificially mutated nucleotide comprises a deletion, and wherein the nucleotides encoding amino acid residues 164-197 of SEQ ID NO: 12 are deleted.

9. The nucleic acid of claim 1, wherein the at least one artificially mutated nucleotide is located in the open reading frame encoding the polypeptide of SEQ IDNO: 10.

10. The nucleic acid of claim 9, wherein at least one of the nucleotides encoding amino acid residue 1, amino acid residue 4, amino acid residue 10, or a combination thereof, of SEQ ID NO: 10 is mutated.

11. The nucleic acid of claim 1, wherein the unique polynucleotide subsequence of (b) comprises at least one complete open reading frame which encodes a polypeptide selected from the group consisting of SEQ ID NOs:9 and 10; or comprising a plurality of complete open reading frames.

12. An isolated or recombinant nucleic acid comprising at least one artificially mutated nucleotide relative to SEQ ID NO: 1, wherein the mutated nucleotide comprises one or more of: a deleted nucleotide, an inserted nucleotide, or a substituted nucleotide, and wherein the nucleic acid comprises at least one unique polynucleotide subsequence comprising at least 500 contiguous nucleotides of SEQ ID NO: 1 or the complementary polynucleotide sequence thereof.

13. The nucleic acid of claim 12 wherein the nucleic acid comprises at least one unique polynucleotide subsequence comprising at least 1000 contiguous nucleotides of SEQ ID NO: 1.

14. The nucleic acid of claim 12, wherein the nucleic acid further comprises at least one polynucleotide subsequence from a different strain of virus, at least one polynucleotide subsequence from a different strain of human RSV, or at least one polynucleotide subsequence from a different species of virus.

15. The isolated or recombinant nucleic acid of claim 1, wherein the isolated or recombinant nucleic acid comprises a polynucleotide sequence encoding an amino acid sequence that is greater than 99.5% identical to SEQ ID NO: 9.

16. The isolated or recombinant nucleic acid of claim 15, wherein the amino acid sequence is the amino acid sequence of SEQ ID NO: 9.

17. The nucleic acid of claim 12 wherein the unique polynucleotide subsequence encodes at least 50 contiguous amino acid residues of SEQ ID NO: 10.

* * * * *